United States Patent [19]

Araki et al.

[11] Patent Number: 5,986,150
[45] Date of Patent: Nov. 16, 1999

[54] FLUORINE-CONTAINING OLEFIN, FLUORINE-CONTAINING POLYMER AND THERMOPLASTIC RESIN COMPOSITION PREPARED BY USING SAID POLYMER

[75] Inventors: Takayuki Araki; Tetsuo Shimizu; Takafumi Yamato; Masahiro Kumegawa; Yoshihisa Yamamoto, all of Settsu, Japan

[73] Assignee: Daikin Industries, Ltd., Osaka, Japan

[21] Appl. No.: 08/856,594

[22] Filed: May 15, 1997

Related U.S. Application Data

[62] Division of application No. 08/596,315, filed as application No. PCT/JP95/01103, Jun. 5, 1995, Pat. No. 5,670,593.

[30] Foreign Application Priority Data

Jun. 9, 1994 [JP] Japan .................................. 6-153020

[51] Int. Cl.$^6$ .......................... C07C 33/42; C07C 41/00; C07D 303/08
[52] U.S. Cl. .......................... 568/843; 568/674; 549/563
[58] Field of Search ..................... 568/843, 674; 549/563

[56] References Cited

U.S. PATENT DOCUMENTS

| | | | |
|---|---|---|---|
| 4,544,720 | 10/1985 | Ohmori et al. | 526/247 |
| 4,581,412 | 4/1986 | Ohmori et al. | 525/199 |
| 4,581,413 | 4/1986 | Kim | 525/221 |

FOREIGN PATENT DOCUMENTS 63-31487  2/1988  Japan .

OTHER PUBLICATIONS

In–House Computer Generated pp. 1–4 Answer 1 of 2 by Nobuhiko et al, JP94–207359–940831.

In–House Computer Generated pp. 4–24 Answer 2 of 2 by Takayuki et al, JP 94–153020–940609.

International Search Report for International Application No. PCT/JP95/01103 Supplementary European Search Report for Appln. No. EP 95 92 0259, dated Apr. 11, 1996.

Databases "Registry", "Chemical Abstracts" (Host: STN); R.N.: 70641–93–9 and abs. 91: 29 666, Colombus, OH, USA; & JP–A–54 023 099 (Asahi Glass Co., Ltd.) Feb. 21, 1979.

*Primary Examiner*—Joseph L. Schofer
*Assistant Examiner*—N. Sarofim
*Attorney, Agent, or Firm*—Varndell Legal Group

[57] ABSTRACT

To provide a fluorine-containing olefin represented, for example, by $CH_2{=}CFCF_2{-}R_f^6{-}(CH_2)_k{-}X^2$ [wherein, $X^2$ is

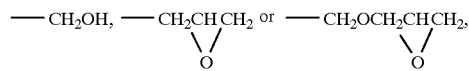

$R_f^6$ is a fluorine-substituted fluorine-containing alkyl group having 1 to 40 carbon atoms or $-OR_f^7-$ ($Rf^7$ is a fluorine-substituted fluorine-containing alkyl group having 1 to 40 carbon atoms or a fluorine-substituted fluorine-containing ether group having 3 to 50 carbon atoms), k is 0 or an integer of 1 to 6]; a fluorine-containing polymer with functional group which is prepared by polymerizing the above-mentioned olefin, has good affinity with various heat-resisting thermoplastic resins and is capable of forming homogeneous dispersion with the thermoplastic resin; and a thermoplastic resin composition comprising the above-mentioned fluorine-containing polymer with functional group and an aromatic polyester or the like as the heat-resisting thermoplastic resin.

10 Claims, 6 Drawing Sheets

1  SURFACE TENSION OF EXAMPLE 11
2  SURFACE TENSION OF EXAMPLE 12

3 STRESS-STRAIN CURVE OF EXAMPLE 66
4 STRESS-STRAIN CURVE OF EXAMPLE 67
5 STRESS-STRAIN CURVE OF EXAMPLE 68
6 STRESS-STRAIN CURVE OF COMPARATIVE EXAMPLE 22

FLUORINE-CONTAINING OLEFIN, FLUORINE-CONTAINING POLYMER AND THERMOPLASTIC RESIN COMPOSITION PREPARED BY USING SAID POLYMER

CROSS-REFERENCE TO RELATED APPLICATIONS

This is a divisional application of U.S. Ser. No. 08/596,315, filed Feb. 9, 1996, now U.S. Pat. No. 5,670,593, which was a U.S. national phase application of International Application No. PCT/JP95/01103, filed Jun. 5, 1995.

TECHNICAL FIELD

The present invention relates to a novel fluorine-containing polymer with functional group, which has excellent affinity with various heat-resisting thermoplastic resins and is capable of forming homogeneously dispersed conditions.

Further the present invention relates to a novel fluorine-containing olefin with functional group, which can give a functional group to the fluorine-containing polymer.

Further the present invention relates to a thermoplastic resin composition which has improved mechanical properties and chemical properties and comprises the above-mentioned fluorine-containing polymer with functional group and a thermoplastic resin having a melting point of crystal or glass transition temperature of not less than 150° C.

BACKGROUND ART

Crystalline heat-resisting thermoplastic resins (these have a melting point of crystal of not less than 150° C.) such as polyacetal, polyamide, aromatic polyester, poly(arylene sulfide), polyketones, poly(ether ketones), polyamideimide and poly(ether nitrile) are excellent in mechanical properties and moldability, and therefore are used for functional parts in the fields of automobiles, industrial machineries, office automation equipments, electrical and electronic equipments and the like. However there is a market demand for higher chemical resistance and sliding property and in addition, since these resins are generally brittle, enhancement in impact resistance is particularly desired. Also non-crystalline heat-resisting thermoplastic resins (these have a glass transition temperature of not less than 150° C.) such as polycarbonate, poly(phenylene ether), polyarylate, polysulfone, poly(ether sulfone) and poly(ether imide) are widely employed for uses where their transparency, dimensional stability, impact resistance and the like are utilized, but generally have problems of chemical resistance, solvent resistance and moldability.

From another aspect, fluorine-containing resins such as polytetrafluoroethylene (PTFE), tetrafluoroethylene/perfluoro(alkyl vinyl ether) copolymer (PFA), tetrafluoroethylene/hexafluoropropylene copolymer (FEP), poly(vinylidene fluoride) (PVDF) and ethylene/tetrafluoroethylene copolymer (ETFE) are excellent in thermal resistance, chemical resistance, solvent resistance, weather resistance, sliding property, flexibility, electrical properties and the like, and are widely used in the fields of automobiles, industrial machineries, office automation equipments, electrical and electronic equipments and the like. However as compared with the crystalline heat-resisting thermoplastic resins, in many cases, the fluorine-containing resins are inferior in mechanical properties and physical heat resistance as shown by a deflection temperature under load, and also are inferior in dimensional stability as compared with non-crystalline heat-resisting thermoplastic resins, and thus their application is limited.

In order to eliminate the drawbacks of the above-mentioned non-fluorine type heat-resisting thermoplastic resins, attempts for preparing novel materials have been aggressively made by combining with a fluorine-containing polymer (resinous and elastomeric ones are included) or, contrarily, by modifying the resinous fluorine-containing polymer with a non-crystalline heat-resisting thermoplastic resin.

First, as an example of simple melt-blending by means of a kneader, for instance, JP-A-202344/1982 discloses that a commercially available fluorine-containing elastomer is added to poly(arylene sulfide) for the purpose to improve impact resistance, crack resistance and strength against thermal shock without impairing the characteristics of poly(arylene sulfide) such as thermal resistance and chemical resistance. Also JP-A-165647/1989 and JP-A-110156/1990 disclose that a polymer forming an anisotropic melt, i.e. a liquid crystal polymer (aromatic polyester and the like) is added for the purpose to decrease a coefficient of linear expansion and further to improve mechanical properties and moldability without impairing weather resistance, chemical resistance, wear resistance and antisoil property of the fluorine-containing polymer such as PVDF. As examples of a blend of a liquid crystal polymer and PTFE, there are JP-B-5693/1992 and JP-A-230756/1988. JP-A-7850/1975 discloses that it is effective to blend PVDF for improving water absorption property and hygroscopicity of polyamide.

Further JP-A-23448/1985 discloses an example of improving mold-release property by incorporating a fluorine-containing polymer to an aromatic polysulfone composition of which shrinkage from mold dimensions is reduced by adding fibrous reinforcing agents such as glass fibers and wollastonite and inorganic fillers such as talc and glass beads.

Also attempts to improve sliding property by mixing PTFE powder to various synthesized resins have been widely conducted.

However there is a problem that usually the fluorine-containing polymer has poor affinity with other materials, because of a small surface energy thereof. For that reason, when the fluorine-containing polymer is melt-blended with other materials, there occurs a phase separation, and an interfacial adhesivity therebetween is substantially zero, and thus interfacial adhesion failure is easy to occur. In addition, the fluorine-containing polymer is difficult to disperse into other materials during blending, which results in aggregation and makes it difficult to sufficiently exhibit effects of adding the fluorine-containing polymer.

In order to resolve these drawbacks or enhance affinity between the different polymers, there is often added a compatibilizing agent as a third component. JP-A-218446/1987 discloses a composition prepared by blending a thermoplastic fluorine-containing elastomer in order to improve impact resistance of poly(arylene sulfide) without impairing its flowability, and teaches that it is more effective to add a polymer containing a fluorinated aliphatic group for improving the affinity. Also JP-A-62853/1991 discloses a method of adding, as a compatibilizing agent, a graft polymer comprising a vinyl polymer having epoxy group and methyl methacrylate polymer or acrylonitrile/styrene copolymer when blending poly(arylene sulfide) and a thermoplastic resin including PVDF.

Also claim 2 of the above-mentioned JP-A-165647/1989, JP-A-197551/1989 and JP-A-263144/1989 disclose that it is more effective to add an acrylic polymer, poly(vinyl acetate) and poly(vinyl methyl ketone), respectively to the blend of PVDF and an anisotropic melt-forming polymer as compared with simple blending.

In JP-A-11109/1989 there is described an example of using, as a compatibilizing agent for blending polyamide and PVDF, a block polymer comprising any one of N-vinylpyrrolidone or methyl (meth)acrylate and any one of an ethylenically unsaturated monomer, polycondensated monomer or lactum.

Also JP-A-98650/1989 and JP-A-110550/1989 disclose the use, as a compatibilizing agent when blending poly (phenylene ether) and a fluorine-containing polymer such as PVDF, of a copolymer comprising polystyrene and an acrylic polymer by utilizing excellent affinities of poly (phenylene ether) with polystyrene and of PVDF with an acrylic polymer.

However in JP-A-218446/1987, the effect of improvement in affinity is not enough because the fluorinated aliphatic group in the compatibilizing agent has a low degree of polymerization, i.e., not more than 20 of carbon atoms. Also all the other patent publications substantially direct to examples of using non-fluorine type compatibilizing agents synthesized by utilizing the excellent affinity between the PVDF and the carbonyl group-containing polymer such as an acrylic polymer, and thus the fluorine-containing polymer is limited to PVDF. Also in the affinity improving method using such compatibilizing agents, since chemical resistance and thermal resistance of the compatibilizing agents themselves are poorer than those of the main component polymer, there is a problem that physical properties of molded articles are lowered.

There are also attempts to improve dispersibility of compositions comprising fluorine-containing polymers and thermoplastic resins by so-called dynamic vulcanization. JP-A-185042/199 1 discloses that, when blending a crosslinkable fluorine-containing elastomer and a thermoplastic polymer having a melting point of crystal or glass transition temperature of not less than 150° C., dispersibility of the fluorine-containing elastomer is improved to give a thermoplastic elastomer by conducting vulcanization of the fluorine-containing elastomer during melt-blending. Also in JP-A-172352/1991, fine dispersion of fluorine-containing rubbers has been achieved by utilizing the dynamic vulcanization method for improving impact resistance of poly (phenylene sulfide) with a fluorine-containing elastomer.

However in these dynamic vulcanization methods, since the fluorine-containing elastomer is vulcanized during melt-blending with other materials, impurities derived from a vulcanizing agent and other additives to be usually used for vulcanization remain in the composition, which makes the properties of molded articles such as chemical resistance lowered.

Also particularly because in a dynamically vulcanized composition comprising the thermoplastic resin and the fluorine-containing elastomer, the thermoplastic resin becomes a matrix, for example, chemical resistance of the composition is easy to be influenced by characteristics of the thermoplastic resin, and the effect of adding the fluorine-containing elastomer is not sufficiently obtained.

On the other hand, there are reports with respect to a composition comprising a fluorine-containing polymer with reactive functional group. JP-A-105062/1988, JP-A-254155/1988 and JP-A-264672/1988 disclose examples of a blend of a matrix polymer with a fluorine-containing polyether with functional group at its end(s), a polymer containing functional group and a polyfluoroalkyl group having 2 to 20 carbon atoms or a fluorine-containing elastomer with functional group. However, either of these examples is conducted in the way of letting two functional group-containing polymers disperse in the matrix polymer and react with each other to form a network structure, and then physically bond the network structure to the matrix polymer. Namely, the way does not directly utilize chemical affinity and reactivity with the matrix polymer.

Therefore a combination of two or more functional groups which react with each other is necessary, and it is required to regulate the conditions where those functional groups give a network structure. Also the fluorine-containing polyether is usually obtainable as an oily substance and is expensive, and moreover the effect of addition is limited to improvement of lubricity of the matrix polymer. Further as the polyfluoroalkyl-containing polymer, only ones having low molecular weight, which are difficult to be defined as polymer, are exemplified.

Also JP-A-112612/1993 discloses modified fluorohydrocarbon polymers to which substituents such as vinyl, allyl, acrylate, alkoxysilane, amide, sulfonic acid salt, pyridine and carboxylic acid salt are introduced. There is also described that among these substituents, particularly amide is further converted to amino and carboxylester being converted to carboxyl, and thus it is possible to graft to an aromatic polyamide and aromatic polyester. Also it is mentioned that the graft polymers are used for blending with commercially available engineering polymers to improve their surface characteristics, weather resistance, wear resistance and water absorption property.

However the substituents of these modified polymers are introduced by polymer reaction wherein Y-R-Z which is a combination of a highly reactive nucleophilic group Y (amino, oxy, thio) and the above-mentioned modifying substituent Z being connected through a bonding segment R, is reacted with a double bond formed in the vinylidene polymer by dehydrofluorination of the polymer.

That is, because of polymer reaction, it is difficult to introduce the substituents uniformly, and for that reason, there occurs an irregular distribution in the concentration of functional groups, and thus it is difficult to obtain sufficient effect on dispersibility and affinity at the time of blending with the thermoplastic resin.

Also at the time of introduction of the modifying substituents and hydrolysis of amide or carboxylester, there remains a reactive reagent, which results in lowering of thermal resistance and chemical resistance. Further since the bonding segment of the modifying reagent is of hydrocarbon type, thermal resistance of the obtained polymer itself is lowered at that portion and the polymer is decomposed when kneading with the heat-resisting thermoplastic resin at high temperature to lower the physical properties of the blended composition. Also the vinylidene polymer, after the dehydrofluorination, is colored markedly and external appearance of the molded article is impaired remarkably. Also in this method, the fluorine-containing polymer is limited to vinylidene fluoride polymers, and also introduction of hydroxyl group and glycidyl group is difficult, and thus sufficient effects of enhancing dispersibility cannot be obtained in blending with an aromatic polyester, polycarbonate and poly(phenylene sulfide). Further there is no detailed description as to examples of the composition blended with the heat-resisting thermoplastic resin and the physical properties at the time of blending.

JP-A-8 1159/1988 discloses that mechanical properties of a thermoplastic elastomer composition can be improved by modifying a fluorine-containing rubber with any one of carboxyl, hydroxyl or epoxy group when blending a poly (ether ester amide) and the fluorine-containing rubber.

However the described fluorine-containing rubber with functional group is prepared by copolymerizing a fluorine-containing monomer and an acrylic monomer with functional group to introduce the functional group. Therefore, the thermal resistance and chemical resistance are lowered and physical properties of a molded article is lowered when blended with the heat-resisting thermoplastic resin. The functional group-containing acrylic monomer has poor copolymerizability with a fluorine-containing monomer represented by tetrafluoroethylene and vinylidene fluoride, and a uniform concentration of functional groups is difficult to obtain in every polymer molecule, which results in an irregular distribution of components. Thus it is difficult to obtain sufficient effects on dispersibility and affinity in blending with the thermoplastic resin. Also poly(ether ester amide) is usually low in chemical resistance as compared with polyamide.

As mentioned above, when blending a fluorine-containing polymer and a thermoplastic resin, since the fluorine-containing polymer usually has poor affinity, it is difficult to obtain a blend having stable characteristics, and physical properties of the molded article obtained therefrom is lowered. Also though various attempts have been made for improving the affinity, such as study on additives and modification and denaturation of the fluorine-containing resin, there have not been obtained a fluorine-containing polymer and a composition prepared by mixing the fluorine-containing polymer and a thermoplastic resin, which do not lower thermal resistance and chemical resistance of the composition.

SUMMARY OF THE INVENTION

An object of the present invention is to provide a novel fluorine-containing polymer with functional group, which has good affinity with various heat-resisting thermoplastic resins and is capable of forming homogeneous dispersed conditions, and a novel fluorine-containing olefin with functional group for preparation of the fluorine-containing polymer.

Further another object of the present invention is to provide a thermoplastic resin composition which is improved in interfacial affinity by blending the above-mentioned fluorine-containing polymer with functional group and various heat-resisting thermoplastic resins and can give excellent mechanical properties, moldability, thermal resistance and chemical resistance to molded articles.

DISCLOSURE OF THE INVENTION

The fluorine-containing olefin with functional group of the present invention is represented by the formula (IV):

$$CH_2=CFCF_2-R_f^6-(CH_2)_k-X^2 \qquad (IV)$$

wherein $X^2$ is

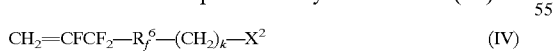

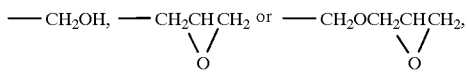

$R_f^6$ is a fluorine-substituted alkylene group having 1 to 40 carbon atoms or $-OR_f^7-(R_f^7$ is a fluorine-substituted fluorine-containing alkylene group having 1 to 40 carbon atoms or a fluorine-substituted fluorine-containing ether group having 3 to 50 carbon atoms), k is 0 or an integer of 1 to 6, or represented by the formula (V):

$$CH_2=CFCF_2-R_f^8-(CH_2)_m-COOR^4 \qquad (V)$$

wherein $R^4$ is H, an alkyl group having 1 to 6 carbon atoms, Na, K, Li or $NH_4$, $R_f^8$ is a fluorine-substituted alkylene group having 3 to 40 carbon atoms or $-OR_f^9-(R_f^9$ is a fluorine-substituted alkylene group having 2 to 40 carbon atoms or a fluorine-substituted ether group having 3 to 50 carbon atoms), m is 0 or an integer of 1 to 6.

The fluorine-containing polymer with functional group of the present invention is a copolymer of the following (A) and (B) and is characterized by comprising 0.01 to 80% by mole of (A) and 20 to 99.99% by mole of (B) and having a number average molecular weight of 2,000 to 20,000,000.

(A) is one or more monomers represented by the formula (I):

$$CH_2=CFCF_2-R_f^1-(CH_2)_a-X^3 \qquad (I)$$

wherein $X^1$ is $-CH_2OH$, $-COOR^1$ ($R^1$ is H, an alkyl group having 1 to 6 carbon atoms, Na, K, Li or $NH_4$),

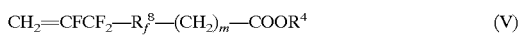

$R_f^1$ is a fluorine-substituted alkylene group having 1 to 40 carbon atoms or $-OR_f^2-(R_f^2$ is a fluorine-substituted alkylene group having 1 to 40 carbon atoms or a fluorine-substituted ether group having 3 to 50 carbon atoms), a is 0 or an integer of 1 to 6, and (B) is one or more monomers selected from the group consisting of monomers represented by the formula (II):

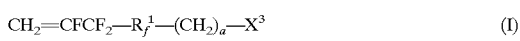

wherein $Y^1$ is F, Cλ, H or $CF_3$, $Y^2$ is F, Cλ, H, $R_f^3$ ($R_f^3$ is a perfluoroalkyl group having 1 to 10 carbon atoms) or

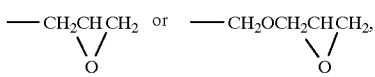

(b is 0 or an integer of 1 to 5, $R_f^4$ is a perfluoroalkyl group having 1 to 6 carbon atoms) and the formula (III):

wherein $Z^1$ is F, H, an alkyl group having 1 to 6 carbon atoms or a perfluoroalkyl group having 1 to 10 carbon atoms, $Z^2$ is H, Cλ, an alkyl group having 1 to 6 carbon atoms or $-(CF_2)_d-Z^3$ (d is an integer of 1 to 10, $Z^3$ is F or H).

The thermoplastic resin composition of the present invention comprises (D) 0.1 to 99% by weight of at least one selected from the above-mentioned fluorine-containing polymers with functional group as the fluorine-containing polymer with functional group and (E) 1 to 99.9% by weight of a heat-resisting thermoplastic resin having a melting point of crystal or glass transition temperature of not less than 150° C.

The present inventions are explained below in order.

The first one of the present inventions relates to a novel fluorine-containing olefin with functional group, which can give hydroxyl, glycidyl, carboxyl or carboxylester to the fluorine-containing polymer.

As a comonomer giving a similar functional group to the polymer, there are most generally known (meth)acrylate or (meth)acrylic acid compounds with hydroxyl, glycidyl and carboxyl, and vinyl ethers represented by hydroxyalkyl vinyl ether and glycidyl vinyl ether. Those hydrocarbon type unsaturated compounds with functional group have such drawbacks that copolymerizability with fluoroolefins (olefins represented by tetrafluoroethylene, vinylidene fluoride, chlorotrifluoroethylene and the like) is insufficient and that even if the copolymerization is possible, thermal resistance and chemical resistance of the obtained copolymer are lowered significantly.

On the other hand, as the fluorine-containing olefin with functional group, in JP-A-54409/1988 there is reported a compound represented by $CH_2=CF-(CF_2)_{60}-(CH_2)_\beta-X$ (X is

However because of its insufficient copolymerizability with fluoroolefins, the polymerization rate is lowered and a large amount of the compound is necessary to obtain a copolymer having a desired composition.

JP-A-143888/1975 discloses a hemi-acetal compound represented by

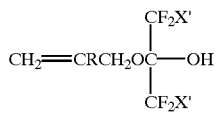

wherein R is H or methyl, X' is F or Cλ, and JP-A-503 104/1993 discloses a partly fluorine-substituted compound represented by $CH_2=CH-Rf-CH_2CH_2Y$, wherein Rf is a fluorine-substituted divalent organic group, Y is $CH_2OH$, COOH or others. Polymers prepared from these monomers have a drawback such that tertiary hydrogen like

is yielded in trunk chains of the polymers, and thermal resistance of the obtained copolymer is lowered and particularly at high temperature, deterioration is easy to occur. Also the above-mentioned hemi-acetal compound has a poor copolymerizability with a fluorine-containing monomer, and particularly it is difficult to obtain a high molecular weight.

JP-A-85832/1983 and JP-A-503935/1993 disclose fluorine-containing olefins with hydroxyl and having a perfluoro(vinyl ether) group, and U.S. Pat. No. 4,209,635 discloses fluorine-containing olefins with a carboxylester group and having perfluoro(vinyl ether) group. A $CF_2=CFO-$ group in these fluorine-containing olefins has less resistance to alkaline medium. Particularly the fluorine-containing olefin with hydroxyl and having a perfluoro(vinyl ether) group may easily cause cyclization of vinyl ether itself, homopolymerization reaction (fluorine-containing polyether is formed) and hydrolysis of the vinyl ether group under an environment of an acidity (for example, PKa is not less than 7) lower than that (PKa≈5 to 6) of hydroxyl group. Therefore for instance, at the time of copolymerizing with other ethylenically unsaturated compounds in an aqueous medium, polymerization rate is lowered under a weak alkaline to alkaline condition, and an amount of vinyl ether to be introduced into the copolymer decreases. Therefore the polymerization conditions cannot be selected from a wide range. Also a method of synthesizing those perfluoro(vinyl ether) compounds with functional group is complicated and therefore such compounds are expensive and economically disadvantageous in industrial scale.

An object of the present invention is to eliminate the above-mentioned drawbacks and to provide a novel fluorine-containing olefin with functional group which is capable of endowing a fluorine-containing polymer with functional groups. Specifically, according to the present invention there can be provided a novel fluorine-containing olefin which can introduce highly reactive functional groups into a fluorine-containing polymer, and has the following characteristics.

① Good copolymerizability with an ethylenically unsaturated compound, particularly an ethylenically unsaturated fluorine-containing compound. Thus a reaction rate is not lowered remarkably, ② Not lowering thermal stability and chemical stability of the resulting copolymer prepared by copolymerizing with the ethylenically unsaturated fluorine-containing compound, and ③ Synthesis of the fluorine-containing olefin with functional group of the present invention being relatively easy and industrially produceable.

The first fluorine-containing olefin with functional group of the present invention is the fluorine-containing olefin which has hydroxyl group or glycidyl group and is represented by the formula (IV):

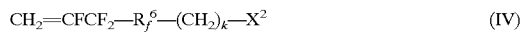

wherein, $X^2$ is

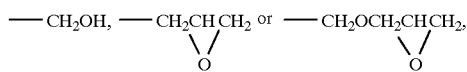

$R_f^6$ is a fluorine-substituted alkylene group having 1 to 40 carbon atoms or $-OR_f^7-$ ($R_f^7$ is a fluorine-substituted alkylene group having 1 to 40 carbon atoms or a fluorine-substituted ether group having 3 to 50 carbon atoms), k is 0 or an integer of 1 to 6.

In the fluorine-containing olefin of the formula (IV), one of the structures of $R_f^6$ is a fluorine-substituted alkylene group having 1 to 40 carbon atoms which includes a linear group, a branched group or a mixture thereof.

A preferable typical example among those is the fluorine-containing olefin represented by the formula (1):

wherein $X^3$ and b' are the same as the above-mentioned $X^2$ and k, respectively, a' is 0 or an integer of 1 to 10.

Further preferable typical examples are fluorine-containing olefins represented by the formula (1-a):

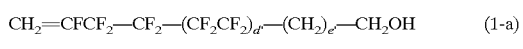

wherein d' is 0 or an integer of 1 to 10, e' is an integer of 1 to 5, the formula (1-b):

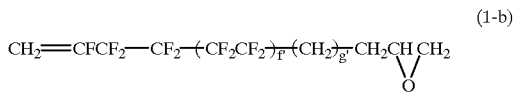

wherein f' is 0 or an integer of 1 to 10, g' is 0 or an integer of 1 to 6, and the formula (1-c):

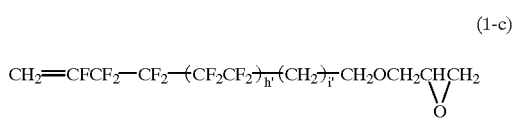

wherein h' is 0 or an integer of 1 to 10, i' is an integer of 1 to 5.

The preferable examples of the fluorine-containing olefin represented by the formula (1-a) are $CH_2=CFCF_2CF_2CH_2CH_2OH$, $CH_2=CFCF_2CF_2CF_2CF_2CH_2CH_2OH$, $CH_2=CFCF_2CF_2CF_2CF_2CF_2CF_2CH_2CH_2OH$, $CH_2=CFCF_2CF_2-(CF_2CF_2)_3-(CH_2)_3-CH_2OH$ and the like.

The preferable examples of the fluorine-containing olefins represented by the formula (1-b) are

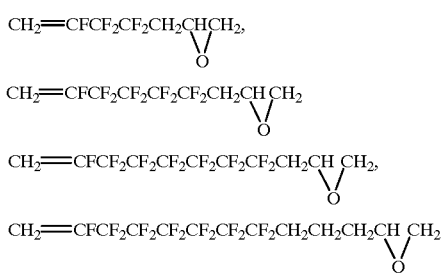

and the like.

The preferable examples of the fluorine-containing olefins represented by the formula (1-c) are

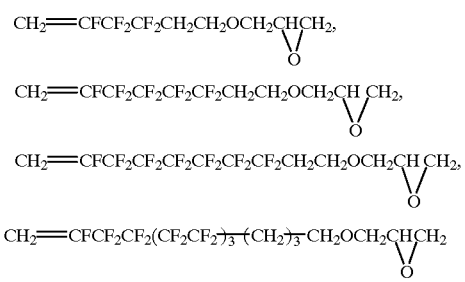

and the like.

There are various methods of synthesis of the fluorine-containing olefins of the formula (1), and for example, they can be synthesized in the manner mentioned below.

In the first place,

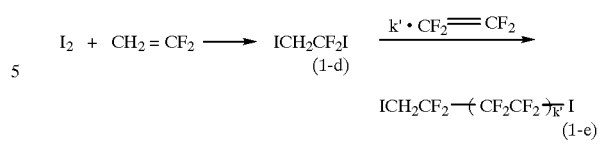

(k' is an integer of 1 to 11).

The fluorine-containing olefin (1-e) can be prepared by telomerization of tetrafluoroethylene in the presence of a radical initiator after an addition reaction of iodine with vinylidene fluoride.

The reaction of tetrafluoroethylene with the compound of the formula (1-d) obtained by adding iodine to vinylidene fluoride is carried out in the presence of a radical initiator such as a peroxide and an azo-compound at a reaction temperature of from room temperature to 200° C., preferably from 40° to 100° C. The tetrafluoroethylene is subjected to bubbling at normal pressure or under a pressure of not more than 15 kgf/cm²G, preferably by keeping at normal pressure or a pressure of not more than 5 kgf/cm²G. Thus (1-e) can be prepared.

As the peroxides, examples are tert-butyl peroxyisobutyrate, tert-butyl peroxy(2-ethylhexanoate), iso-butyrylperoxide, di-iso-propyl peroxydicarbonate, di-n-propyl peroxydicarbonate and the like, and examples of the azo-compounds are azobisisobutyronitrile and the like. No solvent is used, or for example, there can be used Flon type solvents such as R-113, R-114, R-141b and R-115; chlorine type solvents such as carbon tetrachloride, chloroform and methylene chloride; hydrocarbon type solvents such as hexane and cyclohexane; aromatic solvents such as benzene and toluene; and the like. Particularly Flon type solvents are preferable.

The compounds, i.e. the compound of the formula (1-a) with hydroxyl group, the compound of the formula (1-b) with glycidyl group and the compound of the formula (1-c) with glycidyl ether group can be synthesized by using the thus obtained compound of the formula (1-e) as a starting material.

The fluorine-containing olefin of the formula (1-a) with hydroxyl group can be synthesized, for instance, in the following manner.

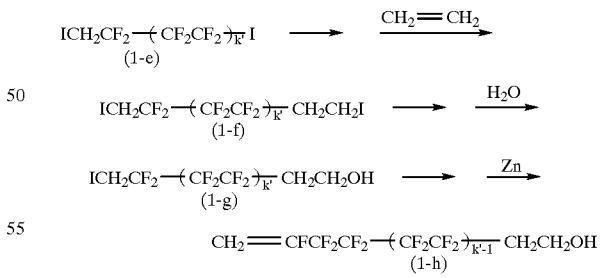

That is, ethylene is reacted with the compound of the formula (1-e) in the presence of a radical initiator to give (1-f), and then water is reacted with the iodine at the ethylene-introduced side to convert to —OH group. After that, the fluorine-containing olefin with hydroxyl group can be prepared through de-IF reaction by using a metal such as Zn.

The compound of the formula (1-f) can be prepared by reacting (1-e) and ethylene in the presence of a radical initiator such as a peroxide and an azo-compound or by irradiating ultraviolet rays normally at 20° to 200° C., preferably 50° to 100° C. with maintaining a pressure of from normal pressure to 50 kgf/cm$^2$G, preferably normal pressure or a pressure of not more than 10 kgf/cm$^2$G.

As the above-mentioned peroxides, examples are tert-butyl peroxyisobutyrate, tert-butyl peroxy(2-ethylhexanoate), iso-butyrylperoxide, di-iso-propyl peroxydicarbonate, di-n-propyl peroxydicarbonate and the like, and examples of the azo-compounds are azobisisobutyronitrile and the like. As the solvent, one similar to those for the telomerization of tetrafluoroethylene is preferable.

There are various methods adopted for hydroxylation of the iodine atom at the ethylene-introduced side of the ethylene adducts of the formula (1-f). For example, there can be used a method of reacting with chlorosulfonic acid and water in order, a method of reacting with $H_2O$ in DMF as described in JP-B-8807/1977, a method of reacting with $H_2O$ in dimethyl sulfoxide as mentioned in JP-B-28585/1990 and the like.

Further the desired fluorine-containing olefin compound (1-h) with hydroxyl group can be prepared through the de-IF reaction from the compound (1-g) in a polar solvent by using a dehalogenizing agent such as zinc.

As the solvent in this reaction, there are preferably used, for example, ether type solvents such as monoglyme, diglyme and dioxane; alcohol type solvents such as methanol and ethanol; ketone type solvents such as acetone and MEK; water; DMF and the like. Particularly methanol, diglyme and the like are preferable.

For the de-IF reaction, usual dehalogenizing agents are used, and in addition to zinc, there are used magnesium, tin, copper, iron, sodium, manganese and the like. From a point of reaction rate, zinc and magnesium are preferable. The reaction temperature is from 20° to 150° C., preferably from 40° to 80° C. An amount in molar ratio of the dehalogenizing agent is 1.0 to 5 times, preferably 1.02 to 3 times that of the compound (1-g). The reaction is preferably carried out by adding zinc powder to the solvent, stirring, dispersing and then heating, and thereafter adding thereto the compound (1-g) slowly and dropwise to complete the reaction.

The method of synthesizing a fluorine-containing olefin, i.e. the compound (1-b) with glycidyl group is, for example, as follows:

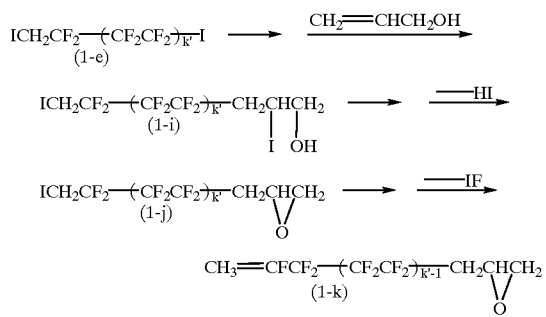

that is, after preparation of the compound (1-i) by reacting allyl alcohol with the compound (1-e) in the presence of a radical initiator, dehydroiodination is carried out by using a base to form an epoxy ring. Then the fluorine-containing olefin with glycidyl group can be prepared by the de-IF reaction by using a metal such as zinc. The reaction of the compound (1-e) and allyl alcohol can be achieved in the presence of the radical initiator such as a peroxide or an azo-compound which is similar to one used in the reaction with tetrafluoroethylene or ethylene, at a reaction temperature of 20° to 200° C., preferably 50° to 150° C.

Subsequently the compound (1-j) with epoxy ring can be prepared by reacting the compound (1-i) and a little bit excess amount of the base for the de-HI reaction. As the base, preferable are a hydroxide such as sodium hydroxide, potassium hydroxide or calcium hydroxide, an alkalline metal carbonate such as sodium carbonate or sodium hydrogencarbonate, a metal alkoxide such as sodium methoxide, sodium ethoxide or potassium-tert-butoxide, a tertiary amine such as triethylamine or pyridine, and the like. Also in order to prevent the formed epoxy ring from opening, particularly preferable are sodium hydroxide, potassium hydroxide, calcium hydroxide, alkalline metal carbonates and tertiary amines.

The reaction proceeds without a solvent. In case where a solvent is used, there are preferably used, for example, water, an alcohol type solvent such as methanol or ethanol, an ether type solvent such as tetrahydrofuran, dioxane, monoglyme or diglyme, a ketone type solvent such as acetone, methyl ethyl ketone or methyl isobutyl ketone, a tertiary amine type solvent such as triethylamine or pyridine, dimethylformamide, dimethylsulfoxide, and the like. Also in order to prevent the formed epoxy ring from opening, it is preferable that no solvent is used or even if the solvent is used, particularly preferable are ether type, ketone type and tertiary amine type solvents, dimethylformamide, dimethylsulfoxide and the like.

The de-IF reaction from the obtained compound (1-j) can be carried out by using a metal such as Zn in the same manner as in the reaction for the de-IF reaction of the compound (1-g). As the solvent, the use of water and the alcohol type solvent such as methanol or ethanol should be avoided in order to prevent the formed epoxy ring from opening.

There are various methods to synthesize the fluorine-containing olefin (1-c) with glycidyl ether group. The olefin can be prepared by reacting a fluorine-containing olefin (1-h) with hydroxyl group and epichlorohydrine.

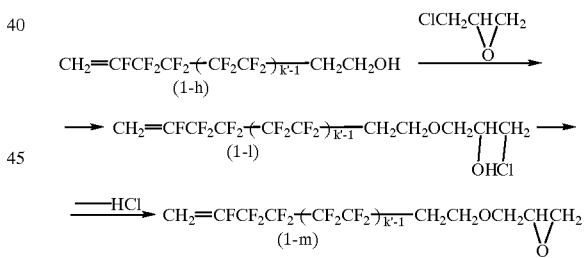

For example, acidic catalysts of Lewis acid such as $BF_3(C_2H_5OC_2H_5)_3$ and $SnCl_4$ can be used, and $BF_3(C_2H_5OC_2H_5)_3$ is preferable. The compound (1-m) can be prepared by acting the acidic catalyst on the compound (1-h) and epichlorohydrine to form the compound (1-l) and then carrying out dehydrochlorination reaction by using a base.

The reaction temperature is from −10° to 200° C., preferably from 0° to 100° C. A solvent may not be used, but, for example, an ether type solvent such as monoglyme, diglyme, dioxane or tetrahydrofuran, a ketone type solvent such as acetone or MEK, a hydrocarbon type solvent such as hexane or cyclohexane, a chlorine type solvent such as chloroform, dichloromethane or carbon tetrachloride, and a Flon type solvent such as R-113, 141b or 115 are preferable, and the ether type solvent is particularly preferable.

The dehydrochlorination reaction of the compound (1-l) can be carried out in the same manner as in the abovementioned preparation of the compound (1-j) through the de-HI reaction of the compound (1-i) by using a base.

Also through the reaction of a base, an equivalent or more amount of epichlorohydrine and the compound (1-h), the compound (1-m) can be synthesized. As the base, there are preferably used sodium hydroxide, potassium hydroxide, sodium hydride and the like. The reaction temperature is from 20° to 200° C., preferably from 50° to 150° C. A solvent may not be used, but, for example, when used, preferable are an ether type solvent such as monoglyme, diglyme, dioxane or tetrahydrofuran, a ketone type solvent such as acetone or MEK, a hydrocarbon type solvent such as hexane or cyclohexane, a chlorine type solvent such as chloroform, dichloromethane or carbon tetrachloride, a Flon type solvent such as R-113, 141 b, 115 or the like. No solvent or the use of ether type solvent is particularly preferable.

Another structure of $R_f^6$ in the fluorine-containing olefin of the formula (IV) is an ether group represented by $-OR_f^7-$, and $-R_f^7-$ is a fluorine-substituted alkylene group having 1 to 40 carbon atoms or a fluorine-substituted ether group having 3 to 50 carbon atoms and includes linear or branched groups or a mixture thereof.

Among them, preferable typical example is a fluorine-containing olefin represented by the formula (2):

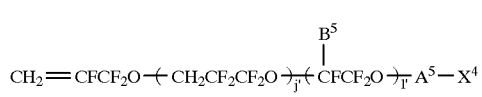
(2)

wherein $X^4$ is

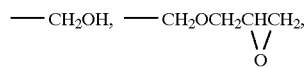

$A^5$ is

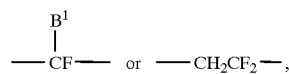

$B^5$ is $CF_3$ or F, j' is 0 or an integer of 1 to 5, l' is 0 or an integer of 1 to 10.

Further preferable typical examples are fluorine-containing olefins represented by the compounds (2-a), (2-b), (2-c) and (2-d):

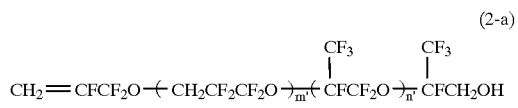
(2-a)

wherein m' is 0 or an integer of 1 to 5, n' is 0 or an integer of 1 to 10,

(2-b)

wherein o' is 0 or an integer of 1 to 5, p' is 0 or an integer of 1 to 10,

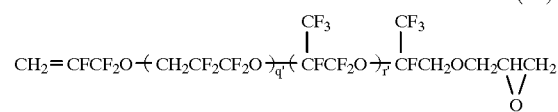
(2-c)

wherein q' is 0 or an integer of 1 to 5, r' is 0 or an integer of 1 to 10 and

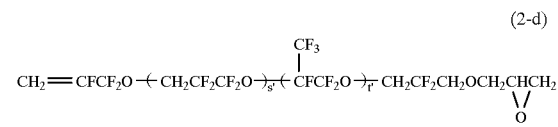
(2-d)

wherein s' is 0 or an integer of 1 to 5, t' is 0 or an integer of 1 to 10.

The preferable examples of the fluorine-containing olefins represented by the formula (2-a) are

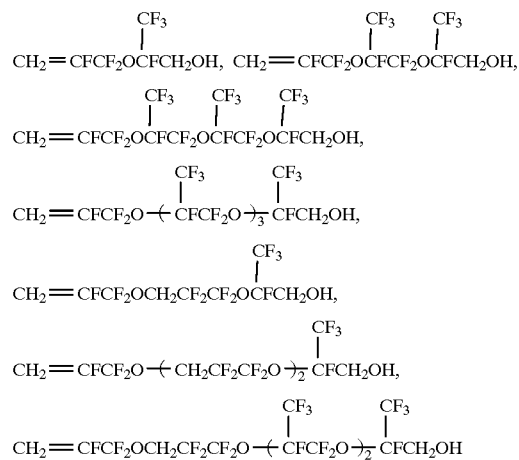

and the like.

The preferable examples of the fluorine-containing olefins represented by the formula (2-b) are

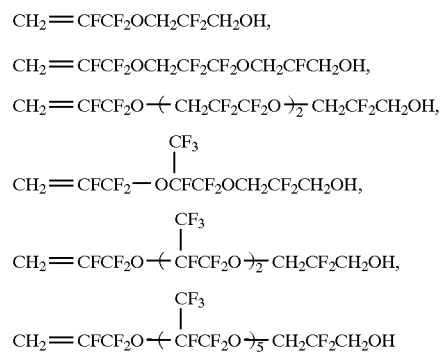

and the like.

The preferable examples of the fluorine-containing olefins represented by the formula (2-c) are

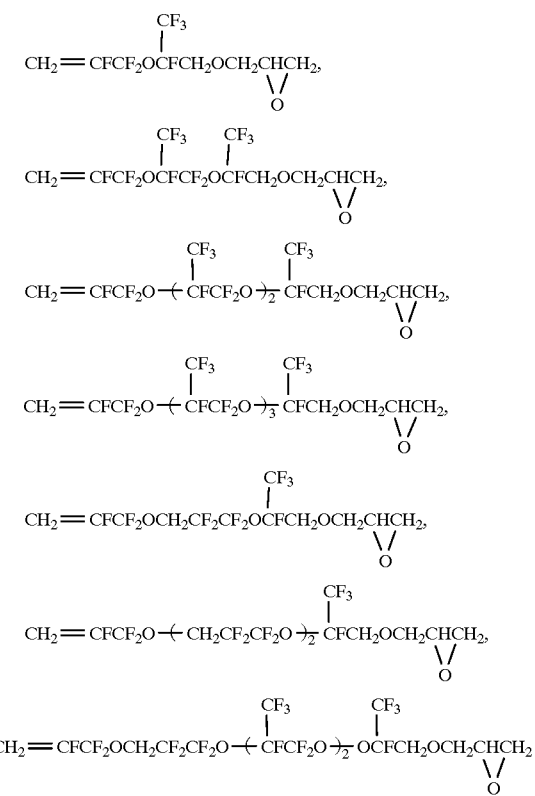

and the like.

The preferable examples of the fluorine-containing olefins represented by the formula (2-d) are

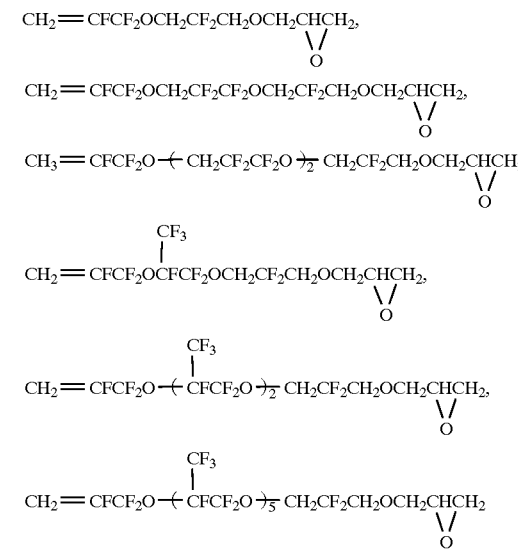

and the like.

The fluorine-containing olefin of the formula (2) can be derived from a corresponding acid fluoride prepared through the methods described in JP-A-137928/1985 and JP-A-12734/1987 or from a corresponding carboxylester prepared through the reaction of the above-mentioned acid fluoride and a lower alcohol. For example, the fluorine-containing olefin with hydroxyl group represented by the formula (2-a) can be synthesized by carrying out a reduction reaction, by using a reducing agent, of a methyl ester group in the fluorine-containing ether compound represented by the formula (2-e):

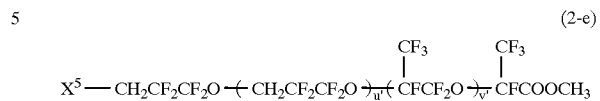

wherein $X^5$ is Br or I, u' is 0 or an integer of 1 to 5, v' is 0 or an integer of 1 to 10, and then a de-$X^5$F reaction ($X^5$ is Br or I) by using a metal such as zinc, or by carrying out previously the de-$X^5$F reaction to form a double bond and then acting thereto a reducing agent.

In the reduction reaction of the compound of the formula (2-e), there can be used usual reducing agents, for example, hydrogen (platinum oxide, palladium catalyst and the like are used), lithium aluminum hydride, boron hydride, sodium boron hydride, lithium boron hydride and the like, and sodium boron hydride is most preferable. The molar ratio of boron hydride to ester is from about 0.3 to about 1.2, preferably from about 0.4 to about 0.8. As the solvent, preferable are water, an alcohol type solvent such as methanol or ethanol, an ether type solvent such as ether, tetrahydrofuran, monoglyme, diglyme or dioxane, and a hydrocarbon type solvent such as pentane, hexane or cyclohexane. Among them, the alcohol type solvent is preferable, and ethanol is most preferable.

The reaction temperature is from −20° to 80° C. preferably from −10° to 20° C., and it is particularly preferable to carry out the reaction in the range of −5° to 10° C. from a point of decreasing by-products due to the hydrogenation of $X^5$—$CH_2$— ($X^5$ is Br or I) by a reducing agent and the reaction with $CH_2$=CF— bond. The reaction for forming a double bond through the de-$X^5$F reaction ($X^5$ is Br or I) from $X^5CH_2CF_2$— can be achieved in the same manner as in the above-mentioned reaction with Zn.

The fluorine-containing olefin with glycidyl group represented by the formula (2-c) can be synthesized through the reaction of epichlorohydrine and the corresponding fluorine-containing olefin with hydroxyl group of the formula (2-a). The synthesis is carried out in the same manner as in the above-mentioned preparation of the fluorine-containing olefin with glycidyl group of the formula (1-m) from the compound of the formula (1-h).

The fluorine-containing olefin with hydroxyl group represented by the formula (2-b) can also be derived from the corresponding carboxylester in the same manner.

That is, the compound (2-b) can be synthesized in the same manner as in synthesis of the fluorine-containing olefin of the formula (2-a) from the compound of the formula (2-e) except that the formula (2-f) is used.

wherein $X^6$ is Br or I, w' is 0 or an integer of 1 to 5, x' is 0 or an integer of 1 to 10.

Also the fluorine-containing olefin with glycidyl group represented by the formula (2-d) can also be synthesized through the reaction of the compound (2-b) and epichlorohydrine in the same manner as in the preparation of the compound (2-c).

The second fluorine-containing olefin with functional group of the present invention is a fluorine-containing olefin having carboxylic acid or a derivative thereof as a functional group and being represented by the formula (V)

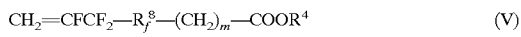

wherein $R^4$ is H, an alkyl group having 1 to 6 carbon atoms, Na, K, Li or $NH_4$, $R_f^8$ is a fluorine-substituted alkylene group having 3 to 40 carbon atoms or $-OR_f^9-$ ($R_f^9$ is a fluorine-substituted alkylene group having 2 to 40 carbon atoms or a fluorine-substituted ether group having 3 to 50 carbon atoms), m is 0 or an integer of 1 to 6.

One of the structures of $Rf^8$ in the fluorine-containing olefins of the formula (V) is a fluorine-substituted alkylene group having 3 to 40 carbon atoms, which includes linear form, branched form or mixed form thereof.

Among them, preferable typical examples are fluorine-containing olefins represented by the formula (3):

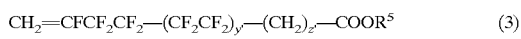

wherein $R^5$ and z' are the same as $R^4$ and m of the above-mentioned formula (V), respectively, y' is an integer of 1 to 10.

The preferable examples of the fluorine-containing olefins represented by the formula (3) are $CH_2=CFCF_2CF_2CF_2CF_2COOH$, $CH_2=CFCF_2CF_2(CF_2CF_2)_2-COOH$, $CH_2=CFCF_2CF_2(CF_2CF_2)_3-COOH$, $CH_2=CFCF_2CF_2CF_2CF_2CH_2COOH$, $CH_2=CFCF_2CF_2CF_2CF_2COOCH_3$, $CH_2=CFCF_2CF_2(CF_2CF_2)_2-COOCH_3$, $CH_2=CFCF_2CF_2CF_2CF_2COONa$, $CH_2=CFCF_2CF_2(CF_2CF_2)_2-COONa$, $CH_2=CFCF_2CF_2CF_2CF_2COONH_4$, $CH_2=CFCF_2CF_2(CF_2CF_2)_2-COONH_4$, and the like.

In case of the fluorine-containing olefin represented by the formula (3), for example, the fluorine-containing olefin with carboxyl group in which R is H, various synthesis methods can be employed. One of the methods is, for example, such that polyfluoroalkyliodide of the above-mentioned (1-e) and carbon dioxide gas are reacted in the presence of zinc powder in an amount of 2 equivalents or more to the raw material (1-e) for acid hydrolysis to give the fluorine-containing olefin.

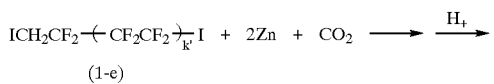

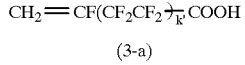

(k' is an integer of 2 or more)

The carbon dioxide gas can be supplied by bubbling at normal temperature or in an autoclave under pressure. As the solvents, preferable are dimethylformamide, dimethylacetamide, N-methylpyrrolidone, dimethyl sulfoxide and the like. Dimethylformamide and dimethylacetamide are particularly preferable. The reaction pressure is in the range of 0 to 50 kgf/cm²G, preferably 0 to 20 kgf/cm²G. The reaction temperature is from 0° to 150° C., preferably from 10° to 80° C.

Another method to synthesize the fluorine-containing olefin is a method in which oxidation of hydroxyl group of the compound of the above-mentioned formula (1-g) is carried out by using a usual oxidizing agent, followed by de-IF reaction by using Zn or the like.

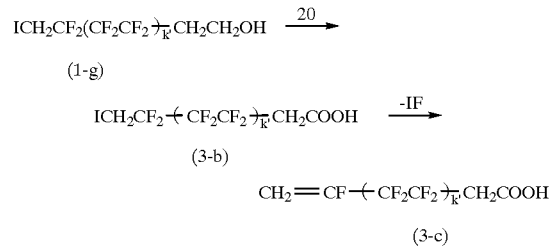

(k' is an integer of 2 or more)

As the oxidizing agents, there can be preferably used various ones, for example, a chromium type oxidizing agent such as a dichromate-sulfuric acid mixture or a chromium trioxide-pyridine mixture, a manganese type oxidizing agent such as manganese dioxide or potassium permanganate, silver oxide, nitric acid, an organic peroxide and the like, and particularly the dichromate-sulfuric acid mixture is preferable. The reaction temperature varies with the oxidizing agent to be used, and is usually from −20° to 150° C., preferably from −10° to 100° C., more preferably from −5° to 50° C. The fluorine-containing olefin (3-c) with carboxyl group can be prepared by using the obtained (3-b) and zinc in the same manner as mentioned above.

Another structure of $R_f^8$ in the fluorine-containing olefin of the formula (V) is an ether group represented by $-OR_f^9$, and $R_f^9$ is a fluorine-substituted alkylene group having 2 to 40 carbon atoms or a fluorine-containing ether group having 3 to 50 carbon atoms, and may be in the linear, branched or a mixture form.

Among them, the preferable typical examples are the fluorine-containing olefins represented by the formula (4):

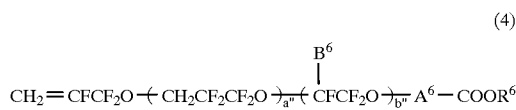

wherein $R^6$ is the same as $R^4$ of the formula (V), $A^6$ is

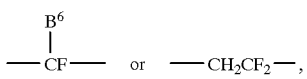

$B^6$ is $CF_3$ or F, a" is 0 or an integer of 1 to 5, b" is 0 or an integer of 1 to 10, $B^6$ is $CF_3$ in case of a"=b"=0.

Among the preferable examples of the formula (4), the fluorine-containing olefins with carboxyl group are

and the like.

The above-mentioned carboxylic acid derivative is an alkyl ester, sodium salt, potassium salt, lithium salt or ammonium salt of the above-mentioned carboxylic acids, and the preferable examples thereof are

-continued $CH_2=CFCF_2OCFCF_2OCFCOOCH_3$, (with CF₃ on each CF)

$CH_2=CFCF_2OCH_2CF_2COOCH_3$, $CH_2=CFCF_2OCH_2CF_2CF_2OCH_2CF_2COOCH_3$, $CH_2=CFCF_2O-(CFCF_2O)_2-CFCOOCH_3$ (with CF₃ substituents)

$CH_2=CFCF_2OCH_2CF_2CF_2OCFCF_2OCFCOOCH_3$ (with CF₃ substituents)

$CH_2=CFCF_2O-(CFCF_2O)_2-CH_2CF_2COOCH_3$ (with CF₃ substituent)

$CH_2=CFCF_2OCFCOONa$ (with CF₃)

$CH_2=CFCF_2OCFCF_2OCFCOONa$ (with CF₃ substituents)

$CH_2=CFCF_2OCH_2CF_2COONa$, $CH_2=CFCF_2OCH_2CF_2CF_2OCH_2CF_2COONa$, $CH_2=CFCF_2O-(CFCF_2O)_2-CFCOONa$ (with CF₃ substituents)

$CH_2=CFCF_2OCH_2CF_2CF_2OCFCF_2OCFCOONa$ (with CF₃ substituents)

$CH_2=CFCF_2O-(CFCF_2O)_2-CH_2CF_2COONa$ (with CF₃ substituent)

$CH_2=CFCF_2OCFCOONH_4$ (with CF₃)

$CH_2=CFCF_2OCFCF_2OCFCOONH_4$ (with CF₃ substituents)

$CH_2=CFCF_2OCH_2CF_2COONH_4$, $CH_2=CFCF_2OCH_2CF_2CF_2OCH_2CF_2COONH_4$, $CH_2=CFCF_2O-(CFCF_2O)_2-CFCOONH_4$ (with CF₃ substituents)

$CH_2=CFCF_2OCH_2CF_2CF_2OCFCF_2OCFCOONH_4$ (with CF₃ substituents)

$CH_2=CFCF_2O-(CFCF_2O)_2-CH_2CF_2COONH_4$ (with CF₃ substituent)

and the like.

There are various methods of synthesis of the carboxylic acid represented by the formula (4) and the derivative thereof, and they can be synthesized by using the above-mentioned formula (2-e) or (2-f) as a starting material.

$$X^5-CH_2CF_2CF_2O-(CH_2CF_2CF_2O)_{u'}-(CFCF_2O)_{v'}-CFCOOCH_3 \quad (2\text{-e})$$
(with CF₃ substituents)

($X^5$, u' and v' are the same as in (2-e).) $\xrightarrow{X^5F}$ $$CH_2=CFCF_2O-(CH_2CF_2CF_2O)_{u'}-(CFCF_2O)_{v'}-CFCOOCH_3 \quad (4\text{-a})$$
(with CF₃ substituents)

For example, the fluorine-containing olefin (4-a) with ester group can be prepared through the de-$X^5F$ reaction ($X^5$: I or Br) by using zinc in the same manner as mentioned above in case where the compound (2-e) is used.

The fluorine-containing olefin with carboxyl group can be prepared by the hydrolysis of the ester group of the compound (4-a) obtained through the above-mentioned de-$X^5F$ reaction ($X^5$: I, Br).

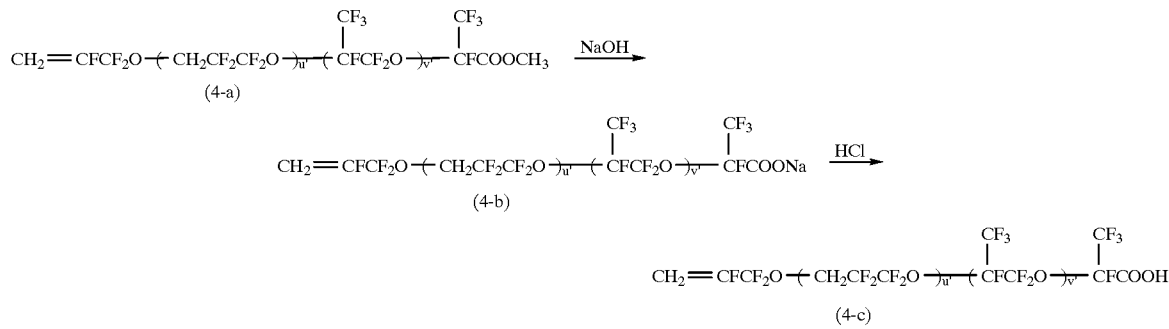

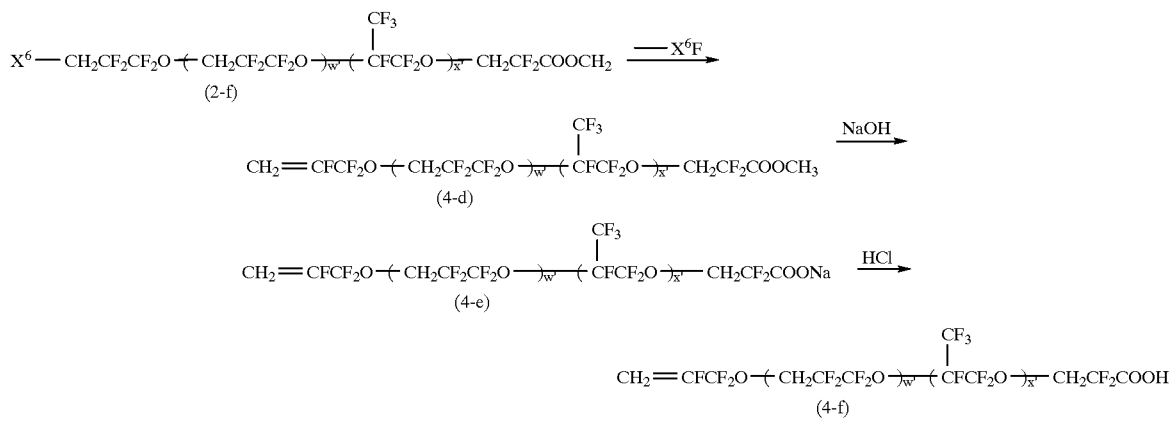

That is, the fluorine-containing olefin with carboxyl group can be prepared by reacting the fluorine-containing olefin (4-a) with an alkali hydroxide (MOH) such as sodium hydroxide to obtain the compound (4-b), and then applying thereto an inorganic protonic acid such as hydrochloric acid or sulfuric acid.

In the above-mentioned hydrolysis, there can be applied an inorganic protonic acid such as hydrochloric acid, sulfuric acid or nitric acid in addition to an alkali hydroxide such as sodium hydroxide, potassium hydroxide or lithium hydroxide.

In case of the alkali hydrolysis, the alkali hydroxide is used in a little excess equivalents, i.e. 1.0 to 1. 1 equivalent to the compound (4-a). As the solvent, water or an alcohol can be used, and methanol or ethanol is preferable. The reaction temperature is preferably from 50 to 150° C., more preferably from 10° to 50° C.

The fluorine-containing olefin (4-c) with carboxyl group can be obtained by adding an inorganic protonic acid (hydrochloric acid or sulfuric acid is preferable) to the solution of the obtained compound (4-b) until the solution becomes acid at pH of 2 or lower.

The sodium salt, potassium salt, lithium salt or ammonium salt of the carboxylic acid can be obtained by a usual method in which the obtained fluorine-containing olefin (4-c) with carboxyl group is neutralized by using an aqueous solution of sodium hydroxide, potassium hydroxide, lithium hydroxide or ammonia, respectively.

The corresponding fluorine-containing olefin (4-d) with carboxylester group, fluorine-containing olefin (4-f) with carboxyl group and their alkali metal salt or ammonium salt can be prepared similarly in the manner as mentioned below also in case where the formula (2-f) is used as a starting material.

The fluorine-containing olefin of the present invention is a useful compound which can introduce a reactive group such as hydroxyl group, carboxyl group and glycidyl group to a side chain of a fluorine-containing copolymer, and has the following characteristics:

(1) The polymerization rate is not decreased remarkably and excellent copolymerizability is assured at the time of copolymerization with various ethylenically unsaturated compounds, particularly ethylenically unsaturated fluorine-containing compound such as tetrafluoroethylene and vinylidene fluoride, (2) Thermal stability and chemical stability of the resulting fluorine-containing copolymer are not lowered, (3) The fluorine-containing olefin itself is stable under the alkaline condition, is not affected by the conditions in use and is easy to be handled, and (4) The process for synthesizing the fluorine-containing olefin is relatively easy and economical, and is industrially produceable.

Also there is a possibility that the fluorine-containing olefin itself is used as a macromer. The fluorine-containing compound having the structure such as carboxyl group, an alkali metal salt thereof or ammonium salt thereof generally has a high surface activity and is useful as an emulsifying agent. The fluorine-containing olefin with carboxyl group of the present invention, its Na, K, Li or ammonium salt is represented by the formula (5):

$$CH_2=CFCF_2R_f^{10}-(CH_2)_{d''}-COOR^7 \quad (5)$$

wherein $R^7$ is selected from H, Na, K and $NH_4$, d" is the same as m of the formula (V);

and $R_f^{10}$ in the structure is a fluorine-containing olefin of a long chain which comprises a fluorine-containing alkylene group having 3 to 40 carbon atoms or $-OR_f^{11}-(R_f^{11}$ is a fluorine-containing alkylene group having 2 to 50 carbon atoms or a fluorine-containing ether group having 3 to 50 carbon atoms). Namely, $R_f^{10}$ has 3 or more of carbon atoms, or in case that $R_f^{10}$ contains an ether bond, the sum of carbon atoms and oxygen atoms relating to the ether bond is 3 or more. As compared with a fluorine-containing olefin in which the number of carbon atoms of $R_f^{10}$ or the sum of carbon atoms and oxygen atoms relating to the ether bond of $R_f^{10}$ is 1 or 2, the above-mentioned long-chain fluorine-containing olefin has a high surface activity and is usable as a reactive emulsifying agent.

The use of the olefin, for example, in emulsion polymerization, contributes to making the emulsion particle size fine, increasing a yield and a reaction rate, and also making it possible to achieve soap-free polymerization.

Also, high contribution to dispersing stability of the emulsion obtained by emulsion polymerization is assured and it is possible to use no usual free emulsifying agent or decrease an amount thereof. Therefore it can be expected that the emulsion itself is used as a stable aqueous emulsion paint having a high weather resistance and high chemical resistance.

The second one of the present inventions relates to a fluorine-containing polymer with functional group, which is prepared by copolymerizing a fluorine-containing olefin (A) with any of hydroxyl group, glycidyl group, carboxyl group or carboxylester group and an ethylenically unsaturated compound (B).

As the prior arts relating to a fluorine-containing polymer with functional group, various copolymers of a fluorine-containing ethylenically unsaturated compound copolymerized with a hydrocarbon type monomer with functional group are reported.

For example, there are reported a copolymer of a hydroxyalkyl vinyl ether and tetrafluoroethylene (U.S. Pat. No. 3,306,879), a copolymer prepared by using glycidyl vinyl ether (JP-B-52645/1984) and a copolymer prepared by using a vinyl ether compound with carboxyl group (JP-A-110646/1989). With respect to these fluorine-containing polymers prepared by using such hydrocarbon type monomers with functional group, thermal resistance at both of their side chain and trunk chain portions is insufficient, and decomposition occurs on a part thereof particularly when melting and kneading with a heat-resisting thermoplastic resin at a high temperature. Thus desired external appearance and physical properties cannot be obtained.

On the other hand, as a fluorine-containing polymer prepared by using a fluorine containing olefin with functional group, there are known the fluorine-containing polymers (JP-A-143888/1975) prepared by using

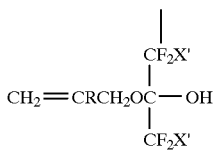

wherein R is H or methyl, X' is F or Cλ, and hemi-acetal. Those polymers, however, have tertiary hydrogen like

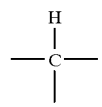

in the trunk chain, and thus there are drawbacks such that thermal resistance of the obtained copolymer is decreased to easily cause coloring and deterioration at a high temperature.

Also as a fluorine-containing polymer prepared by copolymerizing a monomer having a perfluorovinyl group, there are reported a fluorine-containing polymer prepared by using a fluorine-containing monomer represented by $CF_2=CF(CF_2)_\alpha-(CH_2)_\beta-X$, wherein X is OH,

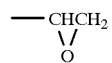

or —COOH (JP-A-675 17/1985), and fluorine-containing polymers prepared by copolymerizing the respective fluorine-containing monomers of $CF_2=CFO-R_f-COOH$ (JP-A-234753/1991) and $CF_2=CFOR_{f'}-CH_2OH$ (JP-A-91513/1991, JP-A-503935/1993). The reactivity of polymerization of these monomers having the perfluorovinyl group with ethylene, tetrafluoroethylene, chlorotrifluoroethylene and the like is low, and in order to obtain a polymer having a desired composition, a large amount of monomers is required. Also a rate of copolymerization decreases remarkably.

Further these monomers require complicated synthesizing process steps and are expensive, and thus are industrially less practical.

Also there is a report such that a fluorine-containing polymer with functional group is prepared by dehydrofluorination of a vinylidene fluoride type polymer and addition of a nucleophilic functional group to the formed double bond (Polym Mater. Sci Eng., 49,518 (1983), JP-A-112616/1993). The fluorine-containing polymers obtained through the above-mentioned polymer reaction have such problems that the functional groups are difficult to be uniformly introduced thereto and an irregular distribution of composition occurs, and that the side chain portion of the prepared polymer is insufficient in thermal resistance and chemical resistance due to the addition of the nucleophilic reactive reagent, and that the polymers are limited to only the vinylidene fluoride type polymers.

An object of the present invention is to solve the above-mentioned problems and to provide a novel fluorine-containing polymer in which a useful functional group such as hydroxyl group, glycidyl group or carboxyl group is introduced without impairing excellent thermal resistance, chemical resistance and the like which the fluorine-containing resin possesses.

The present invention particularly relates to a fluorine-containing polymer with functional group, which is characterized in that the polymer itself has enough thermal resistance to melting and kneading at a high temperature when blended with a heat-resisting thermoplastic resin, and further in that a homogeneous dispersion can be formed since the fluorine-containing polymer and the thermoplastic resin have a good affinity with each other in the obtained blend.

The present invention relates to a novel fluorine-containing polymer with functional group which is a copolymer comprising 0.01 to 80% by mole of (A) and 20 to 99.99% by mole of (B) and having a number average molecular weight of 2,000 to 20,000,000.

The compound (A) comprises one or more monomers represented by the formula (I):

$$CH_2=CFCF_2-R_f^1-(CH_2)_a-X^1 \qquad (I)$$

wherein $X^1$ is —$CH_2OH$, —$COOR^1$ ($R^1$ is H, an alkyl group having 1 to 6 carbon atoms, Na, K, Li or $NH_4$),

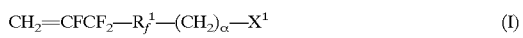

$R_f^1$ is a fluorine-substituted alkylene group having 1 to 40 carbon atoms or —$OR_f^2$ ($R_f^2$ is a fluorine-substituted alkylene group having 1 to 40 carbon atoms or a fluorine-substituted ether group having 3 to 50 carbon atoms), a is 0 or an integer of 1 to 6, and the compound (B) comprises one or more monomers selected from the group consisting of the monomers represented by the formula (II):

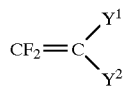

wherein $Y^1$ is F, Cλ, H or $CF_3$, $Y^2$ is F, Cλ, H, $R_f^3$ ($R_f^3$ is a perfluoroalkyl group having 1 to 10 carbon atoms) or

($R_f^4$ is a perfluoroalkyl group having 1 to 6 carbon atoms, b is 0 or an integer of 1 to 5) and the formula (III):

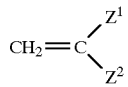

wherein $Z^1$ is F, H, an alkyl group having 1 to 6 carbon atoms or a perfluoroalkyl group having 1 to 10 carbon atoms, $Z^2$ is H, Cλ, an alkyl group having 1 to 6 carbon atoms or —$(CF_2)_d-Z^3$ (d is an integer of 1 to 10, $Z^3$ is F or H).

That is, the polymer of the present invention is a novel fluorine-containing polymer with functional group, which is prepared by copolymerizing 0.01 to 80% by mole of a fluorine-containing olefin (A) of the specific structure represented by the formula (I) having any functional group of hydroxyl group, carboxyl group, carboxylic acid derivative, glycidyl group or glycidyl ether group with the ethylenically unsaturated compound (B).

In the fluorine-containing polymer of the present invention, the fluorine-containing olefin (A) with functional group is one represented by the formula (I), and the polymer prepared by copolymerizing the olefin having $X^1$, as a functional group, such as —$CH_2OH$, —$COOH$,

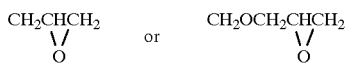

is preferable. In the compound (A), $R_f^1$ is the fluorine-containing alkylene group or the fluorine-containing oxyalkylene group represented by —$OR_f^2$, and $R_f^2$ is the fluorine-containing alkylene group or the fluorine-containing ether group. Particularly in case where importance is attached to thermal resistance, it is preferable that $R_f^1$ is more highly fluorine-substituted, and a perfluorinated alkylene group or oxyalkylene group is preferable. Also, with respect to a carbon chain length of $R_f^1$, about 1 to about 40 carbon atoms can be used depending on uses, and it is preferable that $R_f^1$ has about 2 to about 20 carbon atoms from the viewpoints of reactivity of polymerization and physical properties of the copolymer.

The preferable examples of $R_f^1$ are

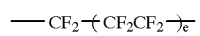

(e is 0 or an integer of 1 to 10),

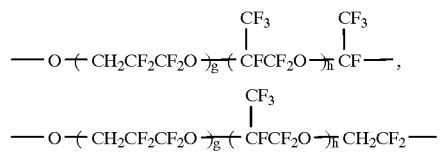

(g is 0 or an integer of 1 to 5, h is 0 or an integer of 1 to 10) and the like.

Further as the examples of the compound (A) in which $X^1$ is —$CH_2OH$, preferable are

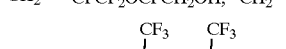

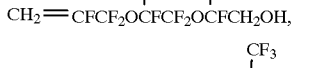

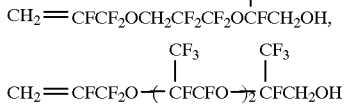

and the like, and particularly preferable are

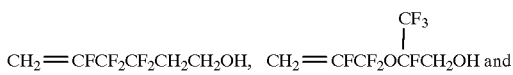

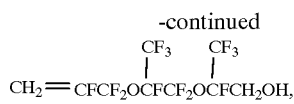

As the compounds in which $X^1$ is —COOH group, preferable are

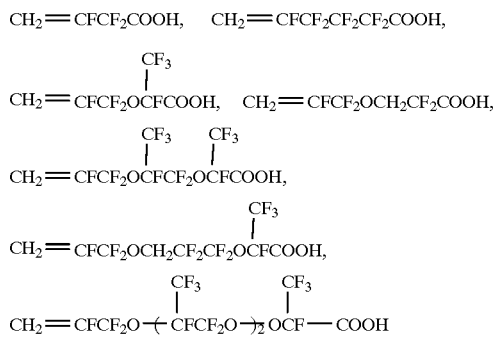

and the like, and particularly preferable are

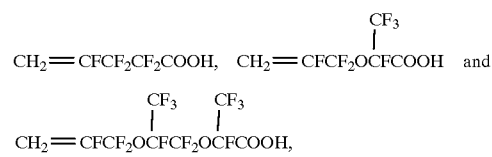

As the compounds in which $X^1$ is a carboxylic acid derivative, preferable are

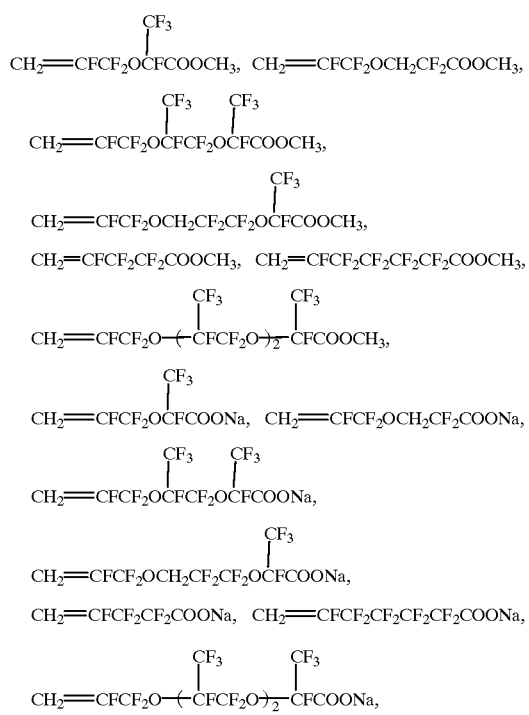

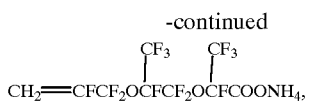

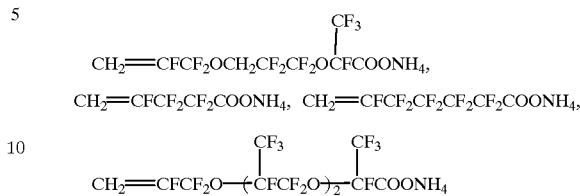

and the like.

As the compounds in which $X^1$ is

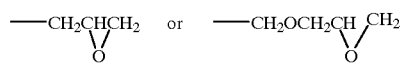

preferable are

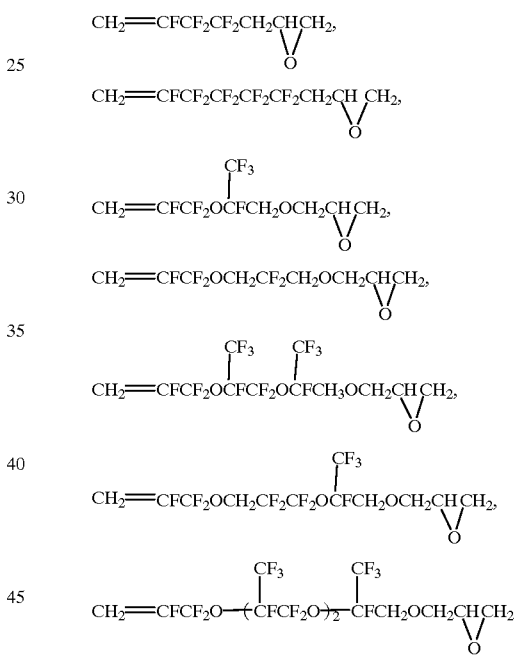

and the like, and particularly preferable are

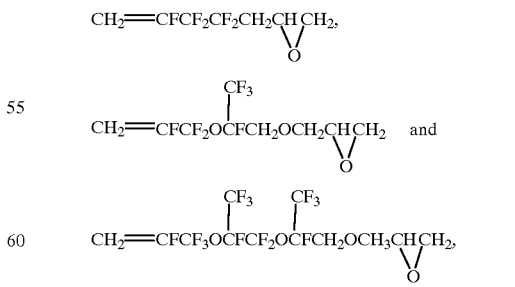

Another copolymerizing component (B) of the polymer of the present invention comprises one or more monomers selected from the group consisting of the monomers represented by the formula (II):

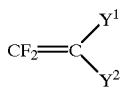 (II)

wherein $Y^1$ is F, Cλ, H or $CF_3$, $Y^2$ is F, Cλ, H, $R_f^3$ ($R_f^3$ is a perfluoroalkyl group having 1 to 10 carbon atoms) or

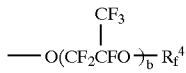

($R_f^4$ is a perfluoroalkyl group having 1 to 6 carbon atoms, b is 0 or an integer of 1 to 5) and the formula (III):

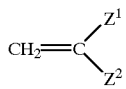 (III)

wherein $Z^1$ is F, H, an alkyl group having 1 to 6 carbon atoms or a perfluoroalkyl group having 1 to 10 carbon atoms, $Z^2$ is H, Cλ, an alkyl group having 1 to 6 carbon atoms or $-(CF_2)_d-Z^3$ (d is an integer of 1 to 10, $Z^3$ is F or H).

As the examples of the monomers represented by the formula (II), preferable are
$CF_2=CF_2$, $CF_2=CFCl$, $CF_2=CFCF_3$, $CF_2=CH_2$, $CF_2=C(CF_3)_2$, $CF_2-CFOCF_3$, $CF_2=CFOC_3F_7$,

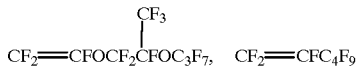

and the like.

As the examples of the monomers represented by the formula (III), preferable are
$CH_2=CHF$, $CH_2=CFCF_3$, $CH_2=CHCF_3$, $CH_2=C(CF_3)_2$, $CH_2=CH_2$, $CH_2=CHCH_3$, $CH_2=CHC_2H_5$, $CH_2=C(CH_3)_2$, $CH_2=CHCl$, $CH_2=CHC_4F_9$, $CH_2=CF(CF_2)_3-H$ and the like.

The molar ratio of the fluorine-containing olefin (A) with functional group to the other monomer (B) in the fluorine-containing polymer of the present invention may vary depending on use and kind of copolyemrs, and is usually (A)/(B)=0.01 to 80/99.99 to 20% by mole. Particularly the proportion of (A)/(B)=0.01 to 30/99.99 to 70% by mole is preferable in order to obtain a composition having an excellent dispersibility when mixing with the heat-resisting thermoplastic resin.

Further in the fluorine-containing polymer of the present invention, in addition to the above-mentioned compounds (A) and (B), an ethylenically unsaturated compound (C) which is copolymerizable with the compounds (A) and (B) may be copolymerized.

As the above-mentioned ethylenically unsaturated compounds, there are alkyl vinyl ethers or vinyl esters represented by the formula:

$CH_2=CH-O-(C=O)_{e''}R^8$ wherein $R^8$ is an aliphatic group having 1 to 17 carbon atoms, an alicyclic group having 3 to 17 carbon atoms or a fluoroalkyl group having 1 to 20 carbon atoms, e" is 0 or 1, and examples thereof are, for instance, methyl vinyl ether, ethyl vinyl ether, n-propyl vinyl ether, isopropyl vinyl ether, n-butyl vinyl ether, isobutyl vinyl ether, cyclohexyl vinyl ether, 2,2,2-trifluoroethyl vinyl ether, 2,2,3,3-tetrafluoropropyl vinyl ether, 2,2,3,3,3-pentafluoropropyl vinyl ether, vinyl acetate, vinyl propionate, vinyl butyrate, vinyl pivalate, vinyl versatate, vinyl cyclohexanedicarboxylate and the like.

Further there are compounds represented by the formula:

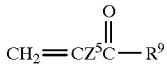

wherein $Z^5$ is H, Cλ, F, $CH_3$ or $CF_3$, $R^9$ is H, Cλ, F, an aliphatic group having 1 to 17 carbon atoms, an alicyclic group having 3 to 17 carbon atoms or a fluoroalkyl group having 1 to 20 carbon atoms. As the examples thereof, there are, for instance, isobutyl acrylate, methyl acrylate, ethyl methacrylate, 2,2,3,3,3-pentafluoropropyl α-fluoroacrylate, 2,2,3,3,4,4,5,5,6,6,7,7-dodecafluoropentyl α-trifluoromethylacrylate, cyclohexyl acrylate, 2,2,3,3,4,4,5,5,6,6,7,7,8,8,9,9,10,10,11,11,12,12,13,13,14,14,15,15,15-nonacosafluoropentadecyl acrylate, octyl α-chloroacrylate, octadecyl acrylate and the like.

Also, the compounds represented by the formula:

$CH_2=CHCH_2Z^6$ wherein $Z^6$ is chlorine atom or an alkoxyl group having 1 to 8 carbon atoms can be used, and the examples thereof are, for instance, allyl chloride, allyl methyl ether, allyl isopropyl ether, allyl octyl ether and the like.

In addition, there are styrene, styrene derivatives, dialkyl esters of maleic acid and the like.

In case where the ethylenically unsaturated compound (C) is copolymerized, the molar ratio of each monomer in the polymer varies depending on use and kind of the copolymers, and (A)/((B)+(C)) is usually 0.01 to 80/99.99 to 20% by mole. With respect to (B) and (C), it is preferable that (C) is not more than 60% by mole per the sum of (B) and (C). Particularly in case of the fluorine-containing polymer to be used when mixing with a heat-resisting thermoplastic resin, since the portion from the compound (C) may be most thermally instable, it is preferable that (A), (B) and (C) are 0.01 to 30% by mole, 70 to 99.99% by mole and not more than 20% by mole, respectively to the total moles of all monomers.

In the fluorine-containing polymers of the present invention, the performances, physical properties and uses complying therewith depend largely on the kind and proportion (ratio) of the compound (B).

As the preferable structure of the fluorine-containing polymer of the present invention, the compound (B) is roughly classified into two groups. One group mainly comprises tetrafluoroethylene or chlorotrifluoroethylene, and another group mainly comprises vinylidene fluoride. That is, the first group is a fluorine-containing polymer which is prepared by copolymerizing a fluorine-containing olefin (A) with functional group and the compound (B) which essentially contains tetrafluoroethylene or chlorotrifluoroethylene, and, if necessary, other copolymerizable monomers. The fluorine-containing polymer comprises 0.01 to 30% by mole of (A) on the basis of the total moles of all monomers and not less than 30% by mole of tetrafluoroethylene or chlorotrifluoroethylene per the total moles of the monomers excepting the fluorine-containing olefin (A).

As the other copolymerizable monomers in the above-mentioned polymer, preferable are vinylidene fluoride, hexafluoropropene, hexafluoroisobutene, a perfluoro vinyl ether represented by the formula:

wherein $R_f^5$ is a perfluoroalkyl having 1 to 6 carbon atoms, j is 0 or an integer of 1 to 5, a fluorine-containing olefin represented by the formula:

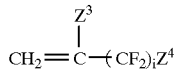

wherein $Z^3$ is H or F, $Z^4$ is H or F, i is an integer of 1 to 10, and ethylene, propylene, 1-butene, isobutene and the like.

As the specific examples of the fluorine-containing polymer of the present invention which mainly comprises tetrafluoroethylene or chlorotrifluoroethylene, there are preferably, for instance, a copolymer of the fluorine-containing olefin (A) and tetrafluoroethylene (so-called PTFE with functional group); a copolymer of the compound (A), tetrafluoroethylene and hexafluoropropene (FEP with functional group); a copolymer of the compound (A), tetrafluoroethylene and the above-mentioned perfluoro(vinyl ether) in an amount of not more than 10% by mole per all monomers excepting (A) (PFA with functional group); a copolymer of the compound (A), tetrafluoroethylene or chlorotrifluoroethylene, ethylene and further a copolymerizable fluorine-containing olefin as a third monomer if necessary (E(C)TFE with functional group); an elastomeric copolymer of the compound (A), tetrafluoroethylene and propylene; an elastomeric copolymer of the compound (A), tetrafluoroethylene and a perfluoro (vinyl ether) in an amount of not less than 15% by mole per all the monomers excepting (A); and the like.

Particularly when the fluorine-containing polymer is blended with a heat-resisting thermoplastic resin, though it varies depending on kind of the heat-resisting thermoplastic resin, a processing temperature relatively equivalent to that of the heat-resisting thermoplastic resin can be selected in melt-blending and molding, and a fluorine-containing polymer of which thermal stability is maintained at the processing temperature is preferable. Among the above-mentioned examples, particularly preferable are the PFA type copolymer comprising the compound (A), and also the E(C)TFE type copolymer and the elastomeric copolymer containing the compound (A) and mainly comprising tetrafluoroethylene.

Among them, the PFA type copolymer is one particularly comprising 0.01 to 30% by mole of the fluorine-containing olefin (A) with functional group per the total moles of all monomers, 95 to 99.7% by mole of tetrafluoroethylene per the total moles of the monomers excepting the compound (A) and 0.3 to 5.0% by mole of a perfluoro(vinyl ether) represented by the formula:

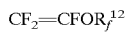

wherein $R_f^{12}$ is a perfluoroalkyl group having 1 to 6 carbon atoms per the total moles of the monomers excepting the compound (A).

Also the E(C)TFE type copolymer is particularly one comprising 0.01 to 30% by mole of the fluorine-containing olefin (A) with functional group per the total moles of all the monomers, 30 to 70% by mole of tetrafluoroethylene per the total moles of the monomers excepting the compound (A), 30 to 70% by mole of ethylene and 0 to 15% by mole of the fluorine-containing olefin as a third component if necessary. As the fluorine-containing olefin as the third component, there can be used a fluorine-containing olefin represented by

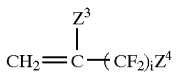

wherein $Z^3$ is H or F, $Z^4$ is H or F, i is an integer of 1 to 10, perfluoro(vinyl ether), hexafluoropropylene, hexafluoroisobutylene and the like, and

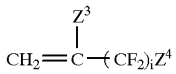

($Z^3$, $Z^4$ and i are the same as above) and hexafluoroisobutylene are particularly preferable.

On the other hand, as the elastomeric copolymer with functional group and mainly comprising tetrafluoroethylene, there is one comprising 0.01 to 30% by mole of the fluorine-containing olefin (A) with functional group per the total moles of all monomers and 40 to 70% by mole of tetrafluoroethylene and 30 to 60% by mole of propylene per the total moles of the monomers excepting the compound (A). Also it is possible that additionally the copolymerizable components such as vinylidene fluoride, hexafluoropropylene, chlorotrifluoroethylene and perfluoro (vinyl ether) may be contained in an amount of not more than 20% by mole per the total moles of the monomers excepting the compound (A).

Another elastomeric polymer is a polymer of tetrafluoroethylene and perfluoro(vinyl ether), and comprises 0.01 to 30% by mole of the compound (A) per the total moles of all monomers and 40 to 85% by mole of tetrafluoroethylene on the basis of all the monomers excepting the compound (A) and 15 to 60% by mole of a perfluoro(vinyl ether) represented by the formula:

wherein $R_f^5$ is a perfluoroalkyl group having 1 to 6 carbon atoms, j is 0 or an integer of 1 to 5.

The second group of the preferable fluorine-containing polymer of the present invention is a polymer mainly comprising vinylidene fluoride.

That is, the polymer is a copolymer prepared by copolymerizing the fluorine-containing olefin (A) with functional group and the compound (B) containing essentially vinylidene fluoride, and, if necessary, other monomers. This fluorine-containing polymer comprises 0.01 to 30% by mole of the compound (A) per the total moles of all monomers and not less than 40% by mole of vinylidene fluoride per the total moles of the monomers excepting the compound (A).

As the other copolymerizable monomers in the above-mentioned polymer, the preferable examples are tetrafluoroethylene, chlorotrifluoroethylene, hexafluoropropene, hexafluoroisobutene, perfluoro(vinyl ether) and the like.

As the preferable examples of the fluorine-containing polymer of the present invention, which mainly comprises vinylidene fluoride, there are a copolymer of the fluorine-containing olefin (A) with functional group and vinylidene fluoride (so-called PVdF with functional group), a copolymer of the compound (A), vinylidene fluoride and tetrafluoroethylene, a copolymer of the compound (A), vinylidene fluoride and hexafluoropropylene, a copolymer of the compound (A), vinylidene fluoride, tetrafluoroethylene and hexafluoropropylene, a copolymer of the compound (A), vinylidene fluoride, tetrafluoroethylene and chlorotrifluoroethylene, and the like.

Further these fluorine-containing polymers mainly comprising vinylidene fluoride can be made resinous or elastomeric polymers by the presence or absence of other copolymerizable monomer component and by selecting kind and proportion thereof.

Among them, particularly preferable examples of resinous polymers for blending with a heat-resisting thermoplastic resin are a copolymer comprising 0.01 to 30% by mole of the fluorine-containing olefin (A) with functional group and 70 to 99.9% by mole of vinylidene fluoride, a copolymer comprising 0.01 to 30% by mole of the compound (A) per the total moles of all monomers, and, per the total moles of the monomers excepting the compound (A), 70 to 99% by mole of vinylidene fluoride and 1 to 30% by mole of tetrafluoroethylene, a copolymer comprising 0.01 to 30% by mole of the compound (A) per the total moles of all monomers and, per the total moles of the monomers excepting the compound (A), 50 to 99% by mole of vinylidene fluoride, 0 to 30% by mole of tetrafluoroethylene and 1 to 20% by mole of chlorotrifluoroethylene, a copolymer comprising 0.01 to 30% by mole of the compound (A) on the basis of all monomers and, per the total moles of the monomers excepting the compound (A), 60 to 99% by mole of vinylidene fluoride, 0 to 30% by mole of tetrafluoroethylene and 1 to 10% by mole of hexafluoropropylene, and the like.

Also preferable example of the composition where the prepared polymer is in the form of elastomer is a copolymer comprising 0.01 to 30% by mole of the compound (A) per the total moles of all monomers and, per the total moles of the monomers excepting the compound (A), 40 to 90% by mole of vinylidene fluoride, 0 to 30% by mole of tetrafluoroethylene and 10 to 50% by mole of hexafluoropropylene.

Examples of the fluorine-containing polymer of the present invention include a segmented fluorine-containing polymer with functional group obtained by copolymerizing a fluorine-containing olefin (A) with functional group when preparing a segmented fluorine-containing polymer as described in JP-B-49327/1986.

That is, the segmented fluorine-containing polymer basically comprises, as the essential components, iodine atom released from an iodide compound which has iodine atom bonded to carbon atom, a residue of the iodide compound excluding the iodine atom and at least two polymer chain segments which are present among the iodine atoms and the residues (at least one of the segments is a fluorine-containing polymer chain segment). Namely, the segmented fluorine-containing polymer of the present invention basically comprises, as the essential components, a sequential chain comprising at least 2 polymer chain segments (at least one of them is a fluorine-containing polymer chain segment); iodine atom released from an iodide compound having iodine atom bonded to carbon atom present at one end of the sequential chain; and a residue of the iodide compound after releasing the iodine atom at the other end. That is, the typical structure of the segmented fluorine-containing polymer of the present invention is represented by the following formula:

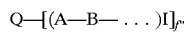

wherein Q is a residue of an iodide compound after releasing an iodine atom, A, B, . . . are polymer chain segments (at least one of them is a fluorine-containing polymer chain segment), I is iodine atom released from the above-mentioned iodide compound, f" is the number of bonds of Q.

The segmented fluorine-containing polymer with functional group prepared by copolymerizing the fluorine-containing olefin (A) with functional group of the present invention is a fluorine-containing copolymer wherein the fluorine-containing olefin (A) with functional group is introduced through copolymerization to any one of two segments (or three segments) in the polymer or both segments (two or more segments).

The preferable range of the molecular weight of the fluorine-containing polymer of the present invention changes depending on kinds, uses and methods of use of the polymer, and are not limited particularly. For example, for application to molding, generally too low molecular weight is not preferable from the viewpoint of mechanical strength of the fluorine-containing polymer or a blended composition of the polymer and a heat-resisting thermoplastic resin. Preferable number average molecular weight is usually not less than 2,000, particularly not less than about 5,000. Also from the viewpoint of moldability, too high molecular weight is not preferable. Preferable molecular weight is usually not more than 1,000,000, particularly not more than about 750,000.

Among the examples of the fluorine-containing polymers of the present invention, in case of resinous copolymers which mainly comprise the above-mentioned tetrafluoroethylene, for example, melt-processable fluorine-containing polymers such as PFA, FEP and ETFE types comprising the fluorine-containing olefin (A) with functional group, their melt flow rates are from $0.01 \times 10^{-2}$ to $50 \times 10^{-2}$ m$\lambda$/sec., preferably from $0.05 \times 10^{-2}$ to $25 \times 10^{-2}$ m$\lambda$/sec., particularly preferably from $0.1 \times 10^{-2}$ to $10 \times 10^{-2}$ m$\lambda$/sec. at the determined measuring temperature (for example, 372° C. in PFA and FEP type polymers and 300° C. in ETFE type polymer) and load (for example, 7 kg) depending on kind of the respective fluorine-containing resins.

Also among the above-mentioned examples of the polymers of the present invention, the number average molecular weight measured by GPC analysis by calibration based on polystyrene is from 2,000 to 1,000,000, preferably from 5,000 to 750,000, particularly preferably from 10,000 to 500,000 in case of fluorine-containing polymers soluble in a solvent such as DMF or THF, e.g. an elastomeric polymer containing the compound (A) and mainly comprising tetrafluoroethylene, a copolymer of the compound (A) and vinylidene fluoride, and a resinous or elastomeric polymer comprising the compound (A), vinylidene fluoride, and further one or more of tetrafluoroethylene, hexafluoroethylene and chlorotrifluoroethylene.

Also, for example, in case of a copolymer of the compound (A) and tetrafluoroethylene, the copolymer includes an oligomer-like polymer, a polymer so-called as a low molecular weight PTFE having a molecular weight of about 2,000 to about 1,000,000 and in addition, a high molecular weight polymer which is not melt-processable.

In case of the high molecular weight polymer, though the molecular weight cannot be specified, it is from about 1,000,000 to 10,000,000 and about 20,000,000 at maximum.

The fluorine-containing polymer of the present invention can be prepared in any polymerization method such as suspension polymerization, emulsion polymerization, solution polymerization and bulk polymerization. The method of polymerization can be properly selected depending on mainly kind and use of the polymers.

In case where the copolymer of the present invention is prepared by the suspension polymerization, the oil-soluble initiator to be used for radical polymerization may be one usually used, and there are, for example, organic peroxides such as diisopropyl peroxydicarbonate, di-n-propyl peroxydicarbonate and isobutylperoxide; and peroxides represented by the formula:

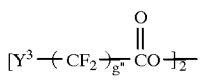

wherein $Y^3$ is hydrogen atom, fluorine atom or chlorine atom, g" is an integer of 2 to 8. Examples thereof are diperfluoropropionyl peroxide, di($\omega$-hydroperfluorohexanoyl) peroxide, di($\omega$-chloroperfluoropropionyl) peroxide and the like. Also there are peroxides represented by the formula:

wherein h" is an integer of 1 to 10, for example, fluorine type organic peroxides such as di(trichloroperfluorohexanoyl) peroxide and azo-compounds such as azobisisobutyronitrile.

As the polymerization solvents, there are, for example, water, a chlorofluoroalkane and the like, and a mixture of water and the chlorofluoroalkane is preferable.

It is particularly preferable that the chlorofluoroalkane is from 10 to 100% by weight based on water from the viewpoints of suspension dispersibility and economy.

It is preferable to use a chlorofluoroalkane having 1 to about 4 carbon atoms. For example, there are fluoromethanes such as dichlorodifluoromethane, dichloromonofluoromethane, monochlorodifluoromethane, monochlorotrifluoromethane and tetrafluoromethane; fluoroethanes such as tetrafluoroethane, trichlorotrifluoroethane, dichlorotetrafluoroethane and hexafluoroethane; fluoropropanes such as dichloropentafluoropropane; fluorobutanes such as perfluorocyclobutane; and the like. Among them, dichlorotetrafluoroethane, trichlorotrifluoroethane, dichloropentafluoropropane and perfluorocyclobutane are preferably used.

Also as a chain transfer agent, if necessary for molecular weight control, there can be used isopentane, n-hexane, cyclohexane, methanol, ethanol, tert-butanol, carbon tetrachloride, chloroform, methylene chloride, methyl chloride, a fluorocarbon iodide (such as $CF_2I_2$, $CF_3I$, I—$(CF_2)_4$—I or $(CF_3)_2CFI$) and the like.

As an initiator to be used in case of preparing the polymers of the present invention through the emulsion polymerization, usual radical initiators can be used. A water-soluble initiator is used preferably, and examples are a persulfuric acid such as ammonium persulfate salt, a redox initiator which comprises hydrogen peroxide or a combination thereof with a reducing agent such as sodium hydrogensulfite or sodium thiosulfate; an inorganic initiator in which a trace amount of iron, ferrous salt, silver sulfate and the like are coexistent with the redox initiator; a dibasic acid peroxide such as succinyl peroxide or glutaryl peroxide; azobisisobutylamidine dihydrochloric acid; and the like. Also the above-mentioned oil-soluble initiators can be used similarly.

As an emulsifying agent, a fluorocarbon type emulsifying agent is preferably used, and the preferable examples thereof are ammonium perfluorooctanoate, ammonium perfluorononanoate, an ether type fluorine-containing emulsifying agent represented by the formula:

 (i" = an integer of 1 to 5)

and the like. Also, if necessary, a hydrocarbon type anion surfactant, cation surfactant, nonion surfactant and betaine surfactant can be used.

Further if necessary, a chain transfer agent similar to one mentioned above, a pH buffer agent, a pH control agent can also be used.

In case where the polymers of the present invention are prepared by the solution polymerization, as the polymerizing solvent, in addition to the above-mentioned chlorofluoroalkanes, there can be used ketones such as acetone, methyl ethyl ketone and methyl isobutyl ketone; esters such as ethyl acetate and butyl acetate; aromatic hydrocarbons such as toluene and xylene; alcohols such as methanol, ethanol and isopropanol; glycol ethers such as ethyl cellosolve, monoglyme and diglyme; and the like.

As a polymerization initiator and a chain transfer agent, ones similar to those for the suspension polymerization can be used.

The conditions for polymerization of the polymer of the present invention are properly selected depending on kind and composition of the polymer, reaction method, initiator, reaction medium and the like. The reaction temperature is usually from −20° to 150° C., preferably from 5° to 100° C., and the polymerization pressure is not more than 100 kgf/cm$^2$G, preferably not more than 50 kgf/cm$^2$G.

In preparing the polymer of the present invention, the method for charging a polymerization tank with each component (particularly monomers, an initiator and a chain transfer agent) is not particularly limited.

A polymerization tank may be initially charged with a whole amount of each component to be used at the same time, or may be charged in turns with a part or the whole of the components continuously or dividedly.

The fluorine-containing polymer of the present invention can be effectively used for applications which require thermal resistance, chemical resistance, weather resistance, oil resistance, solvent resistance and the like as a usual molding material, paint, rubber, adhesive, ion exchange membrane, sealant and the like, in addition to the use for blending with a heat-resisting thermoplastic resin.

Concretely, the polymer of the present invention can be applied to the following uses, by utilizing the functional group thereof.

① Among the fluorine-containing monomers (A) with functional group, one having hydroxyl group or carboxyl group is introduced into the fluorine-containing resins such as so-called PTFE, FEP, PFA and ETFE to give a modified PTFE, modified FEP, modified PFA and modified ETFE. These polymers can be cross-linked without adding a cross-linking agent by heat-treating at a temperature of not less than 200° C. for at least one hour, and can provide molded articles which have a high modulus of elasticity and do not flow even at a temperature of not less than their melting point.

In that case, an amount of a fluorine-containing olefin with hydroxyl group or carboxyl group in the fluorine-containing polymer is from 0.1 to 20% by mole. If the concentration of the functional groups is too low, cross-linking is not sufficient and it becomes difficult to obtain a high modulus of elasticity without using a cross-linking agent. On the other hand, if it is too high, a melting point of the fluorine-containing polymer becomes lowered, and accurate molding becomes difficult because it is difficult to maintain the shape of the polymer during the heat-treatment. Internal strain is easy to occur at the time of heat-treatment and thus cracking easily occurs. Also it is not preferable because there occur problems such that the fluorine-containing copolymer becomes in the form of elastomer and moldability lowers. It is particularly preferable that the polymer contains the fluorine-containing olefin with hydroxyl group or carboxyl group in a proportion of 0.2 to 10% by mole.

② A fluorine-containing polymer prepared by introducing the fluorine-containing olefin (A) into a copolymer of tetrafluoroethylene or chlorotrifluoroethylene and an alkyl vinyl ether or alkyl vinyl ester represented by the formula:

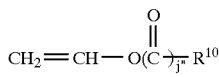

wherein $R^{10}$ is an aliphatic group having 1 to 17 carbon atoms, an alicyclic group having 3 to 17 carbon atoms or a fluoroalkylene group having 1 to 20 carbon atoms, j" is 0 or 1, or a vinylidene fluoride type polymer with functional group can be a resin for paints which is excellent in weather resistance, chemical resistance and antisoil property.

In case where these fluorine-containing resins are used as the paint, there are the following effects of the functional group.

i) It is possible to add a curing agent being capable of reacting with the functional group of the present invention and to conduct a cross-linking reaction at normal temperature or with heating. That is, the resin is particularly useful when used as the paint which is curable at normal temperature or with heating, and can form a coating being excellent in weather resistance, solvent resistance and antisoil property.

The concentration of the functional groups when used as the curable groups is from 1 to 30% by mole, preferably from 3 to 20% by mole.

The curing agents are optionally selected by considering the functional group in the polymer and are usually polyisocyanates, melamine curing agent, urea resin curing agent, polybasic acid curing agent, epoxy curing agent, polyamine curing agent, polyamide curing agent and the like.

ii) In case where the paint contains the pigment, introduction of a small amount of fluorine-containing olefin having carboxyl group among the compounds (A) enhances affinity (dispersibility of pigment) between the fluorine-containing polymer and the pigment, and thus can give the coating being glossy, smooth and excellent in weather resistance. In this case, the necessary amount of the carboxyl group-containing monomer is from 0.1 to 5% by mole, and particularly not more than 3% by mole is enough.

iii) In case of aqueous emulsion paint or water-soluble paint, introduction of the carboxyl group-containing monomer of the present invention can give dispersion stability in water and water-solubility to the fluorine-containing polymer.

It is possible to enhance dispersion stability of the aqueous emulsion paint in water and to give water-solubility as a water-soluble paint by introducing 0.1 to 10% by mole and 5 to 30% by mole of the carboxyl group-containing monomers, respectively.

iv) In addition, the introduction of the functional groups of the present invention gives various effects such as enhancement of adhesion property of the coating to base materials such as metals, woods, concrete and plastics, improvement of solvent solubility of the polymer, and affinity with the curing agent.

③ The elastomeric fluorine-containing polymers with functional group can be a fluorine-containing rubber being excellent in thermal resistance, chemical resistance, oil resistance, friction property, wear resistance and cold resistance.

i) In case of using as the fluorine-containing rubber, one of the effects of introduction of functional groups is, by utilizing the functional groups of the present invention as a cross-linking site, to proceed vulcanization easily in a relatively short period of time, and thereby the cross-linked products being excellent in physical properties such as tensile strength, elongation, thermal resistance and compression set can be obtained.

As a vulcanizing agent, there can be properly selected and used a polyamine compound, a polyol compound, a polycarboxylic acid compound, a polyepoxy compound, a dibasic acid anhydride or a polyfunctional dibasic acid anhydride compound, an ammonium salt of metal oxide, benzoic acid, cuminic acid or higher fatty acid and an amine hydrochloride, depending on the functional groups in the fluorine-containing elastomer.

ii) In blending a fluorine-containing elastomer and other non-fluorine-containing elastomer, by using the fluorine-containing elastomer of the present invention which is prepared by introducing a functional group to a fluorine-containing elastomer and also in addition, by carrying out the vulcanization in the same manner as mentioned above, there can be obtained excellent physical properties, chemical resistance, flexibility and low temperature property which could not be found on the conventional fluorine-containing elastomer.

As the above-mentioned non-fluorine-containing elastomer, there are preferably acryl type, silicone type, epichlorohydrine type, NBR type and urethane type elastomers.

Also, when selecting a functional group of the fluorine-containing elastomer, kind of the non-fluorine-containing elastomer, a vulcanizing agent and a vulcanizing method and controlling a vulcanization rate of each elastomer and a cross-linking density, co-crosslinking of a system of a fluorine-containing elastomer with functional group and a non-fluorine-containing elastomer can be carried out and a cross-linked blended composition being excellent in mechanical strength and compression set can be obtained. The concentration of the functional groups is from 0.01 to 10% by mole, preferably from 0.1 to 5% by mole when cross-linking or blending and co-crosslinking with the other non-fluorine-containing elastomer by using the functional groups of the above-mentioned fluorine-containing elastomer with functional group.

The third invention of the present inventions relates to the thermoplastic resin composition comprising the above-mentioned fluorine-containing polymer with functional group and a heat-resisting thermoplastic resin.

That is, the thermoplastic resin composition of the present invention comprises a composition blended by mixing (D) 0.1 to 99% (% by weight, hereinafter the same) of the fluorine-containing polymer with functional group and (E) 1 to 99.9% of the heat-resisting thermoplastic resin having a melting point of crystal or glass transition point of not less than 150° C., and as the fluorine-containing polymer (D) with functional group, one or more selected from the fluorine-containing polymers described in the present application are used.

It is possible to provide a composition capable of easily giving homogeneous molded articles which could not be obtained by conventional methods, by using the fluorine-containing polymer with functional group of the present invention at the time of blending the heat-resisting thermoplastic resin and the fluorine-containing polymer.

The fluorine-containing polymer (D) with functional group is the fluorine-containing polymer of the present invention The functional group in the fluorine-containing polymer with functional group is selected mainly depending on kind of the heat-resisting thermoplastic resin (E) to be blended, and there are preferably used the fluorine-containing polymers with hydroxyl group, carboxyl group, a carboxylester group and glycidyl group, which are highly reactive particularly with the thermoplastic resin (E).

The concentration of the functional groups in the fluorine-containing polymer (D) with functional group can be freely selected depending on kind of the thermoplastic resin (E), a ratio of (D) to (E), purpose and use. However the excessive concentration of the functional groups is not desirable from the viewpoint of the properties of the composition such as thermal resistance, chemical resistance and mechanical properties. The concentration may be as minimum as necessary for improving the dispersion when blending with the thermoplastic resin. The content of the fluorine-containing monomer (A) with functional group is preferably from 0.01 to 30% by mole, particularly preferably from 0.05 to 15% by mole on the basis of all monomers used in the fluorine-containing polymer (D) with functional group.

The fluorine-containing polymer (D) with functional group can be properly selected depending on kind of the heat-resisting thermoplastic resin (E) to be used, and use and purpose of the composition or molded articles, and preferable polymer (D) is to comply with the following requirements.

1) Many of the heat-resisting thermoplastic resins (E) are usually melted and kneaded at a temperature of 200° to 380° C. It is preferable that in order to obtain good dispersion, the fluorine-containing polymer (D) is melted at a temperature of not more than 380° C., particularly not more than 350° C., and thereby the thermoplastic resin and the kneading temperature at the time of blending can be selected from a wide range.

2) It is necessary that the fluorine-containing polymer (D) itself has thermal stability (thermal resistance) in kneading and molding at a high temperature. A slight decomposition of the polymer at kneading is unavoidable as far as its effect can be observed. The thermal resistance should be 200° C. at lowest, preferably not less than 250° C. The thermal resistance mainly depends on kind and ratio of monomers to be used. In case where hydrocarbon type monomers, for example, alkyl vinyl ether, alkyl vinyl ester and allyl compounds, excepting ethylene, propylene and isobutylene, are used, it is preferable that the content of the monomers in these polymers is limited to not more than 20% by mole, and particularly the content of not more than 10% by mole is recommendable.

The thermal resistance of the present invention is evaluated by a temperature at which the weight decreases by 1% when measuring with a thermobalance (heating up at 10° C./min) in air.

3) It is necessary that the fluorine-containing polymer itself has a high chemical resistance, oil resistance and solvent resistance and has capability of giving such properties to a composition prepared by blending with the thermoplastic resin (E).

As the fluorine-containing polymer (D) preferable for satisfying the above-mentioned requirements, the first ones are the fluorine-containing copolymers with functional group mainly comprising tetrafluoroethylene (or chlorotrifluoroethylene), and among them, ones prepared by introducing a functional group-containing monomer to so-called FEP, PFA and E(C)TFE are preferable, and particularly preferable are PFA and E(C)TFE type fluorine-containing copolymers with functional group. The most preferable one is an ethylene-tetrafluoroethylene (or chlorotrifluoroethylene) type copolymer.

The second preferable fluorine-containing polymers (D) are vinylidene fluoride type fluorine-containing polymers with functional group, particularly the polymer in which a functional group is introduced to PVdF and the polymer wherein a functional group is introduced to the copolymer mainly comprising vinylidene fluoride. Particularly preferable are the fluorine-containing polymer of PVDF type and the fluorine-containing copolymer with functional group which have the composition including vinylidene fluoride-tetrafluoroethylene copolymer, vinylidene fluoride-tetrafluoroethylene-chlorotrifluoroethylene copolymer, vinylidene fluoride-tetrafluoroethylene-hexafluoropropylene copolymer, vinylidene fluoride-chlorotrifluoroethylene copolymer or vinylidene fluoride-hexafluoropropylene copolymer.

The fluorine-containing polymer with functional group of the present invention may be in any form of resin and elastomer depending on kind and ratio of monomers to be used. The difference between the resin and the elastomer only means that the latter has a glass transition temperature lower than room temperature, and either of them can be selected depending on the purpose of blending. In case of enhancing impact resistance of the thermoplastic resin and preparing an elastomeric blended composition, an elastomeric fluorine-containing polymer with functional group is used.

Among the fluorine-containing polymers (D) of the present invention, the most preferable fluorine-containing elastomers with functional group, which can achieve the above-mentioned purposes, are the fluorine-containing copolymer mainly comprising tetrafluoroethylene and the fluorine containing copolymer mainly comprising vinylidene fluoride.

The molecular weight of the fluorine-containing polymer with functional group of the present invention is equivalent to those of usual fluorine-containing resin and fluorine-containing elastomer excepting PTFE which has a high molecular weight of not less than several millions. The number average molecular weight is 2,000 to 1,000,000. Too low molecular weight impairs thermal resistance of the composition and lowers mechanical properties depending on a proportion of the composition On the other hand, too high molecular weight lowers moldability and thus is not preferable. The preferable number average molecular weight is from about 5,000 to about 750,000, particularly preferable is from about 10,000 to about 500,000.

In the present invention, the fluorine-containing polymer (D) with functional group is blended with the thermoplastic resin (E) having a melting point of crystal or glass transition temperature of not less than 150° C. As the thermoplastic resin, there are, for example, polyacetal, polyamide, polycarbonate, poly(phenylene ether), aromatic polyester, aromatic polyesteramide, aromatic azomethine, poly(arylene sulfide), polysulfone, poly(ether sulfone), polyketone, poly(ether ketone), poly(ether imide), polyamide imide, polymethylpentene, poly(ether nitrile) and the like.

Among them, preferable resins are as follows:

1) Thermoplastic resin (E) itself having an excellent thermal resistance. It is necessary not to lower thermal stability of the composition when blending with the fluorine-containing polymer.

Though the thermoplastic resin (E) having an excellent thermal resistance is used, when usual modifiers and additives are used for improving impact resistance and chemical resistance, the composition lowers in thermal resistance. Therefore a fluorine-containing polymer having an excellent thermal resistance is desired.

2) Thermoplastic resin being excellent in mechanical strength and dimensional stability and being capable of modifying those of the fluorine-containing resin.

3) Thermoplastic resin which is excellent in moldability and can give excellent processability to the composition prepared by blending with a fluorine-containing polymer.

Preferable examples are, for instance, aromatic polyester, polyamide, polyamide imide, poly(arylene sulfide), polyketone, poly(ether nitrile), polycarbonate, poly(phenylene ether), polysulfone, poly(ether imide), polyimide and the like.

Particularly preferable examples are the poly(arylene sulfide) which is strongly desired to be improved in impact resistance without impairing thermal resistance and chemical resistance; the polyamide which is desired to be improved in solvent resistance, particularly gasohol resistance when used as materials for automobile parts; and the aromatic polyester which is expected to enhance moldability and mechanical properties of the fluorine-containing polymer by the addition Among them, there is particularly preferably a liquid crystal polyester forming an anisotropic melt because of its high modulus of elasticity, excellent molding processability and dimensional stability. When enhancing compatibility with the fluorine-containing polymer, the liquid crystal polyester is expected to considerably enhance mechanical properties, moldability, dimensional stability and deflection temperature under load of the fluorine-containing polymer.

On the other hand, in case of considering reactivity of the fluorine-containing polymer (D) with functional group of the present invention with the thermoplastic resin (E), the poly(phenylene sulfide) has a thiolate group (or thiol group), the polyamide has amino group, carboxyl group and amide bond, and the aromatic polyester has hydroxyl group, carboxyl group and ester bond, and thus these resins are preferable because such functional groups are highly reactive with the functional groups in the fluorine-containing polymer (D).

The functional groups of the fluorine-containing polymer (D) with functional group of the present invention are hydroxyl group, carboxyl group, carboxylester group and glycidyl group. These functional groups are in general highly reactive with the ester bond in the trunk chain and hydroxyl group and carboxyl group at the chain end in case where the heat-resisting thermoplastic resin (E) is the aromatic polyester; the amide bond in the trunk chain and amino group and carboxyl group at the chain end in case of polyamide (PA); and the thiolate group (or thiol group) at the chain end in case of poly(arylene sulfide). That is, the composition prepared by melting and kneading the fluorine-containing polymer (D) with functional group and the thermoplastic resin (E) is presumed to be present in any form of (1) a reaction product resulting from a reaction between the functional group of the fluorine-containing polymer (D) with functional group and a part of the trunk chain and/or chain end(s) of the thermoplastic resin (E), (2) a composition obtained by a chemical reaction between a part of the fluorine-containing polymer (D) and a part of the thermoplastic resin (E) in the same manner as in (1), wherein the resulting reaction product acts as a compatibilizing agent for the composition containing unreacted polymers, and (3) a composition wherein interfacial affinity and interfacial adhesivity of the fluorine-containing polymer with the thermoplastic resin (E) are improved by introducing the functional group to the fluorine-containing polymer even without causing a chemical reaction.

As mentioned above, though a mechanism of giving a mutual excellent dispersibility by blending the fluorine-containing polymer (D) with functional group and the thermoplastic resin (E) is not clear, this does not restrict the present invention.

The modification of the thermoplastic resin (E) by usual methods in order to enhance affinity and reactivity with the fluorine-containing polymer with functional group of the present invention also is not excluded from the scope of the present invention.

Also the resin composition of the present invention can comprise a polymer component (F) other than the thermoplastic resin (E) and the fluorine-containing polymer (D) with functional group.

The preferable component as (F) is a fluorine-containing polymer having no functional group, which is defined by excluding the fluorine-containing monomer (A) with functional group and other functional group-containing monomers from the fluorine-containing polymer as described in the present application. The particularly preferable examples of (F) are as follows:

(1) PTFE (including copolymers comprising less than 1% by weight of a fluorine-containing olefin copolymerizable with TFE) and perfluoro type fluorine-containing resins or elastomers such as TFE/perfluoro(alkyl vinyl ether) copolymer (PFA), TFE/HFP copolymer (FEP) and TFE/perfluoro(alkyl vinyl ether)/HFP terpolymer, (2) resinous copolymers commonly known as ETFE or ECTFE, wherein a molar ratio of ethylene to TFE and/or CTFE is 2:3 to 3:2 and a third fluorine-containing monomer copolymerizable therewith is contained in an amount of 0 to 15% by mole on the basis of the total amount of ethylene and TFE and/or CTFE monomers; or elastomeric copolymers comprising about 40 to about 90% by mole of ethylene, about 0.1 to about 20% by mole of TFE and/or CTFE and about 10 to about 60% by mole of a third fluorine-containing monomer, wherein as the third fluorine-containing monomer, there is used at least one represented by $CH_2=CZ^7(CF_2)_{k''}Z^8$ ($Z^7$ is H or F, $Z^8$ is H or F, k" is an integer of 1 to 10), $CF_2=CF(CF_2)_{\lambda''}Y^4$ ($Y^4$ is H or F, $\lambda''$ is an integer of 1 to 10), $CF_2=CFO(CF_2)_{m''}Y^5$ ($Y^5$ is H or F, m" is an integer of 1 to 6) or $CH_2=C(CF_3)_2$; and tetrafluoroethylene/propylene copolymer, for example, elastomeric copolymer comprising 40 to 70% by mole of tetrafluoroethylene and 30 to 60% by mole of propylene, (3) PVDF and VDF type copolymers (resinous or elastomeric copolymers of VDF and at least one selected from fluorine-containing olefins such as TFE, CTFE, HFP, $CH_2=C(CF_3)_2$ or $(CF_3)_2C=O$), wherein VDF/HFP copolymer, VDF/CTFE copolymer and VDF/TFE/HFP or CTFE terpolymer become elastomers usually when VDF is in the range of about 20 to about 80% by mole and TFE is in the range of less than about 40% by mole, HFP is about 10 to about 60% by mole and CTFE is about 15 to about 40% by mole, and (4) as the other polymers, fluorine-containing resins or elastomers such as polychlorotrifluoroethylene (PCTFE) and poly(fluoroalkyl α-substitutedacrylate) wherein the substituent is hydrogen atom, methyl, fluorine atom or chlorine atom.

Namely, in the composition comprising three components, i.e. the fluorine-containing polymer (D) with functional group, the thermoplastic resin (E) and the above-mentioned fluorine-containing polymer (F) without functional group, the reaction products resulting from the reaction of the fluorine-containing polymer (D) with functional group and a part of the thermoplastic resin (E) can function as a compatibilizing agent between the fluorine-containing polymer (F) and the remaining portion of the thermoplastic resin (E). In other words, in blending the fluorine-containing polymer (F) and the thermoplastic resin (E), by adding and melt-blending the fluorine-containing polymer (D) with functional group, the compatibilizing agent is formed in the composition, and the composition can obtain dispersibility, mechanical properties, chemical resistance and the like which cannot be obtained by a simple blend of the fluorine-containing polymer (F) and the thermoplastic resin (E).

Accordingly as the fluorine-containing polymer (D) with functional group, which is added for improving dispersibility in the above-mentioned compositions, one having a high compatibility with the fluorine-containing polymer (F) without functional group is preferable.

For example, it is most preferable, from a point of an effect of improving dispersibility, to add the fluorine-containing polymer with functional group prepared by introducing the functional group to the composition selected from the perfluoro type fluorine-containing resins or elastomers of the above (1) in case where the thermoplastic resin (E) is blended with the fluorine-containing polymer similarly selected from the perfluoro type fluorine-containing resins or elastomers of the above (1) as the fluorine-containing polymer (F); the fluorine-containing polymer prepared by introducing the functional group to the composition selected from the group of (2), i.e. ethylene/tetrafluoroethylene (or chlorotrifluoroethylene) type polymer and propylene/tetrafluoroethylene copolymer, in case where the thermoplastic resin (E) is blended with the fluorine-containing polymer (F) which is selected similarly from the group (2); and the fluorine-containing polymer selected from the fluorine-containing polymers with functional group which mainly comprise vinylidene fluoride, in case where the fluorine-containing polymer (F) is selected from the group of the vinylidene fluoride type polymers of the above (3) and is blended with (E).

An amount of the fluorine-containing polymer (D) with functional group, which is effective for enhancing dispersibility in blending the fluorine-containing polymer (F) and the thermoplastic resin (E), varies depending on kind, blending ratio, purpose of each of the fluorine-containing polymer (F) and the thermoplastic resin (E), and usually and sufficiently effective is from 0.5 to 50% by weight, preferably from 0.5 to 30% by weight on the basis of the whole amount of the composition, and particularly from 1 to 20% by weight.

It is necessary that the three components, i.e. the fluorine-containing polymer (D) with functional group, the thermoplastic resin (E) and the fluorine-containing polymer (F) without functional group, are blended at least under melting and fluidized state at a temperature of not less than the melting point of crystal or glass transition temperature of the thermoplastic resin. It is desirable that during the blending, the fluorine-containing polymer with functional group is also in the molten state, but for the reason of high melt viscosity or cross-linking property, the polymer may keep non-melting state.

The thermoplastic resin composition of the present invention is one prepared by mixing the fluorine-containing polymer (D) with functional group and the thermoplastic resin (E) having a melting point of crystal or glass transition temperature of not less than 150° C., and the content of (D) is from 0.1 to 99% and (E) is from 1 to 99.9%.

In case where (D) is from 0.1 to 40% and (E) is from 60 to 99.9%, the properties such as impact resistance, sliding property, chemical resistance and moldability which are drawbacks of many of the thermoplastic resins, can be enhanced by the fluorine-containing polymer. Also in case of 40 to 99% of (D) and 1 to 60% of (E), properties of the fluorine-containing polymer such as strength, deflection temperature under load, moldability and dimensional stability can be enhanced by the thermoplastic resin. In case where in the weight ratio of the resin composition, (D) is less than 0.1% and (E) is less than 1%, the above-mentioned enhancing effect becomes unsatisfactory.

The content and kind of the fluorine-containing polymer with functional group in the composition vary depending on kind and concentration of the functional group, main components and molecular weight of the polymer, and therefore are not equally determined and are selected according to kind of the thermoplastic resin to be blended in the above-mentioned range and purpose of the blending.

The preferable resin composition of the present invention is one comprising the fluorine-containing polymer having hydroxyl group, carboxyl group or glycidyl group and the poly(arylene sulfide), polyamide, aromatic polyester or polycarbonate.

Poly(arylene sulfide) is excellent in thermal resistance and mechanical properties, but inferior particularly in impact resistance. In blending poly(arylene sulfide) and the fluorine-containing polymer (D) with functional group, it is preferable, for enhancing dispersibility, to use the fluorine-containing polymers (D) having hydroxyl group and having glycidyl group which are highly reactive with a thiolate group (or thiol group) at the chain end of poly(phenylene sulfide). Among them, elastomeric fluorine-containing polymer is particularly preferable for enhancing impact resistance.

The concentration of the functional groups in the fluorine-containing elastomer varies depending on kind and mixing ratio of the fluorine-containing elastomer and the poly(arylene sulfide), and is from 0.01 to 30% by mole, preferably from 0.01 to 20% by mole, particularly preferably from about 0.05 to about 10% by mole per the number of moles of the monomers used in the fluorine-containing elastomer.

Preferable examples of the functional group-containing elastomer are elastomers having hydroxyl group or glycidyl group as the functional group among the vinylidene fluoride type fluorine-containing polymers, or elastomers having hydroxyl group or glycidyl group as the functional group among the fluorine-containing polymers mainly comprising tetrafluoroethylene. Among these polymers, particularly preferable are vinylidene fluoride-hexafluoropropylene copolymer, vinylidene fluoride-tetrafluoroethylene-hexafluoropropylene copolymer and tetrafluoroethylene-propylene copolymer, to which hydroxyl group or glycidyl group is introduced.

As PPS used in the present invention, there is no restriction if it is prepared by the known method as mentioned in JP-B-3368/1970, and PPS containing 70% by mole or more of the recurring unit shown by the formula:

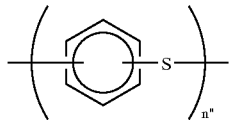

is preferable. Further there is used particularly preferably PPS having the poly(phenylene sulfide) unit of not less than 70% by mole. At that time, there is no restriction on the residual recurring units if they are copolymerizable. Examples are o-phenylene sulfide unit, m-phenylene sulfide unit, diphenyl sulfide ether unit, diphenyl sulfide sulfone unit, diphenyl sulfide ketone unit, biphenyl sulfide unit, naphthalene sulfide unit, trifunctional phenylene sulfide unit and the like. These copolymers may be block-copolymerized or random-copolymerized.

Examples of the preferred PPS are poly(p-phenylene sulfide), poly(p-phenylene sulfide)-poly(m-phenylene sulfide) block copolymer, poly(p-phenylene sulfide)-polysulfone block copolymer and poly(p-phenylene sulfide)-polyphenylene sulfide sulfone copolymer.

Structure of PPS may be a straight chain type, a cross-linked type with oxygen in coexistence with oxygen, a heat-treated type under inert gas atmosphere and an admixture of these structures.

Also a functional group having high reactivity may be introduced to PPS to further enhance the compatibility with the fluorine-containing polymer with functional group of the present invention. As the functional group to be introduced, amino group, carboxyl group, hydroxyl group and the like are suitable. As the introducing methods, there are a method in which a halogenated aromatic compound with functional group is copolymerized, a method in which the functional group is introduced by polymer reaction of PPS with a low molecular weight compound with functional group, and the like.

The above-mentioned PPS may be one which is reduced in sodium ion content by deionization treatment (acid cleaning and hot water cleaning or the like).

The fluorine-containing elastomer with functional group and poly(arylene sulfide) can be used in the range of 0.1 to 40% and 60 to 99.9%, respectively, particularly preferably 5 to 30% and 70 to 95%. In case where the fluorine-containing elastomer with functional group is less than 5%, impact resistance cannot be improved sufficiently, and contrarily when more than 30%, mechanical strength lowers remarkably.

The composition which comprises the poly(phenylene sulfide) prepared in the manner mentioned above and the fluorine-containing polymer with functional group can give the molded articles excellent mechanical properties, particularly an excellent impact resistance, which cannot be obtained by simply blending the fluorine-containing polymer without functional group.

Also since the thermoplastic resin composition has thermal resistance, chemical resistance and sliding property which are inherent to the fluorine-containing polymer and also the thermal resistance and mechanical properties which are inherent to poly(phenylene sulfide), the composition is useful particularly as a molding material for electrical and electronic parts by utilizing its thermal resistance and electrical properties; for automobile parts by utilizing its sliding property; for pipes and valves for chemical plant and gear parts for pumps by utilizing its chemical resistance; and the like.

Polyamide resins have a high strength, high toughness and excellent processability and are used widely for hoses, tubes, pipes and the like. On the other hand, though they are usually excellent in oil resistance, they are poor in resistance to an alcohol type solvent. In case where gasoline containing a lower alcohol is used, oil resistance (gasohol resistance) is worse to swell in volume and to increase fuel penetration, which causes deterioration of materials such as decrease in strength.

The composition having the improved solvent resistance and gasohol resistance of the polyamide resin can be prepared by blending the fluorine-containing polymer (D) with functional group of the present invention with the polyamide resin or by adding the fluorine-containing polymer (D) with functional group to a blended composition of the fluorine-containing polymer (F) and the polyamide resin.

As the fluorine-containing polymer (D) with functional group in the composition comprising the polymer (D) and polyamide, preferable is the fluorine-containing polymer with carboxyl group or the fluorine-containing polymer with glycidyl group, in view of high reactivity to any of amide bond of the trunk chain of polyamide or amino group or carboxyl group at the chain end(s). The concentration of the functional groups varies depending on kind, mixing ratio and purpose of the fluorine-containing polymer and polyamide resin, and is preferably from 0.01 to 30% by mole, more preferably from 0.01 to 20% by mole, particularly preferably from about 0.05 to about 10% by mole per the number of moles of the fluorine-containing polymer.

As the fluorine-containing polymer (D) with functional group, either of resinous or elastomeric polymer can be selected depending on the purpose and use. In case of resinous fluorine-containing polymers, there is no restriction if they are capable of heat-melting. Among them, the fluorine-containing polymers having a relatively low melting point, that is, a melting point of not more than 300° C., particularly not more than 280° C. are especially preferable to prevent thermal deterioration of polyamide in the composition when preparing the composition by melting and kneading with polyamide. Concretely the ethylene-tetrafluoroethylene (or chlorotrifluoroethylene) copolymers with carboxyl group or glycidyl group and the vinylidene fluoride type polymers with carboxyl group or glycidyl group are preferable. Particularly preferable vinylidene fluoride type polymers are PVDF, and the copolymers such as vinylidene fluoride-tetrafluoroethylene copolymer, vinylidene fluoride-hexafluoropropylene copolymer, vinylidene fluoride-chlorotrifluoroethylene copolymer, vinylidene fluoride-tetrafluoroethylene-hexafluoroethylene copolymer and vinylidene fluoride-tetrafluoroethylene-chlorotrifluoroethylene copolymer, to each of which carboxyl group or glycidyl group is introduced.

Also preferable elastomeric fluorine-containing polymers are the copolymers with carboxyl group and glycidyl group, which comprise mainly tetrafluoroethylene, and the vinylidene fluoride copolymers.

Also the composition having the improved dispersibility and chemical resistance can be obtained by adding the fluorine-containing polymer (D) with functional group when blending the fluorine-containing polymer (F) without functional group and the polyamide resin. Examples of the compositions are a composition prepared by adding the polymer having carboxyl group or glycidyl group to a blend of ETFE (or ECTFE) and polyamide; a composition prepared by adding the polymer which has carboxyl group or glycidyl group and is selected from the vinylidene fluoride type polymers, to a blend of PVDF and polyamide resin; and a composition prepared by adding the polymer which has carboxyl group or glycidyl group and is selected from the vinylidene fluoride type polymers, to a blend of polyamide and the resinous or elastomeric vinylidene fluoride type polymer comprising vinylidene fluoride as the essential component and at least one selected from tetrafluoroethylene, hexafluoropropylene and chlorotrifluoroethylene.

In case of a composition prepared by adding the fluorine-containing polymer (D) with functional group to a blend of polyamide and the fluorine-containing polymer (F) without functional group, the content of (D), which is effective for enhancing dispersibility and compatibility, varies depending on kind, mixing ratio and the like of the fluorine-containing polymer (F) and polyamide, and is usually from 0.5 to 50%, preferably from 0.5 to 30%, particularly preferably from 1 to 20% on the basis of the whole amount of the composition.

As the polyamide resins, there can be usually used ones prepared by condensation of a linear diamine represented by the following formula:

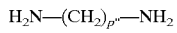

wherein p" is an integer of 3 to 12, and a linear carboxylic acid represented by the following formula:

wherein q" is an integer of 2 to 12, and ones prepared through ring-opening polymerization of lactam. Examples of the preferable polyamides are nylon 66, nylon 610, nilon 612, nylon 46, nylon 34, nylon 69, nylon 6, nylon 12, nylon 11, nylon 4 and the like. Also there can be used copolymerized polyamides such as nylon 6/610, nylon 6/612, nylon 6/46, nylon 6/12, nylon 6/66, nylon 6/66/610, nylon 6/46/66, nylon 6/66/612, nylon 6/46/610 and nylon 6/46/12.

Also there can be used nylon 6/6T (T is a terephthalic acid component), semi-aromatic polyamides obtained from an aromatic dicarboxylic acid such as terephthalic acid or isophthalic acid and meta-xylene diamine or an alicyclic diamine, and polyamides obtained from meta-xylene diamine and the above-mentioned linear carboxylic acid.

The compositions as mentioned above, which comprise the fluorine-containing polymer (D) with functional group and polyamide, and the compositions prepared by adding the fluorine-containing polymer (D) with functional group to the blend of the fluorine-containing polymer (F) without functional group and polyamide can give molded articles having an excellent chemical resistance, impact resistance at low temperature and mechanical properties which cannot be obtained by simply blending the fluorine-containing polymer without functional group. These compositions are useful as materials having an excellent chemical resistance and impermeability, particularly against reformate gasoline containing an alcohol (for example methanol, ethanol and the like) or methyl t-butyl ether and an acid. Therefore, the compositions are useful for molded articles such as hoses, tubes, pipes, sealings, gaskets, packings, sheets and films. Also the compositions can be materials useful for automobile parts which require chemical resistance and impermeability against gasoline and methanol-mixed gasoline, e.g. hoses, tubes, gaskets and the like for fuel piping.

Perfluoro type fluorine-containing resins such as PTFE, FEP and PFA and fluorine-containing resins such as ETFE, ECTFE, PVDF and vinylidene fluoride type copolymers (for example, vinylidene fluoride-tetrafluoroethylene copolymer and the like) are in general excellent in thermal resistance, chemical resistance, weather resistance, electrical properties and the like, but in many cases are inferior in mechanical properties, physical thermal resistance shown by deflection temperature under load, dimensional stability and the like as compared with crystalline heat-resisting thermoplastic resins.

There can be obtained the composition in which mechanical properties, deflection temperature under load and dimensional stability of the fluorine-containing resin are improved by using the fluorine-containing resin (D) with functional group of the present invention in place of the conventional fluorine-containing resins, by blending the heat-resisting thermoplastic resins (E), particularly aromatic polyester or polycarbonate, or by adding the fluorine-containing polymer (D) with functional group when blending the conventional fluorine-containing resin (F) and the aromatic polyester or polycarbonate.

As the fluorine-containing polymer (D) in the composition comprising the aromatic polyester or polycarbonate and the fluorine-containing polymer (D) with functional group, the polymers having hydroxyl group, carboxylester group or glycidyl group are preferable. Among them, particularly preferable are fluorine-containing polymers having hydroxyl group or carboxylester group which is seemed to be easily subjected to transesterification with the ester group at the trunk chain of the aromatic polyester or the carbonate group at the trunk chain of polycarbonate. The proportion of the hydroxyl group, carboxylester group or glycidyl group varies depending on kind of the aromatic polyester and polycarbonate, kind of the fuorine-containing polymer and composition ratio, and is from 0.01 to 30% by mole, preferably from 0.01 to 20% by mole, particularly from about 0.05 to about 10% by mole per the total amount of the fluorine-containing polymer with functional group.

In case of the composition comprising two components, i. e. a fluorine-containing polymer with functional group and the aromatic polyester or polycarbonate, various fluorine-containing polymers with functional group can be selected depending on purpose and use, and preferable are polymers such as PTFE, FEP, PFA, ETFE, ECTFE, PVdF, vinylidene fluoride type copolymer resin (VdF-TFE copolymer and the like) and PCTFE, to which hydroxyl group or carboxylester group is introduced Among them, particularly preferable are PFA, ETFE, ECTFE, PVdF and PCTFE to which hydroxyl group or carboxylester group is introduced. The mechanical properties, deflection temperature under load, dimensional stability and moldability of each corresponding fluorine-containing resin can be effectively improved.

In the composition comprising two components, i.e. the fluorine-containing polymer (D) with functional group and the aromatic polyester or polycarbonate, the proportions effective for improving mechanical properties, deflection temperature under load, dimensional stability and moldability are from 50 to 99% of the fluorine-containing polymer (D) with functional group and 1 to 50% of the aromatic polyester or polycarbonate (E), preferably 60 to 97% of (D) and 3 to 40% of (E).

In case of the composition comprising three components in which the fluorine-containing polymer (D) with functional group of the present invention is added at the time of the blending of the conventional fluorine-containing resin (F) and the aromatic polyester or polycarbonate, there is preferably selected the fluorine-containing polymer (D) with functional group having good compatibility with the fluorine-containing resin (F) without functional group in the composition As the examples of the composition, particularly preferable are a composition prepared by adding the fluorine-containing polymer, which is obtained by introducing hydroxyl group or carboxylester group to the polymer selected from perfluoro type fluorine-containing resins (for example, PTFE, FEP, PFA and the like), to a blend of the perfluoro type fluorine-containing resin and the aromatic polyester or polycarbonate; a composition prepared by adding the ethylene/tetrafluoroethylene (or chlorotrifluoroethylene) copolymer with hydroxyl group or carboxylester group, to a blend of ETFE (or ECTFE) and the aromatic polyester or polycarbonate; and a composition prepared by adding the vinylidene fluoride type polymer (in this case, either of the resinous or elastomeric polymer may be used) with hydroxyl group or carboxylester group, which is selected from polymers mainly comprising vinylidene fluoride to a blend of PVdF or the vinylidene fluoride type copolymer resin and the aromatic polyester or polycarbonate.

In the composition prepared by adding the fluorine-containing polymer (D) with functional group to the blend of the conventional fluorine-containing resin and the aromatic polyester or polycarbonate, the content of the abovementioned (D), which is effective for enhancing dispersibility and compatibility, varies depending on kind and mixing ratio of the fluorine-containing resin, aromatic polyester and polycarbonate, and is usually from 0.5 to 50%, preferably from 0.5 to 30%, particularly preferably from 1 to 20% on the basis of the whole amount of the composition In the composition of three components prepared by adding the fluorine-containing polymer (D) with functional group to the blend of the fluorine-containing resin (F) and the aromatic polyester or polycarbonate (E), the proportion effective for improving mechanical properties, deflection temperature under load, dimensional stability and moldability of the fluorine-containing polymer is 0.5 to 50% of the fluorine-containing polymer (D) with functional group, 1 to 50% of the aromatic polyester or polycarbonate (E) and remaining amount of the fluorine-containing resin (F) (provided that the sum of (D) and (F) is 50 to 99%), preferably 1 to 30% of (D), 3 to 40% of (E) and remaining amount of (F) (provided that the sum of (D) and (F) is 60 to 97%).

When the elastomeric fluorine-containing polymer is used as the functional group-containing polymer (D) of the present invention and is melt-blended with the thermoplastic resin (E), a chemical reaction occurs partly, and a thermoplastic elastomer composition can be obtained in a specific composition ratio of (D) to (E). Specifically by melt-blending the aromatic polyester or polycarbonate with the fluorine-containing polymer with functional group of the present invention, particularly a fluorine-containing elastomer with hydroxyl group or carboxylester group in a specific composition ratio thereof, the transesterification occurs partly and there can be obtained a thermoplastic elastomer composition having flowability at a high temperature as a thermoplastic resin and rubber elasticity as an elastomer. In this thermoplastic elastomer composition, as the elastomer with hydroxyl or carboxylester group, there are particularly preferably used a polymer mainly comprising tetrafluoroethylene and a polymer mainly comprising vinylidene fluoride. The content of hydroxyl group or carboxylester group is from 0.01 to 30% by mole, preferably from 0.01 to 20% by mole, particularly preferably from 0.05 to 10% by mole on the basis of the whole monomers of the fluorine-containing elastomer.

In mixing the aromatic polyester or polycarbonate and the fluorine-containing elastomer with hydroxyl group or carboxylester group, the mixing ratio thereof, which can endow the elastomeric composition with flowability at a high temperature and rubber elasticity as a thermoplastic elastomer, is from 50 to 99.9% of the fluorine-containing elastomer with hydroxyl group or carboxylester group and 0.1 to 50% of the aromatic polyester or polycarbonate, particularly preferably 70 to 98% and 2 to 30%, respectively. Also thermoplastic elastomers having various hardness can be prepared by selecting the mixing ratio in the above range.

The use of polycarbonate is extending to the fields of automobiles and building because of their characteristics such as mechanical strength, impact resistance and weather resistance, but they are inferior in chemical resistance, particularly alkali resistance and solvent resistance.

The composition having more effectively improved chemical resistance without remarkably lowering mechanical properties can be obtained by blending the fluorine-containing polymer with hydroxyl group among the fluorine-containing polymers with functional group of the present invention and polycarbonate in the same manner as in case of improving chemical resistance of the polyamide.

As the aromatic polyester used in the composition of the present invention, there are condensation products of a dibasic acid such as adipic acid, terephthalic acid, 2,6-naphthalenedicarboxylic acid or 4,4'-biphenyldicarboxylic acid and a dihydric alcohol such as ethylene glycol, trimethylene glycol, tetramethylene glycol, pentamethylene glycol, hexamethylene glycol, 1,4-cyclohexanedimethanol or bisphenol A (for example, polyethylene terephthalate, polybutylene terephthalate, poly-1,4-cyclohexanedimethylene terephthalate, poly[2,2-propanebis (4-phenyltere/isophthalate)] and the like); aromatic polyesters (liquid crystal copolyester) forming an anisotropic melt; and the like.

Also the polycarbonate used in the composition of the present invention is obtained by a reaction of a bisphenol compound and phosgene or a diester carbonate. As the bisphenol compound, 2,2-bis(4-hydroxyphenyl)propane (hereinafter referred to as "bisphenol A") is particularly preferable, and a part or the whole of bisphenol A may be substituted by other bisphenol compounds. As the bisphenol compounds other than bisphenol A, there are, for example, hydroquinone, resorcin, 4,4'-dihydroxydiphenyl, bis(4-hydroxyphenyl)alkane, bis(4-hydroxyphenyl) cycloalkane, bis(4-hydroxyphenyl)sulfide, bis (4-hydroxyphenyl) ether, bis (4-hydroxyphenyl) ketone, bis(4-hydroxyphenyl) sulfone, bis(4-hydroxyphenyl)sulfoxide, or an alkyl-substituted product, an aryl-substituted product or a halogen-substituted product thereof and the like.

Among them, the liquid crystal polyester itself is, because of its orientation, most excellent in mechanical properties such as strength and modulus of elasticity, in thermal properties such as deflection temperature under load and in dimensional stability, and shows a high flowability at the time of melting. Further the liquid crystal polyester orientates in the composition by melt-blending with other polymers, and thus can endow the composition with similar excellent characteristics as mentioned above. Therefore the polyester can be used most preferably for preparing a composition having the improved mechanical properties, deflection temperature under load, dimensional stability and moldability of the fluorine-containing resin and the thermoplastic elastomeric composition. As the liquid crystal polyester used in the present invention, there are, for example, liquid crystal copolyesters comprising the components selected from one or more of aromatic dicarboxylic acids and alicyclic dicarboxylic acids, one or more of aromatic diols, alicyclic diols and aliphatic diols and one or more of aromatic hydroxycarboxylic acids. As the represented combinations thereof, there are, for example, polyesters mainly comprising para-hydroxybenzoic acid, biphenyl diol and terephthalic acid (for example, ECONOL E2000, E6000 or E7000 available from Sumitomo Chemical Co., Ltd., Xydar RC/FC400, 300 available from Nippon Petrochemicals Co., Ltd., VECTRA C Series available from Polyplastics Co., Ltd., UENO LCP2000 available from Ueno Fine Chemical Co., Ltd. and IDEMITSU LCP300 available from Idemitsu Petrochemicals Co., Ltd.; polyesters mainly comprising para-hydroxybenzoic acid and 6-hydroxynaphthoic acid (for example, VICTREX SRP available from ICI Japan Ltd., UENO LCP1000 available from Ueno Fine Chemical Co., Ltd., VECTRA A Series available from Polyplastics Co., Ltd., NOVACCURATE E324 available from Mitsubishi Chemical Corp., IDEMITSU LCP 300 available from Idemitsu Petrochemicals Co., Ltd., and LODRUN LC-5000 available from Unitika Ltd.); polyesters mainly comprising para-hydroxybenzoic acid, terephthalic acid and an aliphatic diol (for example, NOVACCURATE E310 available from Mitsubishi Chemical Corp., IDEMITSU LCP100 available from Idemitsu Petrochemicals Co., Ltd., LODRUN LC-3000 available from Unitika Ltd. and X7G available from Eastman Kodak Corp.); and the like.

In case where the thermoplastic elastomer composition is prepared by blending the fluorine-containing elastomer with functional group of the present invention and the above-mentioned liquid crystal polyester, it is preferable to use a liquid crystal copolyester mainly comprising 6-hydroxynaphthoic acid and para-hydroxybenzoic acid having a relatively low melting temperature or a liquid crystal copolyester mainly comprising para-hydroxybenzoic acid, terephthalic acid and aliphatic diol in consideration of thermal resistance of the fluorine-containing elastomer with functional group.

Among the fluorine-containing thermoplastic resin compositions comprising the aromatic polyester or polycarbonate of the present invention which are prepared in the above manner, the compositions which have the improved mechanical properties, deflection temperature under load, dimensional stability and moldability of the fluorine-containing resin, have, in addition thereto, excellent thermal resistance, chemical resistance and electrical properties which are inherent to the fluorine-containing resin. As a result, the composition can be particularly useful materials for electrical and electronic parts which require dimensional stability, thermal resistance and electrical properties, for example, connectors, chips, carriers, receptacles, printed board, covering material for wire and the like; chemically resistive parts relating to semiconductor production, particularly large size wafer baskets which are difficult to be produced from the fluorine-containing resin solely due to lack of moldability and strength, or valves and parts for chemical pumps; machine parts such as fuel-related parts for automobiles, gears and bearings, which require thermal resistance and sliding property; and the like.

The thermoplastic elastomer composition comprising the above-mentioned fluorine-containing elastomer with hydroxyl group or carboxylester and the aromatic polyester or polycarbonate is one in which the fluorine-containing elastomer component forms a continuous phase by a chemical bond between a part of the aromatic polyester or polycarbonate giving flowability at high temperature to the composition and a part of the fluorine-containing elastomer being capable of giving rubber elasticity through the functional groups of the fluorine-containing elastomer. Accordingly the composition of the present invention is excellent in thermal resistance and chemical resistance as compared with the conventional elastomeric thermoplastic composition prepared by dynamically vulcanizing a fluorine-containing elastomer into a thermoplastic resin so that the thermoplastic resin forms a continuous phase. Also since the composition of the present invention can be prepared only by melt-blending without using any vulcanizing agent and additive, the lowering of chemical resistance due to those impurities and the contamination due to their elusion can be prevented.

Also the composition of the present invention has, of course, moldability in injection molding and recycling capability as thermoplastic elastomers.

Accordingly the elastomeric thermoplastic composition of the present invention is a useful material for uses in the field of medicine and biochemistry such as for tubes, plugs of drug bottles, gaskets and injectors; in the field of semiconductor industry such as for tubes, O rings and sealants; in the field of electrics and electronics such as for heat insulating coatings of wires and sealants; in the field of food industry such as for hoses and sealants; in the field of automobile industry such as for fuel hoses, tubes, gaskets, equal velocity joint boots and rack and pinion boots; in the field of chemical industry such as for pressure-resistance hoses, diaphragms, packings, gaskets and hoses; in the field of building industries such as for sealants; and the like.

Further the resin composition of the present invention may contain, as far as its effect is not impaired, organic or inorganic fillers to be used usually, for example, fibrous reinforcements such as glass fiber, carbon fiber, aramide fiber, graphite whisker, potassium titanate whisker, basic magnesium sulfate whisker, magnesium whisker, magnesium borate whisker, calcium carbonate whisker, calcium sulfate whisker, zinc oxide whisker, aluminium borate whisker, alumina whisker, silicon carbide whisker, silicon nitride whisker, wollastonite, xonotlite, sepiolite, gypsum fiber and slag fibers; inorganic fillers such as carbon powder, graphite powder, calcium carbonate powder, talc, mica, clay and glass beads; heat-resisting resins such as polyimide; and further solid lubricants such as molybdenum disulfide, colorants and retarders, and the content thereof is usually from 1 to 30% on the basis of the whole amount of the composition. There is a case where an effect of the addition is far more enhanced because of the presence of unreacted functional groups contained in the resin composition of the present invention.

As the melting and mixing machines used in the present invention, there are a mixing roll, Banbury mixer, Brabender mixer, an extrusion machine and the like, and among them, an extrusion machine is preferable from the points that kneading power is large and the dispersibility is expected to be enhanced more at blending and also that productivity is excellent in the production of the composition. As the extrusion machine, there can be used ones of uniaxial screw or biaxial screw type or ones having more than two screws, and the biaxial screw type extrusion machine is particularly preferable from the points that the compositions having good dispersibility can be obtained because of larger kneading power and that the kneading power can be optionally controlled.

BEST MODE FOR CARRYING OUT THE INVENTION

Figure 1:
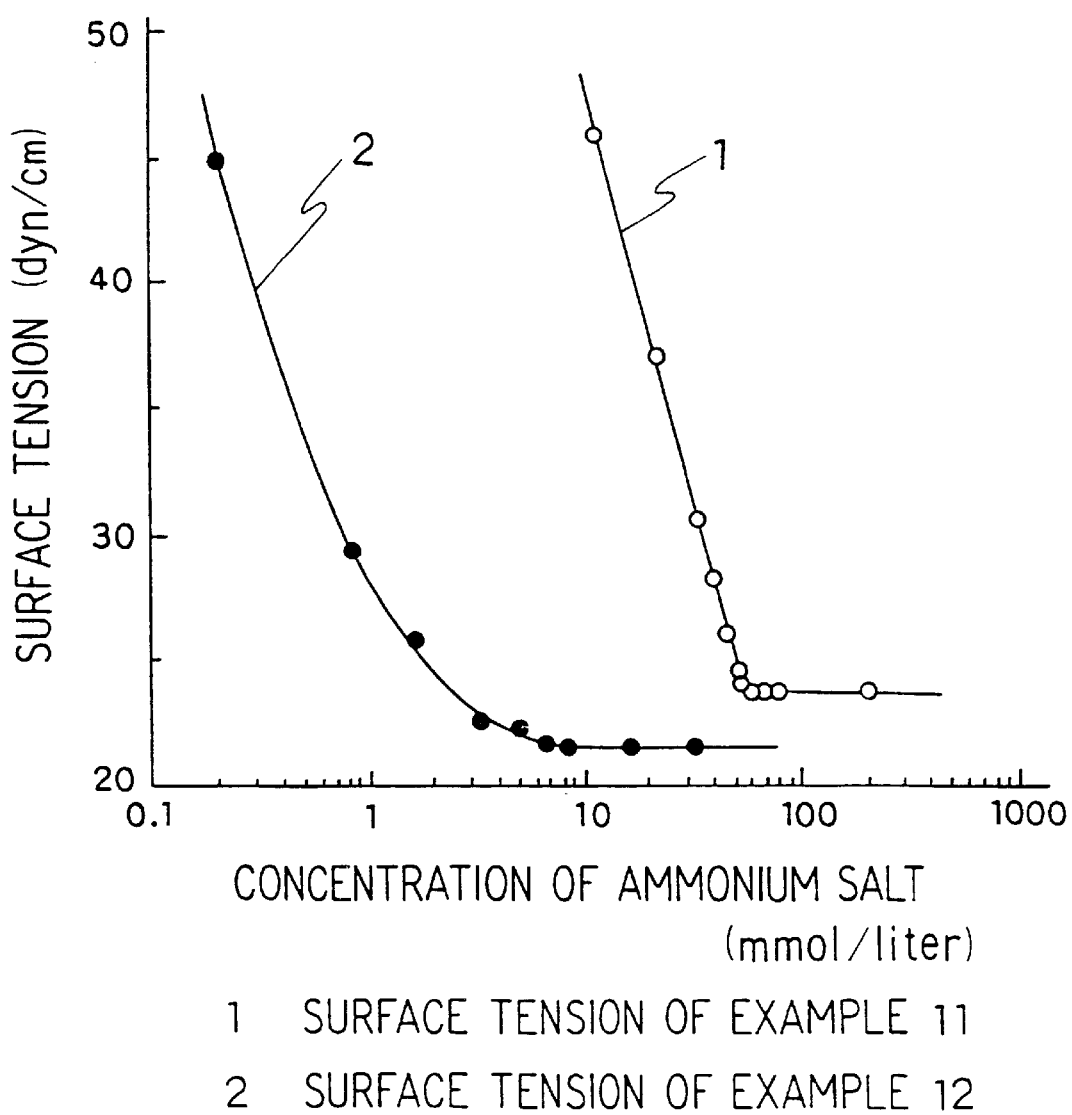
FIG. 1 is a graph showing measurements of surface tension of EXAMPLES 11 and 12.

Synthesis of the fluorine-containing olefin and fluorine-containing polymer of the present invention and production of the thermoplastic resin composition using the fluorine-containing polymer are explained below on the basis of EXAMPLES, but the present invention is not limited thereto.

I. Examples relating to the fluorine-containing monomer with functional group

In the following examples, abbreviations and symbols mentioned below are used.

R-11: Trichlorofluoromethane
NMR: Nuclear magnetic resonance spectrum
IR: Infrared absorption spectrum
MS: Mass spectrum

REFERENCE EXAMPLE 1

2,2-difluoro-3-iodopropionyl fluoride ($ICH_2CF_2COF$)

A three-liter four-necked flask was charged with 1,500 m$\lambda$ of tetraglyme, and 825 g of sodium iodide was completely dissolved with stirring at room temperature. Subsequently with feeding water to a cooler, 650 g of 2,2,3,3-tetrafluorooxetane was added slowly and dropwise at a reaction temperature ranging from 30° to 40° C., and the addition was completed in 45 minutes.

The titled compound, i.e. 2,2-difluoro-3-iodopropionyl fluoride of 1,050 g was recovered by distilling the reaction mixture under reduced pressure of 30 mmHg at 38° to 40° C. Boiling point: 95° to 96° C.

REFERENCE EXAMPLE 2

Synthesis of methyl perfluoro(6,6-dihydro-6-iodo-2trifluoromethyl-3-oxahexanoate)
($ICH_2CF_2CF_2OC(CF_3)FCOOCH_3$)

A two-liter four-necked flask was charged with 43 g of cesium fluoride, 6 m$\lambda$ of tetraglyme and 400 g of 2,2-difluoro-3-iodopropionyl fluoride prepared in REFERENCE EXAMPLE 1, and the inside temperature was adjusted to 10° C. with stirring. Subsequently after introducing hexafluoropropylene oxide from a gas bomb into the flask for 21 hours at a reflux speed through a dry ice cooler, 300 m$\lambda$ of methanol was added with cooling by iced water. After rinsing the reaction product with water several times, there was obtained, through distillation, the titled compound, i.e. methyl perfluoro(6,6-dihydro-6iodo-2-trifluoromethyl-3-oxahexanoate). Yield: 250 g, boiling point: 116° to 117° C. (60 mmHg).

REFERENCE EXAMPLE 3

Synthesis of methyl perfluoro(9,9-dihydro-9-iodo-2, 5bistrifluoromethyl-3,6-dioxanonanoate)
($ICH_2CF_2CF_2OC—(CF_3)FCF_2OC—(CF_3)FCOOCH_3$)

A two-liter four-necked flask was charged with 60 g of cesium fluoride, 10 m$\lambda$ of tetraglyme and 600 g of 2,2-difluoro-3-iodopropionyl fluoride prepared in REFERENCE EXAMPLE 1, and the inside temperature was adjusted to 10° C. with stirring. Subsequently after introducing hexafluoropropylene oxide from a gas bomb into the flask for 30 hours at a reflux speed through a dry ice cooler, 500 m$\lambda$ of methanol was added with cooling by iced water. After rinsing the reaction product with water several times, there was obtained, through distillation, the titled compound, i.e. methyl perfluoro(9,9-dihydro-9iodo-2,5-bistrifluoromethyl-3,6-dioxanonanoate). Yield: 116 g, boiling point: 100° to 101° C.(15 mmHg).

REFERENCE EXAMPLE 4

Synthesis of methyl perfluoro(12,12-dihydro-12-iodo-2,5,8-tristrifluoromethyl-3,6,9-trioxadodecanoate)
($ICH_2CF_2CF_2OC(CF_3)FCF_2OC(CF_3)FCF_2OC(CF_3)FCOOCH_3$)

After rinsing, with water, the reaction product prepared in the same manner as in REFERENCE EXAMPLE 3, the titled compound, i.e. methyl perfluoro(12,12,-dihydro-12-iodo-2,5,8-tristrifluoromethyl-3,6,9-trioxadodecanoate) was obtained through distillation. Yield: 85 g, boiling point: 105° to 106° C.(2 mmHg).

EXAMPLE 1

Synthesis of methyl perfluoro(6,6-dihydro-2-trifluoromethyl-3-oxa-5-hexenoate)
($CH_2=CFCF_2OC(CF_3)FCOOCH_3$)

A one-liter four-necked flask equipped with a stirrer, cooler and dropping funnel was charged with 500 m$\lambda$ of methanol and 84.6 g of zinc powder, and the inside temperature was adjusted to 60° to 65° C. With stirring, 270 g of methyl perfluoro(6,6-dihydro-6-iodo-2trifluoromethyl-3-oxahexanoate) prepared in REFERENCE EXAMPLE 2 was added dropwise for about one hour through the dropping funnel. Further after stirring at 65° to 68° C. for one hour, the inside temperature was cooled to room temperature.

The reaction mixture was filtrated to separate excessive zinc, and then poured into 1 liter of 1N hydrochloric acid. After allowed to stand, an organic layer was collected, rinsed with water, dried and then distilled to obtain the titled compound, i.e. methyl perfluoro(6,6-dihydro-2-trifluoromethyl-3-oxa-5hexenoate). Yield: 171.9 g, boiling point: 72° to 73° C. (95 mmHg).

$^1$H-NMR: δ (ppm) (in $CDCl_3$), 5.55 to 5.38 (2H, m), 4.06 (3H, s.br.).

$^{19}$F-NMR: δ (ppm) (in $CDCl_3$, R-11 internal standard), −70.8 to −71.5 (1 F, m), −77.5 to −78.1 (1 F, m), −82.3 (3 F, s.br.), −124.2 to −124.5 (1 F, m), −131.3 to −131.4 (1 F, m).

IR($cm^{-1}$): 1787 (ν c=o), 1695 (ν c=c).

MS(m/e): 270 (P), 159 (C—($CF_3$)FCOOCH$_3$), 95 ($CH_2=CFCF_2$), 69 ($CF_3$), 59 ($COOCH_3$), 15 ($CH_3$).

EXAMPLE 2

Synthesis of perfluoro(6,6-dihydro-2-trifluoromethyl-3-oxa-5-hexenoic acid)
($CH_2=CFCF_2OC—(CF_3)FCOOH$)

A 500 m$\lambda$ four-necked flask equipped with a stirrer, cooler and dropping funnel was charged with 17.1 g of sodium hydroxide and 300 m$\lambda$ of methanol to dissolve them completely, and the inside temperature was kept at room temperature. With stirring, 100 g of methyl perfluoro-(6,6-dihydro-2-trifluoromethyl-3-oxa-5hexenoate) prepared in EXAMPLE 1 was added dropwise for about 30 minutes through the dropping funnel, and further after stirring at room temperature for one hour, the solution was poured into 1 liter of 2N hydrochloric acid. After allowed to stand, an organic layer was collected, rinsed with water, dried and then distilled to obtain the titled compound, i.e. perfluoro (6,6-dihydro-2-trifluoromethyl-3-oxa-5-hexenoic acid). Yield: 50.5 g, boiling point: 81° to 82° C. (20 mmHg).

$^1$H-NMR: δ (ppm) (in CDCl$_3$), 11.5 (1H, s.br.), 5.50 to 5.37 (2H, m).

$^{19}$F-NMR: δ (ppm) (in CDCl$_3$, R-11 internal standard), –70.5 to –71.3 (1 F, m), –77.2 to –77.8 (1 F, m), –82.4 (3 F, m), –124.1 to –124.4 (1 F, m), –131.3 to –131.5 (1 F, m).

IR(cm$^{-1}$): 3511 (ν non-associated OH), 2655 to 3300 (ν associated OH), 1771 (ν c=o), 1695 (ν c=c).

MS(m/e): 256 (P), 145 (C—(CF$_3$)FCOOH), 95 (CH$_2$=CFCF$_2$), 69 (CF$_3$), 45 (COOH).

EXAMPLE 3

Synthesis of perfluoro(1,1,6,6-tetrahydro-2-trifluoromethyl-3-oxa- 5-hexenol)

(CH$_2$=CFCF$_2$OC—(CF$_3$)FCH$_2$OH)

A three-liter four-necked flask equipped with a stirrer, cooler and dropping funnel was charged with 416 g of methyl perfluoro(6,6-dihydro-6-iodo-2-trifluoromethyl-3-oxahexanoate) obtained in REFERENCE EXAMPLE 2 and 500 mλ of ethanol, and the inside temperature was kept at 0° to 5° C. With stirring, the solution prepared by dissolving 26.5 g of sodium boron hydride (NaBH$_4$) in 600 mλ of ethanol was added dropwise for about 4 hours through the dropping funnel, and during the addition, the inside temperature was kept at 0° to 10° C.

Further after stirring at 0 to 10° C. for two hours, the reaction mixture was slowly poured into 3 liters of 1N-hydrochloric acid. After allowed to stand, an organic layer was collected, rinsed with water, dried and then distilled to obtain 281 g of perfluoro(1,1,6,6-tetrahydro-6-iodo-2-trifluoromethyl-3-oxa-hexanol) (ICH$_2$CF$_2$CF$_2$OC—(CF$_3$)FCH$_2$OH). Boiling point: 75° to 77° C. (5 mmHg).

A 500 mλ four-necked flask equipped with a stirrer, cooler and dropping funnel was charged with 59.2 g of zinc powder and 200 mλ of methanol, and the inside temperature was kept at 60° to 65° C. With stirring, 271 g of the above-mentioned reduced alcohol was added dropwise for about one hour. After completion of the addition, further heating at 60° to 65° C. for one hour followed.

The reaction mixture was treated in the same manner as in EXAMPLE 1 to obtain the titled compound, i.e. perfluoro (1,1,6,6-tetrahydro-2-trifluoromethyl-3-oxa-5-hexenol). Yield: 103 g, boiling point: 76° to 77° C. (95 mmHg).

$^1$H-NMR: δ (ppm) (in CDCl$_3$), 5.47 to 5.30 (2H, m), 5.15 (1H, t.J=6.3 Hz), 4.28 to 4.19 (2H, m).

$^{19}$F-NMR: δ (ppm) (in CDCl$_3$, R-11 internal standard), –71.7 to –72.3 (1 F, m), –73.1 to –73.7 (1 F, m), –81.5 (3 F, s.br), –123.2 to –123.5 (1 F, m), –134.3 to –134.5 (1 F, m).

IR(cm$^{-1}$): 3631 (ν non-associated OH), 3411 (ν associated OH), 1695 (ν c=c).

MS(m/e): 242 (P), 131 (C—(CF$_3$)FCH$_2$OH), 95 (CH$_2$=CFCF$_2$), 69 (CF$_3$), 31 (CH$_2$OH).

EXAMPLE 4

Synthesis of methyl perfluoro(9,9-dihydro-2,5-bistrifluoromethyl-3,6-dioxa-8-nonenoate)

(CH$_2$=CFCF$_2$OC—(CF$_3$)FCF$_2$OC(CF$_3$)FCOOCH$_3$)

A two-liter four-necked flask equipped with a stirrer, cooler and dropping funnel was charged with one liter of methanol and 127 g of zinc powder, followed by a reaction with 873 g of methyl perfluoro(9,9-dihydro-9iodo-2,5-bistrifluoromethyl-3,6-dioxanonanoate) prepared in REFERENCE EXAMPLE 3 in the same manner as in EXAMPLE 1 at 63° to 68° C. After the reaction, the mixture was treated in the same manner as in EXAMPLE 1 to obtain the titled compound, i.e. methyl perfluoro(9,9-dihydro-2,5-bistrifluoromethyl-3,6-dioxa-8-nonenoate). Yield: 482 g, boiling point: 70° to 71° C.(16 mmHg).

$^1$H-NMR: δ (ppm) (in CDCl$_3$), 5.32 to 5.16 (2H, m, J$_{HF}$=47.6, 16.8 Hz), 3.49 (3H, s.br.).

$^{19}$F-NMR: δ (ppm) (in CDCl$_3$, R-11 internal standard), –73.9 to –74.4 (2 F, m), –79.1 to –80.0 (1 F, m), –80.6 (3 F, m), –83.1 (3 F, m), –86.3 to –86.8 (1 F, m), –123.2 to –123.6 (1 F, m, J$_{HF}$=47.6, 16.8 Hz), –132.3 to –132.7 (1 F, m), –146.3 to –146.8 (1 F, m).

IR(cm$^{-1}$): 1790 (νc=o), 1695 (νc=c).

MS(m/e): 436 (P), 325 (P—CF$_2$=CFCF$_2$O), 159 (C—(CF$_3$)FCOOCH$_3$), 95 (CH$_2$=CFCF$_2$), 69 (CF$_3$), 59 (COOCH$_3$), 15 (CH$_3$).

EXAMPLE 5

Synthesis of perfluoro(9,9-dihydro-2,5 -bistrifluoromethyl-3,6-dioxa-8-nonenoic acid)

(CH$_2$=CFCF$_2$OC—(CF$_3$)FCF$_2$OC—(CF$_3$)FCOOH)

A two-liter four-necked flask equipped with a stirrer, cooler and dropping funnel was charged with 43 g of sodium hydroxide and 700 mλ of methanol to dissolve them completely. Afterwards, 403 g of methyl perfluoro(9,9-dihydro-2,5-bistrifluoromethyl-3,6-dioxa-8-nonenoate) prepared in EXAMPLE 4 was subjected to hydrolysis reaction in the same manner as in EXAMPLE 2, and then treated in the same manner as in EXAMPLE 2 to give the titled compound, i.e. perfluoro-(9,9-dihydro-2,5-bistrifluoromethyl-3,6-dioxa-8-nonenoic acid). Yield: 332 g, boiling point: 79° to 80° C. (0.12 mmHg).

$^1$H-NMR: δ (ppm) (in CDCl$_3$), 12.5 (1H, s.br.), 5.60 to 5.30 (2H, m).

$^{19}$F-NMR: δ (ppm) (in CDCl$_3$, R-11 internal standard), –72.7 to –73.0 (2 F, m), –78.2 to –79.2 (1 F, m), –79.7 (3 F, m), –82.3 (3 F, m), –84.1 to –85.0 (1 F, m), –124.1 to –124.4 (1 F, m), –131.1 to –131.3 (1 F, m), –145.3 to –145.7 (1 F, m).

IR(cm$^{-1}$): 3520 (ν non-associated OH), 2650 to 3300 (ν associated OH), 1772 (ν c=o), 1694 (ν c=c).

MS(m/e): 442 (P), 311 (C—(CF$_3$)FCH$_2$C(CF$_3$)FCOOH), 95 (CH$_2$=CFCF$_2$), 69 (CF$_3$), 45 (COOH).

EXAMPLE 6

Synthesis of perfluoro(1,1,9,9-tetrahydro-2,5-bistrifluoromethyl-3,6-dioxa-8-nonenol)

(CH$_2$=CFCF$_2$OC—(CF$_3$)FCF$_2$OC—(CF$_3$)FCH$_2$OH)

Reducing reaction and isolation of methyl perfluoro(9,9-dihydro-9-iodo-2,5-bistrifluoromethyl-3,6dioxanonanoate) of 582 g, which was obtained in REFERENCE EXAMPLE 3, were carried out in the same manner as in EXAMPLE 3 by using sodium boron hydride (NaBH$_4$), to give 365 g of perfluoro(1,1,9,9-tetrahydro-9-iodo-2,5-bistrifluoromethyl-3,6 -dioxanonanol) (ICH$_2$CF$_2$CF$_2$OC(CF$_3$)FCF$_2$OC—(CF$_3$) FCH$_2$OH). Boiling point: 65° to 66° C. (0.4 mmHg).

Subsequently, de-IF reaction and isolation were carried out in the same manner as in EXAMPLE 3 by using 305 g of the reduced alcohol obtained as mentioned above and 46.5 g of zinc powder, to give the titled compound, i.e. perfluoro(1,1,9,9-tetrahydro-2,5-bistrifluoromethyl-3,6-dioxa-8-nonenol). Yield: 351.2 g, boiling point: 77° to 78° C. (14 mmHg).

$^1$H-NMR: δ (ppm) (in CDCl$_3$), 5.31 to 5.12 (2H, m), 4.19 to 4.12 (2H, m), 2.80 (1H, m).

$^{19}$F-NMR: δ (ppm) (in CDCl$_3$, R-11 internal standard), −74.3 to −74.6 (2 F, m), −80.2 to −80.7 (1 F, m), −81.0 (3 F, m), −82.1 to −82.9 (1 F, m), −83.3 (3 F, m), −123.6 to −124.1 (1 F, m), −137.1 to −137.4 (1 F, m), −146.3 to −146.5 (1 F, m).

IR(cm$^{-1}$): 3630 (ν non-associated OH), 3405 (ν associated OH), 1699 (ν c=c).

MS(m/e): 408 (P), 261 (CH$_2$=CFCF$_2$OC—(CF$_3$)CF), 131 (C—(CF$_3$)FCH$_2$OH), 95 (CH$_2$=CFCF$_2$), 69 (CF$_3$), 31 (CH$_2$OH).

EXAMPLE 7
Synthesis of methyl perfluoro(12,12-dihydro-2,5,8-tristrifluoromethyl-3,6,9-trioxa-11-dodecenoate) (CH$_2$=CFCF$_2$OC—(CF$_3$)FCF$_2$OC—(CF$_3$)FCF$_2$OC—(CF$_3$)FCOOCH$_3$)

De-IF reaction in methanol and then isolation were carried out in the same manner as in EXAMPLE 2 by using 187 g of methyl perfluoro(12,12-dihydro-12-iodo-2,5,8-tristrifluoromethyl-3,6,9-trioxadodecanoate) prepared in REFERENCE EXAMPLE 4 and 21.2 g of zinc powder, to give the titled compound, i.e. methyl perfluoro(12,12dihydro-2,5,8-tristrifluoromethyl-3,6,9-trioxa-11-dodecenoate). Yield: 96.3 g, boiling point: 117° to 118° C. (20 mmHg).

$^1$H-NMR: δ (ppm) (in CDCl$_3$), 5.55 (1H, dd, J=15.6, 4.7 Hz), 5.46 (1H, dd, J=42.9, 4.7 Hz), 4.12 (3H, S).

$^{19}$F-NMR: δ (ppm) (in CDCl$_3$, R-11 internal standard), −72.8 to −73.3 (2 F, m), −78.4 to −79.4 (2 F, m), −79.6 to −80.1 (6 F, m), −82.2 to −82.4 (3 F, m), −84.2 to −85.3 (2 F, m), −124.2 to −124.7 (1 F, m), −131.0 to −131.3 (1 F, m), −145.0 to −145.5 (2 F, m).

IR(cm$^{-1}$): 1791 (ν c=o), 1696 (ν c=c).

MS(m/e): 602 (P), 491 (P—CH$_2$=CFCF$_2$), 427 (P—OC—(CF$_3$)FCOOCH$_3$), 325 (C—(CF$_3$)FCF$_2$OC—(CF$_3$)FCOOCH$_3$), 261 (CH$_2$=CFCF$_2$OC—(CF$_3$)FCF$_2$), 159 (C—(CF$_3$)FCOOCH$_3$), 95 (CH$_2$=CFCF$_2$), 69 (CF$_3$), 59 (COOCH$_3$), 15 (CH$_3$).

EXAMPLE 8
Synthesis of perfluoro(12,12-dihydro-2,5,8tristrifluoromethyl-3,6,9-trioxa-11-dodecenoic acid) (CH$_2$=CFCF$_2$OC—(CF$_3$)FCF$_2$OC—(CF$_3$)FCF$_2$OC—(CF$_3$)FCOOH)

Hydrolysis reaction and isolation of 90.3 g of methyl perfluoro(12,12-dihydro-2,5,8-tristrifluoromethyl-3,6,9-trioxa-11-dodecenoate) prepared in EXAMPLE 7 in the same manner as in EXAMPLE 2 by using methanol solution containing 7.6 g of sodium hydroxide were carried out to give the titled compound, i.e. perfluoro(12,12-dihydro-2,5,8-tristrifluoromethyl-3,6,9-trioxa-11-dodecenoic acid). Yield: 59.0 g, boiling point: 110° to 112° C. (0.15 mmHg).

$^1$H-NMR: δ (ppm) 11.72 (1H, br.s.), 5.55 to 5.30 (2H, m).

$^{19}$F-NMR: δ (ppm) (in CDCl$_3$, R-11 internal standard), −72.8 to −73.4 (2 F, m), −78.5 to −79.5 (2 F, m), −79.6 to −80.5 (6 F, m), −82.4 to −82.7 (3 F, m), −83.9 to −85.6 (2 F, m), −124.1 to −124.5 (1 F, m), −130.8 to −131.4 (1 F, m), −145.1 to −145.6 (2 F, m).

IR(cm$^{-1}$): 3533 (ν non-associated OH), 2650 to 3300 (ν associated OH), 1779 (ν c=o), 1696 (ν c=c).

MS(m/e): 588 (P), 427 (P—OC—(CF$_3$)FCOOH), 261 (CH$_2$=CFCF$_2$OC—(CF$_3$)FCF$_2$—), 95 (CH$_2$=CFCF$_2$), 69 (CF$_3$), 45 (COOH).

EXAMPLE 9
Synthesis of ammonium perfluoro(9,9-dihydro-2,5bistrifluoromethyl-3,6-dioxa-8-nonenoate) (CH$_2$=CFCF$_2$OC—(CF$_3$)FCF$_2$OC—(CF$_3$)FCOONH$_4$)

A small amount of perfluoro(9,9-dihydro-2,5bistrifluoromethyl-3,6-dioxa-8-nonenoic acid) prepared in EXAMPLE 5 was dissolved in ethanol, followed by neutralization titration with 0.1N-KOH/ethanol standard solution by using a potentiometric titration equipment. Then the number of base equivalents necessary for neutralizing 1 g of the above-mentioned carboxylic acid was measured, and was 2.42×10$^{-3}$ equivalents.

Subsequently 19.2 g of the same carboxylic acid compound as above was dissolved and neutralized in 46.5 mλ of 1.0N-ammonia water, with measuring its concentration through titration, and the solution was introduced to a 200 mλ measuring flask and water was added to give a solution amounting to 200 mλ. Thus 10% (wt/vol) aqueous solution of the titled compound, i.e. ammonium perfluoro(9,9-dihydro-2,5-bistrifluoromethyl-3,6-dioxa-8-nonenoate) was obtained.

A part of this solution was vacuum-dried repeatedly at 80° C. to give a white solid.

$^1$H-NMR: δ (ppm) (in D$_2$O), 5.41 to 5.14 (2H, m), 4.96 to 4.72 (4H, dr. s.).

$^{19}$F-NMR: δ (ppm) (in D$_2$O, R-11 internal standard), −73.9 to −74.4 (2 F, m), −80.7 to −81.0 (3 F, m), −81.0 to −82.6 (2 F, m), −83.1 to −83.3 (3 F, m), −125.2 to −125.5 (1 F, m), −126.7 to −127.0 (1 F, m), −146.3 to −146.8 (1 F, m).

IR(cm$^{-1}$, KBr method): 3590 to 2700 (ν N—H), 1688 (ν c=c), 1664 (ν c=o).

EXAMPLE 10
Synthesis of ammonium perfluoro(12,12-dihydro-2,5,8-tristrifluoromethyl-3,6,9-trioxa-11-dodecenoate) (CH$_2$=CFCF$_2$OC—(CF$_3$)FCF$_2$OC—(CF$_3$)FCF$_2$OC—(CF$_3$)FCOONH$_4$)

In the same manner as in EXAMPLE 9, 19.4 g of perfluoro(12,12-dihydro-2,5,8-tristrifluoromethyl-3,6,9trioxa-11-dodecenoic acid) prepared in EXAMPLE 8 was mixed with 31.0 mλ of 1N ammonia water to be neutralized, and then the whole of the solution was diluted with water to be 200 mλ to give 10% (wt/vol) aqueous solution of the titled compound, i.e. ammonium perfluoro(12,12-dihydro-2,5,8-tristrifluoromethyl-3,6,9-trioxa-11-dodecenoate).

A part of this solution was vacuum-dried repeatedly at 80° C. to give a white solid.

$^1$H-NMR: δ (ppm) (in D$_2$O), 5.26 to 5.00 (2H, m), 4.92 to 4.74 (4H, br. s.).

$^{19}$F-NMR: δ (ppm) (in D$_2$O, R-11 internal standard), −79.5 to −86.5 (4 F, m), —81.0 to −82.5 (6 F, m), −83.0 to −84.0 (3 F, m), −124.5 to −126.0 (1 F, m), −127.0 to −128.0 (1 F, m), −146.8 to −148.0 (2 F, m).

IR (cm$^{-1}$): 3560–2730 (ν N—H), 1694 (ν c=c), 1661 (ν c=o).

EXAMPLE 11
Use of ammonium perfluoro(9,9-dihydro-2,5bistrifluoromethyl-3,6-dioxa-8-nonenoate) as an emulsifying agent (measurement of critical micelle concentration (hereinafter referred to as cmc))

Ten % aqueous solution of the above-mentioned ammonium salt prepared in EXAMPLE 9 was diluted further with water to prepare solutions having different concentrations, and each surface tension was measured. The results are shown in FIG. 1.

The cmc read from FIG. 1 was 59.2 mmol/liter.

EXAMPLE 12
Use of ammonium perfluoro(12,12-dihydro-2,5,8tristrifluoromethyl-3,6,9-trioxa-11-dodecenoate) as an emulsifying agent (Measurement of cmc)

Surface tensions were measured in the same manner as in EXAMPLE 11 except that the ammonium salt synthesized in EXAMPLE 10 was used instead of the ammonium salt prepared in EXAMPLE 9. The results are shown in FIG. 1.

From FIG. 1, cmc was 8.3 mmol/liter.

The results in FIG. 1 indicate that the respective ammonium salts obtained in EXAMPLES 9 and 10 have a good surface activity and can be used as a reactive emulsifying agent.

EXAMPLE 13

Synthesis of 2,3,3,5,6,6,8-heptafluoro-4,7,10-trioxa-5,8-bistrifluoromethyl12,13-epoxytridecane-1-ene $$(CH_2=CFCF_2OC-(CF_3)FCF_2OC-(CF_3)FCH_2OCH_2CH\underset{O}{\underset{\diagdown\diagup}{CH_2)}}$$

A 300 mλ four-necked flask equipped with a stirrer and cooler was charged with 62.6 g of perfluoro-(1,1,9,9-tetrahydro-2,5-bistrifluoromethyl-3,6-dioxa-8-nonenol) prepared in EXAMPLE 6 and 70.6 g of epichlorohydrin, and heated to 80° C. Then 7.8 g of sodium hydroxide was dividedly added three times over about 30 minutes. During adding, the inside temperature was kept at 80° to 90° C. After stirring at 80° C. for 30 minutes, the mixture was cooled to room temperature.

The reaction mixture was introduced into 500 mλ of pure water, and after allowed to stand, an organic layer was collected, rinsed with water, dried and distilled to give the titled compound, i.e. 2,3,3,5,6,6,8heptafluoro-4,7,10-trioxa-5,8-bistrifluoromethyl-12,13 epoxytridecane-1-ene. Yield: 46.8 g, boiling point: 78° to 80° C. (0.2 mmHg).

$^1$H-NMR: δ (ppm) (in CDCl$_3$), 5.63 to 5.37 (2H, m), 4.40 to 4.19 (2H, m), 4.05 to 3.95 (1H, m), 3.59 to 3.48 (1H, m), 3.20 to 3.09 (1H, m), 2.81 to 2.72 (1H, m), 2.64 to 2.54 (1H, m).

$^9$F-NMR: δ (ppm) (in CDCl$_3$, R-11 internal standard), −72.6 to −73.0 (2 F, m), −79.4 to −79.6 (3 F, m), −79.1 to −80.2 (1 F, m), −80.7 to −81.6 (1 F, m), −82.0 to −82.2 (3 F, m), −124.0 to −124.4 (1 F, m), −132.8 to −133.2 (1 F, m), −145.1 to −145.6 (1 F, m).

IR(cm$^{-1}$): 1695 (ν c=c).

MS(m/e): 464 (P), 421 (P — CHCH$_2$), 369 (P — CH$_2$=CFCF$_2$—),
          $\underset{O}{\diagdown\diagup}$ 277 (CH$_2$=CFCF$_2$O$\overset{\overset{CF_3}{|}}{C}$FCF$_2$O), 187 (—$\overset{\overset{CF_3}{|}}{C}$FCH$_2$OCH$_2$CHCH$_2$),  95 (CH$_2$=CFCF$_2$—),
              $\underset{O}{\diagdown\diagup}$ 69 (CF$_3$),  57 (—CH$_2$CHCH$_2$),
                   $\underset{O}{\diagdown\diagup}$ II. Examples of fluorine-containing polymer with functional group The following abbreviations are used for the fluorine-containing monomer (A) with functional group and other copolymerizing monomer (B), which are used in the present invention N-0-OH: CH$_2$=CFCF$_2$OC—(CF$_3$)FCH$_2$OH (described in EXAMPLE 3)

N-1-OH: CH$_2$=CFCF$_2$OC—(CF$_3$)FCF$_2$OC—(CF$_3$) FCH$_2$OH (described in EXAMPLE 6)

N-0-COOH: CH$_2$=CFCF$_2$OC—(CF$_3$)FCOOH (described in EXAMPLE 2)

N-1-COOH: CH$_2$=CFCF$_2$OC—(CF$_3$)FCF$_2$OC—(CF$_3$) FCOOH (described in EXAMPLE 5)

N-2-COOH: CH$_2$=CFCF$_2$O—[C—(CF$_3$)FCF$_2$O]$_2$—OC—(CF$_3$)FCOOH (described in EXAMPLE 8)

N-1-COONH$_4$: CH$_2$=CFCF$_2$OC—(CF$_3$)FCF$_2$OC—(CF$_3$) FCOONH$_4$ (described in EXAMPLE 9)

N-1-GE: CH$_2$=CFCF$_2$OC—(CF$_3$)FCF$_2$OC—(CF$_3$)FCH$_2$OCH$_2$CHCH$_2$
                                                                    $\underset{O}{\diagdown\diagup}$ (described in EXAMPLE 13)

TFE: Tetrafluoroethylene
VdF: Vinylidene fluoride
HFP: Hexafluoropropylene
CTFE: Chlorotrifluoroethylene
PPVE: Perfluoro(propyl vinyl ether)
PMVE: Perfluoro(methyl vinyl ether)
E: Ethylene Also for the following examples, the abbreviations, symbols and words mentioned below are used.

As catalysts,
IPP: Diisopropyl peroxydicarbonate
NPP: Di-n-propyl peroxydicarbonate
APS: Ammonium persulfate.

As emulsifying agents,
PFOA: Perfluoro octanoic acid ammonium (C$_7$F$_{15}$COONH$_4$).

As solvents,
R-141b: 1,1-dichloro-1-fluoroethane,
R-113: 1,1,2-trichloro-1,2,2-trifluoroethane,
R-114: 1,2-dichloro-1,1,2,2-tetrafluoroethane,
THF: Tetrahydrofuran,
DMF: Dimethylformamide.

For measurement and analysis,
DSC: Differential scanning calory measurement,
Tg: Glass transition temperature,
Tm: Melting point,
Td: Thermal decomposition temperature (assumed to be a temperature at which weight decreases by 1% in air. The temperature at which weight decreases by 1% in air at a heat-up rate of 10° C./min was measured by using a thermal analyser, model DT-30 available from Shimadzu Corporation),
GPC molecular weight: Molecular weight measured by gel permeation chromatograph analysis, which is calculated on the basis of polystyrene (by using THF solvent or DMF solvent),
Mn: Number average molecular weight,
Mw: Weight average molecular weight,
Flow rate: After preheating for 5 minutes, a volume per unit time (mλ/sec) of a copolymer flowing through a 2 mm diameter and 8 mm long nozzle was measured by using a flow tester, and the measured value is a flow rate.

EXAMPLE 14

Copolymerization of perfluoro(1,1,9,9-tetrahydro-2,5-bistrifluoromethyl-3,6-dioxa-8-nonenol) and tetrafluoroethylene A 250 mλ autoclave equipped with a valve, pressure gauge and thermometer was charged with 16.3 g of perfluoro(1,1,9,9-tetrahydro-2,5-bistrifluoromethyl-3, 6dioxa-8-nonenol) prepared in EXAMPLE 6, 60 g of 1,1-dichloro-1-fluoroethane (R-141b) and 0.10 g of diisopropyl peroxydicarbonate (IPP) as shown in TABLE 1, and was cooled with dry ice/methanol solution. Then the inside of the system was replaced by nitrogen sufficiently. Afterwards 6.3 g of tetrafluoroethylene (TFE) was fed through the valve to react at 45° C. for 20 hours with shaking.

TABLE 1

| Reaction conditions | Ex. 14 | Ex. 15 | Ex. 16 | Ex. 17 | Ex. 18 |
|---|---|---|---|---|---|
| Functional group-containing monomer (A) | N-1-OH | N-1-OH | N-1-OH | N-0-OH | N-1-COOH |
| Charged amount (g) | 16.3 | 2.4 | 20.4 | 1.1 | 2.6 |
| Monomer (B) Charged amount | | | | | |
| TFE (g) | 6.3 | — | — | — | — |
| VdF (g) | — | 4.5 | 4.5 | 6.9 | 9.4 |
| Initiator | IPP | IPP | IPP | IPP | IPP |
| Charged amount (g) | 0.10 | 0.08 | 0.13 | 0.12 | 0.16 |
| Solvent | R-141b | R-141b | R-141b | R-113 | R-113 |
| Charged amount (g) | 60 | 60 | 60 | 40 | 40 |
| Reaction temperature (° C.) | 45 | 45 | 45 | 45 | 45 |
| Reaction time (hr) | 20 | 20 | 20 | 17 | 19 |

With proceeding of the reaction, the gauge pressure before the reaction, i.e. 4.3 kg/cm²G decreased to 2.1 kg/cm²G. After discharging the un-reacted monomer, the precipitated solid was taken out, dissolved in acetone and precipitated again by using hexane to separate the copolymer. Vacuum drying was carried out until reaching a constant weight, and 4.1 g of the copolymer was obtained.

The composition of the obtained copolymer was confirmed by $^1$H-NMR and $^{19}$F-NMR analysis, and the presence of the functional groups by infrared absorption spectrum.

Also the molecular weight of the copolymer was measured by GPC which was calculated on the basis of polystyrene, the glass transition temperature (Tg) by DSC, and the thermal decomposition temperature by thermogravimetric measurement. The results are shown in TABLE 2.

EXAMPLES 15 TO 18

Copolymerization of fluorine-containing monomer with functional group and vinylidene fluoride Copolymers were obtained in the same manner as in EXAMPLE 14 except that the monomers, initiators and solvents (and weights thereof) were changed to those described in TABLE 1.

After completion of the reaction, the copolymers of EXAMPLES 15 and 16 were separated in the same manner as in EXAMPLE 14, and the copolymers of EXAMPLES 17 and 18 were obtained by rinsing the obtained white powder with water, cleaning with methanol and then vacuum-drying. The results of measuring the yield, composition by NMR analysis, thermal analysis (Tg, Tm, Td) and molecular weight of each copolymer are shown in TABLE 2.

TABLE 2

| Results of polymerization | Ex. 14 | Ex. 15 | Ex. 16 | Ex. 17 | Ex. 18 |
|---|---|---|---|---|---|
| Yield (g) | 4.1 | 4.5 | 4.5 | 7.3 | 15.8 |
| Composition of polymer | | | | | |
| Functional group-containing monomer (A) | N-1-OH | N-1-OH | N-1-OH | N-0-OH | N-1-COOH |
| (% by mole) | 73.3 | 15.8 | 51.8 | 0.5 | 0.9 |
| Monomer (B) (% by mole) | | | | | |
| TFE | 26.7 | — | — | — | — |
| VdF | — | 84.2 | 48.2 | 99.5 | 99.1 |
| DSC measurement (° C.) | | | | | |
| Tg | −1.1 | −8.9 | −8.1 | — | — |
| Tm | — | — | — | 171.7 | 172 |
| Thermal decomposition temperature when weight decreased by 1% (° C.) | | | | | |
| Td | 204.7 | 351 | 341 | 358 | 297 |
| Molecular weight by GPC × 10⁴ (THF type$^{1)}$, DMF type$^{2)}$) | | | | | |
| Mn | 1.8$^{1)}$ | 1.8$^{1)}$ | 1.2$^{1)}$ | 7.1$^{2)}$ | 7.4$^{2)}$ |
| Mw | 3.0 | 2.9 | 2.4 | 12.4 | 14.8 |
| IR analysis (cm⁻¹) | | | | | |
| ν non-associated OH | 3656 | 3645 | 3640 | 3622 | 3685 to 2800 |
| ν associated OH | 3466 | 3440 | 3425 | 3455 | |
| ν C=O | — | — | — | — | 1770 |

EXAMPLE 19

Copolymerization of perfluoro(1,1,6,6-tetrahydro-2-trifluoromethyl-3-oxa-5-hexenol) and tetrafluoroethylene/ethylene A 500 mλ autoclave equipped with a valve, pressure gauge and thermometer was charged with 1.4 g of perfluoro (1,1,6,6-tetrahydro-2-trifluoromethyl-3-oxa-5hexenol) prepared in EXAMPLE 3, 100 g of 1,1,2-trichloro-1,2,2-trifluoroethane (R-113) and 0.13 g of diisopropyl peroxydicarbonate (IPP) as shown in TABLE 3, and was cooled with dry ice/methanol solution. Then the inside of the system was replaced by nitrogen sufficiently. Subsequently 30.3 g of a monomer mixture prepared by pre-mixing tetrafluoroethylene and ethylene in a molar ratio of 80:20 in a bomb was fed through the valve to react at 45° C. for 1.5 hours with shaking.

With proceeding of the reaction, the gauge pressure before the reaction, i.e. 12.0 kgf/cm²G decreased to 7.5 kgf/cm²G. The un-reacted monomer was discharged, and the precipitated white solids in the form of powder were taken out, rinsed with water, cleaned with acetone and vacuum-dried to give 15.6 g of a copolymer.

The composition of the obtained copolymer was confirmed by $^{19}$F-NMR and elementary analysis, and the presence of functional groups by infrared absorption spectrum.

Also the melting point of the copolymer was measured by DSC, and the flow rate by a flow tester. The results are shown in TABLE 4.

EXAMPLES 20 TO 26

Copolymerization of the fluorine-containing monomer (A) with functional group and the monomer mixture containing the fluorine-containing monomer (B)

The copolymers were prepared in the same manner as in EXAMPLE 19 except that the composition of the fluorine-containing monomer (A) with functional group and the monomer mixture containing the monomer (B) (and charged weights thereof), initiators and solvents (and charged weights thereof) and reaction time were changed to the monomer (A), the monomer mixture comprising the monomer (B) (and weights thereof), initiators and solvents (and weights thereof) which are described in TABLE 3.

For EXAMPLES 20, 21 and 22, the copolymers after completion of the reaction were separated in the same manner as in EXAMPLE 19; for EXAMPLE 23 in the same manner as in EXAMPLE 17; and for EXAMPLES 24, 25 and 26 in the same manner as in EXAMPLE 14.

The composition, thermal analysis and flow rate or measurement of molecular weight by GPC of the copolymers prepared in EXAMPLES 20 to 26 are shown in TABLE 4.

TABLE 3

| Reaction conditions | Ex. 19 | Ex. 20 | Ex. 21 | Ex. 22 | Ex. 23 | Ex. 24 | Ex. 25 | Ex. 26 |
| --- | --- | --- | --- | --- | --- | --- | --- | --- |
| Functional group-containing monomer (A) | N-0-OH | N-1-OH | N-1-OH | N-1-COOH | N-1-OH | N-0-OH | N-1-OH | N-1-GE |
| Charged amount (g) | 1.4 | 2.1 | 2.1 | 2.2 | 1.54 | 1.64 | 1.84 | 2.86 |
| Monomer (B) | | | | | | | | |
| Composition of monomer mixture (% by mole) | | | | | | | | |
| TFE | 80 | 80 | 52 | 80 | 20 | 20 | 14 | 20 |
| VdF | — | — | — | — | 80 | 60 | 74 | 60 |
| HFP | — | — | — | — | — | 20 | — | 20 |
| CTFE | — | — | — | — | — | — | 12 | — |
| E | 20 | 20 | 48 | 20 | — | — | — | — |
| Charged amount of monomer mixture (g) | 30.3 | 33.8 | 23.8 | 33.5 | 17.8 | 33.6 | 16.3 | 34.6 |
| Initiator | IPP | IPP | IPP | IPP | IPP | IPP | IPP | IPP |
| Charged amount (g) | 0.13 | 0.13 | 0.13 | 0.14 | 0.10 | 0.18 | 0.11 | 0.16 |
| Solvent | R-113 | R-113 | R-113 | R-113 | R-113 | R-113 | R-113 | R-113 |
| Charged amount (g) | 100 | 100 | 100 | 100 | 100 | 100 | 100 | 100 |
| Reaction temperature (° C.) | 45 | 45 | 45 | 45 | 45 | 45 | 45 | 45 |
| Reaction time (hr) | 1.5 | 4.0 | 5.0 | 2.0 | 20 | 17 | 20 | 5.0 |

TABLE 4

| Results of polymerization | Ex. 19 | Ex. 20 | Ex. 21 | Ex. 22 | Ex. 23 | Ex. 24 | Ex. 25 | Ex. 26 |
| --- | --- | --- | --- | --- | --- | --- | --- | --- |
| Yield (g) | 15.6 | 16.0 | 12.5 | 13.0 | 13.2 | 13.8 | 11.6 | 20.2 |
| Composition of polymer | | | | | | | | |
| Functional group-containing monomer (A) | N-0-OH | N-1-OH | N-1-OH | N-1-COOH | N-1-OH | N-0-OH | N-1-OH | N-1-GE |
| (% by mole) | 2.4 | 1.8 | 2.5 | 3.7 | 0.4 | 0.3 | 2.4 | 7.0 |
| Monomer (B) (% by mole) | | | | | | | | |
| TFE | 67.4 | 72.5 | 49.0 | 62.3 | 19.8 | 25.7 | 14.2 | 24.0 |
| VdF | — | — | — | — | 79.8 | 66.8 | 64.1 | 64.0 |
| HFP | — | — | — | — | — | 7.2 | — | 5.0 |
| CTFE | — | — | — | — | — | — | 19.3 | — |
| E | 30.2 | 25.7 | 48.5 | 34.0 | — | — | — | — |
| DSC measurement (° C.) | | | | | | | | |
| Tg | — | — | — | — | — | — | −16 | — |
| Tm | 235 | 252 | 258 | 223 | 133 | 109 | — | 94 |
| Thermal decomposition temperature when weight decreased by 1% (° C.) | | | | | | | | |
| Td | 350 | 384 | 366 | 272 | 374 | 359 | 367 | 283 |
| Molecular weight by GPC × $10^4$ (THF) | | | | | | | | |
| Mn | — | — | — | — | 7.5 | 7.1 | 7.6 | 6.5 |

TABLE 4-continued

| Results of polymerization | Ex. 19 | Ex. 20 | Ex. 21 | Ex. 22 | Ex. 23 | Ex. 24 | Ex. 25 | Ex. 26 |
|---|---|---|---|---|---|---|---|---|
| Mw | — | — | — | — | 21.3 | 12.1 | 13.9 | 11.5 |
| Flow rate[1] (ml/sec) | $5.3 \times 10^{-2}$ | $4.1 \times 10^{-2}$ | $3.9 \times 10^{-3}$ | $3.2 \times 10^{-2}$ | — | — | — | — |
| IR analysis ($cm^{-1}$) | | | | | | | | |
| ν non-associated OH | 3633 | 3633 | 3634 | 3680 to | 3628 | 3624 | 3633 | — |
| ν associated OH | 3478 | 3489 | 3481 | 2800 | 3442 | 3441 | 3456 | — |
| ν C=O | — | — | — | 1716 | — | — | — | — |

[1]Measured at 300° C. under 7 kg load

EXAMPLE 27

Copolymerization of perfluoro(1,1,9,9-tetrahydro-2,5-bistrifluoromethyl-3,6-dioxa-8-nonenol) and tetrafluoroethylene/ethylene monomer mixture A one-liter stainless steel autoclave equipped with a stirrer, valve, pressure gauge and thermometer was charged with 250 mλ of pure water and 0.16 g of perfluoro(1,1,9,9-tetrahydro-2,5-bistrifluoromethyl-3,6-dioxa-8-nonenol) prepared in EXAMPLE 6 as shown in TABLE 5, and the inside of the system was replaced sufficiently with nitrogen gas, and was evacuated. Then the autoclave was charged with 250 g of 1,2-dichloro-1,1,2,2-tetrafluoroethane (R-114) and 1.0 g of cyclohexane, and the inside of the system was kept at 35° C.

With stirring, the monomer mixture of tetrafluoroethylene/ethylene (molar ratio 82/18) prepared by pre-mixing in a bomb was fed under pressure to the autoclave so that the inside pressure thereof becomes 8.0 kgf/cm²G. Subsequently 2.0 g of 50% methanol solution of di-n-propyl peroxydicarbonate was fed under pressure to initiate the reaction.

With proceeding of the polymerization, the pressure lowered, and therefore at the time when reached 7.5 kgf/cm²G, the reaction pressure was again raised to 8.0 kgf/cm²G with the monomer mixture comprising tetrafluoroethylene/ethylene (molar ratio 52/48) which was separately prepared by mixing in a bomb. Then lowering and raising of the pressure were repeated, and the monomer mixture of tetrafluoroethylene/ethylene (molar ratio 52/48) was fed.

Further with continuing feeding of the monomer mixture, every time when about 2.5 g of the monomer mixture was consumed after the initiation of the polymerization, 0.08 g of the above-mentioned fluorine-containing monomer (N-1-OH) with hydroxyl group was fed under pressure nine times (0.72 g in total) to continue the polymerization. When the consumption of the monomer mixture reached about 25 g, that is to say, after a time lapse of 1.5 hours from the initiation of the polymerization, the feeding of the monomer mixture was stopped, the autoclave was cooled, and the un-reacted monomer and R-114 were discharged. White powder of 25.6 g was obtained by treating in the same manner as in EXAMPLE 18.

The composition of the obtained copolymer was confirmed by $^{19}$F-NMR and elementary analysis, and the presence of the functional groups by infrared absorption spectrum.

Also the melting point of the copolymer was measured by DSC, and the flow rate by a flow tester. The results are shown in TABLE 6.

EXAMPLES 28 to 31

Copolymerization of the fluorine-containing monomer (A) with functional group and tetrafluoroethylene/ethylene monomer mixture Copolymers were prepared in the same manner as in EXAMPLE 27 except that the fluorine-containing monomer (A) and its charged amount, and the amounts of the monomer mixture comprising the monomer (B), initiator and cyclohexane were changed to those mentioned in TABLE 5.

The composition, thermal analysis and flow rate of the copolymers obtained in the respective EXAMPLES are shown in TABLE 6.

EXAMPLE 32

Copolymerization of perfluoro(1,1,9,9-tetrahydro-2,5-bistrifluoromethyl-3,6-dioxa-8-nonenol) and tetrafluoroethylene/ethylene monomer mixture A copolymer was prepared in the same manner as in EXAMPLE 27 under the conditions shown in TABLE 5 except that a six-liter stainless steel autoclave equipped with a stirrer, valve, pressure gauge and thermometer was used, and that there were used 1,500 mλ of pure water and 1,500 g of 1,2-dichloro-1,1,2,2-tetrafluoroethane (R-114) as a solvent. The composition, thermal analysis and flow rate of the copolymer are shown in TABLE 6.

TABLE 5

| Reaction conditions | Ex. 27 | Ex. 28 | Ex. 29 | Ex. 30 | Ex. 31 | Ex. 32 |
|---|---|---|---|---|---|---|
| Functional group-containing monomer (A) | N-1-OH | N-1-OH | N-1-OH | N-1-COOH | N-1-COOH | N-1-OH |
| Initial charge (g) | 0.16 | 0.16 | 0.3 | 0.16 | 0.31 | 1.89 |
| Additional charge (g) | 0.08 × 9 times | 0.08 × 9 times | 0.15 × 9 times | 0.08 × 9 times | 0.16 × 9 times | 0.94 × 9 times |
| Monomer (B) | | | | | | |
| TFE/E molar ratio at initial charge | 82/18 | 82/18 | 82/18 | 82/18 | 82/18 | 82/18 |
| TFE/E molar ratio at additional charge | 52/48 | 52/48 | 52/48 | 52/48 | 52/48 | 52/48 |
| Initiator | NPP | NPP | NPP | NPP | NPP | NPP |

TABLE 5-continued

| Reaction conditions | Ex. 27 | Ex. 28 | Ex. 29 | Ex. 30 | Ex. 31 | Ex. 32 |
|---|---|---|---|---|---|---|
| Charged amount (g) | 1.0 | 1.0 | 1.0 | 1.0 | 1.0 | 6.0 |
| Cyclohexane (g) | 1.0 | 1.6 | 1.6 | 1.0 | 1.6 | 9.6 |
| Reaction temperature (° C.) | 35 | 35 | 35 | 35 | 35 | 35 |
| Reaction time (hr) | 1.5 | 1.2 | 1.4 | 1.5 | 2.0 | 1.6 |

TABLE 6

| Results of polymerization | Ex. 27 | Ex. 28 | Ex. 29 | Ex. 30 | Ex. 31 | Ex. 32 |
|---|---|---|---|---|---|---|
| Yield (g) | 25.6 | 22.2 | 27.5 | 33.0 | 50.5 | 222.8 |
| Composition of polymer | | | | | | |
| Functional group-containing monomer (A) (% by mole) | N-1-OH 0.2 | N-1-OH 0.2 | N-1-OH 0.4 | N-1-COOH 0.2 | N-1-COOH 0.5 | N-1-OH 0.4 |
| Monomer (B) (% by mole) | | | | | | |
| TFE | 56.3 | 54.9 | 54.9 | 55.0 | 55.2 | 56.8 |
| E | 43.5 | 44.9 | 44.7 | 44.8 | 44.3 | 42.8 |
| Melting point (° C.) | 275 | 277 | 274 | 277 | 274 | 272 |
| Thermal decomposition temperature when weight decreased by 1% (° C.) | 359 | 361 | 377 | 368 | 336 | 387 |
| Flow rate[1] (ml/sec) | $4.3 \times 10^{-3}$ | $2.7 \times 10^{-2}$ | $3.0 \times 10^{-2}$ | $4.0 \times 10^{-3}$ | $2.5 \times 10^{-2}$ | $3.1 \times 10^{-1}$ |
| IR analysis (cm$^{-1}$) | | | | | | |
| ν non-associated OH | 3644 | 3644 | 3636 | 3680 | 3680 | 3645 |
| ν associated OH | 3356 | 3350 | 3365 | to 2800 | to 2800 | 3360 |
| ν C=O | — | — | — | 1789 | 1789 | — |

[1] Measured at 300° C. under 7 kg load

EXAMPLE 33

Copolymerization of perfluoro(1,1,9,9-tetrahydro-2,5-bistrifluoromethyl-3,6-dioxa-8-nonenol), tetrafluoroethylene and perfluoro(propyl vinyl ether)

A six-liter autoclave lined with glass and equipped with a stirrer, valve, pressure gauge and thermometer was charged with 1,500 mλ of pure water, followed by replacing with nitrogen gas sufficiently, and then was evacuated. Then 1,500 g of 1,1-dichloro-1,1,2,2tetrafluoroethane (R-114) was fed thereto. Afterwards as shown in TABLE 7, 2.4 g of perfluoro(1,1,9,9-tetrahydro-2,5-bistrifluoromethyl-3,6-dioxa-8-nonenol) prepared in EXAMPLE 6, 30 g of perfluoro(propyl vinyl ether) (PPVE) and 210 g of methanol were fed under pressure by using nitrogen gas, and the inside of the system was kept at a temperature of 35° C.

With stirring, tetrafluoroethylene gas was fed under pressure so that the inside pressure becomes 8.0 kgf/cm²G. Subsequently 2.4 g of 50% methanol solution of di-n-propyl peroxydicarbonate was fed under pressure to initiate the reaction.

With proceeding of the polymerization, the pressure lowered, and therefore at the time when decreased to 7.5 kgf/cm²G, the reaction pressure was raised to 8.0 kgf/cm²G again with tetrafluoroethylene gas, and lowering and raising of the pressure were repeated.

With continuing feeding of tetrafluoroethylene, after the initiation of the polymerization, every time when about 60 g of tetrafluoroethylene gas was consumed, 1.2 g of the above-mentioned fluorine-containing monomer (N-1-OH) with hydroxyl group and 3.3 g of perfluoro(propyl vinyl ether) were fed under pressure 9 times respectively (N-1-OH totaling 10.8 g, perfluoro(propyl vinyl ether) 29.7 g in total) to continue the polymerization. At the time when about 600 g of tetrafluoroethylene was consumed from the initiation of the polymerization, that is, 5 to 6 hours after, the feeding of tetrafluoroethylene was stopped and the autoclave was cooled. Then the un-reacted monomer and R-114 were discharged.

White powder of 642 g was obtained by treating in the same manner as in EXAMPLE 18. The composition of the obtained copolymer was confirmed by $^{19}$F-NMR, and the presence of the functional groups by infrared absorption spectrum.

Also the melting point of the copolymer was measured by DSC, and the flow rate by a flow tester.

The results are shown in Table 7.

EXAMPLES 34 AND 35

Copolymerization of perfluoro(9,9-dihydro-2,5bistrifluoromethyl-3,6-dioxa-8-nonenol), tetrafluoroethylene and perfluoro(propyl vinyl ether)

Polymers were obtained in the same manner as in EXAMPLE 33 except that the charged amounts of the fluorine-containing monomer (N-1-OH) with hydroxyl group and perfluoro(propyl vinyl ether), and the amounts of an initiator and methanol were changed to those mentioned in TABLE 7, and then measurements were made in the same manner as in EXAMPLE 33.

The results are shown in TABLE 7.

TABLE 7

| Conditions Results | Ex. 33 | Ex. 34 | Ex. 35 |
|---|---|---|---|
| Functional group-containing monomer (A) | N-1-OH | N-1-OH | N-1-OH |
| Initial charge (g) | 2.4 | 2.6 | 5.0 |

TABLE 7-continued

| Conditions Results | Ex. 33 | Ex. 34 | Ex. 35 |
|---|---|---|---|
| Additional charge (g) | 1.2 × 9 times | 3.6 × 9 times | 3.7 × 9 times |
| Monomer B | | | |
| Pressure for continuous charging of TFE (kgf/cm$^2$G) | 7.5–8.0 | 7.5–8.0 | 7.5–8.0 |
| PPVE[1] Initial charge (g) | 30.0 | 48.6 | 50.3 |
| PPVE Additional charge (g) | 3.3 × 9 times | 1.3 × 9 times | 2.5 × 9 times |
| Initiator | NPP | NPP | NPP |
| Charged amount (g) | 2.4 | 2.4 | 2.4 |
| Methanol (g) | 210 | 120 | 120 |
| Reaction temperature (° C.) | 35 | 35 | 35 |
| Reaction time (hr) | 5.6 | 5.5 | 8.0 |
| Yield (g) | 642 | 671 | 652 |
| Composition of polymer (% by mole) | | | |
| Functional group-containing monomer (A) | 0.4 | 0.6 | 1.0 |
| Monomer (B) | | | |
| TFE | 99.2 | 99.1 | 98.5 |
| PPVE | 0.4 | 0.3 | 0.5 |
| Melting point (° C.) | 311 | 309 | 308 |
| Thermal decomposition temperature when weight decreased by 1% (° C.) | 369 | 362 | 384 |
| Flow rate (ml/sec)[2] | 2.9 × 10$^{-3}$ | 1.4 × 10$^{-3}$ | 1.7 × 10$^{-3}$ |
| IR analysis (cm$^{-1}$) | | | |
| ν non-associated OH | 3644 | 3651 | 3651 |
| ν associated OH | 3549 | 3549 | 3524 |

[1]PPVE: Perfluoro(propyl vinyl ether)
[2]Measured at 372° C. under 7 kg load

EXAMPLE 36
Emulsion copolymerization of perfluoro(1,1,9,9tetrahydro-2,5-bistrifluoromethyl-3,6-dioxa-8-nonenol) and monomer mixture of vinylidene fluoride/tetrafluoroethylene/hexafluoropropylene A one-liter autoclave made of glass and equipped with a stirrer, valve, pressure gauge and thermometer was charged with 500 mλ of pure water, 1.0 g of ammonium perfluorooctanoate (PFOA) as an emulsifying agent and 0.5 g of perfluoro(1,1,9,9-tetrahydro-2,5-bistrifluoromethyl-3,6-dioxa-8-nonenol) prepared in EXAMPLE 6 as shown in TABLE 8, and, after the inside of the system was sufficiently replaced by nitrogen gas, the system was heated to 60° C.

Subsequently, with stirring, the monomer mixture of vinylidene fluoride/tetrafluoroethylene/hexafluoropropylene (molar ratio 60/20/20) which had been previously prepared by mixing in a bomb was fed under pressure so that the inside pressure became 8.0 kgf/cm$^2$G at 60° C. Then the solution prepared by dissolving 0.5 g of ammonium persulfate (APS) in 5.0 mλ of pure water was fed under pressure with nitrogen gas to initiate the reaction.

Since the pressure decreased with proceeding of the polymerization, at the time when lowered to 7.5 kgf/cm$^2$G, the reaction pressure was again raised to 8.0 kgf/cm$^2$G by using the same VdF/TFE/HFP monomer mixture (molar ratio 60/20/20) as mentioned above. Thus lowering and raising of the pressure were repeated.

Further, with continuing feeding of the monomer mixture, every time when about 25 g of the monomer mixture was consumed after the initiation of the polymerization, 0.24 g of the above-mentioned fluorine-containing monomer (N-1-OH) with hydroxyl group was fed under pressure 7 times (1.68 g in total) to continue the polymerization. At the time when about 200 g of the monomer mixture was consumed from the initiation of the polymerization, that is, 7.5 hours after, the above-mentioned autoclave was cooled and the un-reacted monomer was discharged to give an aqueous emulsion.

This aqueous emulsion was freezed, and the resulting coagulate was rinsed with water and dried to give 189 g of the rubber-like polymer.

The composition of the obtained copolymer was confirmed by $^1$H-NMR and $^{19}$F-NMR, and the presence of the functional groups by infrared absorption spectrum.

Also the glass transition point (Tg) of the copolymer was measured by DSC, and the molecular weight by GPC analysis on the basis of the THF solvent.

The results are shown in TABLE 9.

EXAMPLES 37 TO 42
Emulsion polymerization of a fluorine-containing monomer (A) with functional group and a monomer mixture mainly comprising vinylidene fluoride Copolymers were prepared in the same manner as in EXAMPLE 36 except that the kind, initial charge, additional charge and the number of additional charges of the fluorine-containing monomer (A) with functional group, the composition of the monomer mixture comprising the monomer (B), initiator, emulsifying agent, reaction temperature and reaction time were changed to the monomer (A), its initial charge, additional charge and the number of additional charges, the monomer mixture of the monomer (B), initiator, emulsifying agent and the polymerization temperature and time as shown in TABLE 8.

The results of measuring the composition of the copolymers obtained in EXAMPLES 37 to 42, thermal analysis and molecular weight by GPC are shown in TABLE 9.

TABLE 8

| Reaction conditions | Ex. 36 | Ex. 37 | Ex. 38 | Ex. 39 | Ex. 40 | Ex. 41 | Ex. 42 |
|---|---|---|---|---|---|---|---|
| Functional group-containing monomer (A) | N-1-OH | N-1-OH | N-1-OH | N-1-OH | N-1-OH | N-1-COOH | N-1-COONH$_4$ |
| Initial charge (g) | 0.50 | 2.15 | 1.13 | 4.98 | 4.89 | 2.20 | 2.5 |
| Additional charge (g) | 0.24 × 7 times | 0.60 × 5 times | 0.60 × 5 times | 1.65 × 5 times | — | 1.15 × 5 times | — |
| Monomer (B) | | | | | | | |
| Composition of monomer mixture (% by mole) | | | | | | | |
| VdF | 60 | 60 | 60 | 60 | 60 | 60 | 74 |
| TFE | 20 | 20 | 20 | 20 | 20 | 20 | 14 |
| HFP | 20 | 20 | 20 | 20 | 20 | 20 | — |
| CTFE | — | — | — | — | — | — | 12 |
| Emulsifying agent | PFOA | PFOA | PFOA | PFOA | PFOA | PFOA | — |

TABLE 8-continued

| Reaction conditions | Ex. 36 | Ex. 37 | Ex. 38 | Ex. 39 | Ex. 40 | Ex. 41 | Ex. 42 |
|---|---|---|---|---|---|---|---|
| Charged amount (g) | 1.0 | 1.0 | 1.0 | 1.0 | 1.0 | 1.0 | — |
| Initiator | APS | APS | APS | APS | APS | APS | APS |
| Charged amount (g) | 0.5 | 0.5 | 0.5 | 0.5 | 0.5 | 0.5 | 0.2 |
| Reaction temperature (° C.) | 60 | 80 | 60 | 80 | 60 | 80 | 60 |
| Reaction time (hr) | 7.5 | 5.8 | 9.1 | 11.0 | 4.5 | 4.8 | 2.5 |

TABLE 9

| Results of polymerization | Ex. 36 | Ex. 37 | Ex. 38 | Ex. 39 | Ex. 40 | Ex. 41 | Ex. 42 |
|---|---|---|---|---|---|---|---|
| Yield (g) | 189 | 134 | 144 | 141 | 26.1 | 147 | 25.1 |
| Composition of polymer | | | | | | | |
| Functional group-containing monomer (A) | N-1-OH | N-1-OH | N-1-OH | N-1-OH | N-1-OH | N-1-COOH | N-1-COONH$_4$ |
| (% by mole) | 0.1 | 0.5 | 0.4 | 1.3 | 2.5 | 0.4 | 0.7 |
| Monomer (B) (% by mole) | | | | | | | |
| VdF | 62.8 | 63.0 | 62.4 | 63.1 | 66.3 | 63.5 | 72.2 |
| TFE | 18.0 | 18.5 | 19.7 | 18.1 | 20.4 | 18.1 | 13.7 |
| HFP | 19.1 | 18.0 | 17.5 | 17.5 | 10.8 | 18.0 | — |
| CTFE | — | — | — | — | — | — | 13.4 |
| Measurement by DSC (° C.) | | | | | | | |
| Tg | −17.0 | −20.8 | −47.0 | −21.5 | −23.0 | −17.5 | — |
| Tm | — | — | — | — | — | — | 80.6 |
| Thermal decomposition temperature when weight decreased by 1% (° C.) | | | | | | | |
| Td | 380 | 405 | 369 | 395 | 395 | 353 | 356 |
| Molecular weight by GPC × 10$^4$ (THF) | | | | | | | |
| Mn | 21.4 | 7.1 | 21.6 | 5.1 | 6.5 | 9.2 | 28.5 |
| Mw | 50.1 | 12.7 | 47.4 | 8.1 | 14.5 | 14.2 | 78.0 |
| IR analysis (cm$^{-1}$) (cast film) | | | | | | | |
| ν non-associated OH | — | — | — | — | — | 3580 to | 3490 to |
| ν associated OH | 3302 | 3300 | 3301 | 3301 | 3300 | 2650 | 2630(ν NH) |
| ν C=O | — | — | — | — | — | 1770 | 1669 |

EXAMPLE 43

Copolymerization of perfluoro(9,9-dihydro-2,5bistrifluoromethyl-3,6-dioxa-8-nonenoic acid) and monomer mixture of tetrafluoroethylene/perfluoro(methyl vinyl ether)

A six-liter stainless steel autoclave equipped with a stirrer, valve, pressure gauge and thermometer was charged with 1,000 me of pure water, 2.0 g of perfluoro(9,9-dihydro-2,5-bistrifluoromethyl-3,6-dioxa-8-nonenoic acid) (N-1-COOH) prepared in EXAMPLE 5 and 1.04 g of 1,4-diiodoperfluorobutane (ICF$_2$CF$_2$CF$_2$CF$_2$I), and was heated to 80° C. after the inside of the system was replaced by nitrogen gas sufficiently.

Subsequently, with stirring, the monomer mixture of tetrafluoroethylene/perfluoro(methyl vinyl ether) (PMVE) (molar ratio 63/37) which had been previously prepared by mixing in a bomb, was fed under pressure so that the inside pressure becomes 8.0 kgf/cm$^2$G at 80° C. Then the solution prepared by dissolving 0.25 g of ammonium persulfate (APS) in 5.0 mλ of pure water was fed under pressure with nitrogen gas to initiate the reaction.

Since the pressure decreased with proceeding of the polymerization, at the time when lowered to 7.5 kgf/cm$^2$G, the reaction pressure was again raised to 8.0 kgf/cm$^2$G by using the same TFE/PMVE (molar ratio 63/37) monomer mixture as mentioned above. Thus lowering and raising of the pressure were repeated.

At the time when about 200 g of the monomer mixture was consumed from the initiation of the polymerization, that is, 21 hours after, the feeding of the monomer mixture was stopped, the above-mentioned autoclave was cooled and the un-reacted monomer was discharged to give an aqueous emulsion.

This aqueous emulsion was freezed, and the resulting coagulate was rinsed with water and dried to give 198 g of the rubber-like polymer.

The composition of the obtained copolymer was TFE/PMVE/N-1-COOH=59.8/39.8/0.4 (% by mole) by $^1$H-NMR and $^{19}$F-NMR analyses. At 1,780 cm$^{-1}$ of the infrared spectrum, the characteristic absorption of —C=O was observed, and at 2,640 to 3,580 cm$^{-1}$, the characteristic absorptions of —OH were observed. The glass transition temperature (Tg) was −3.4° C., and the thermal decomposition temperature Td when the weight decreased by 1% was 359° C. Mooney viscosity (100° C.) was ML$_{1+10}$ 60.

III. Examples of thermoplastic resin composition

For the following examples, the tests mentioned below were carried out.

(1) Tensile test

Measurements were made in accordance with ASTM D638 at a cross-head speed of 10 mm/min at room temperature by using a type 5 dumbbell and a TENSILON universal tester available from Orientec Corporation.

(2) Bending test

Measurements were made in accordance with JIS K-6911 at a bending speed of 2 mm/min at room temperature by using a TENSILON universal tester available from Orientec Corporation.

(3) Izod impact test

Izod notched impact strength was measured in accordance with ASTM D256 by using a U-F impact tester available from Ueshima Seisakusho Ltd.

(4) Deflection temperature under load

Measurements were made in accordance with JIS K7207 under $N_2$ gas flow under a load of 18.5 kgf/cm$^2$ at the heat-up rate of 2° C./min by using a heat distortion tester available from Yasuda Seiki Seisakusho Ltd.

(5) Melt flow rate

Melt flow rate (g/10 min) was measured after preheating for 5 minutes by using a 2 mm diameter and 8 mm long nozzle and a flow tester available from Shimadzu Corporation.

(6) Hardness

Measurements were made in accordance with ASTM D2240 by using a type A durometer.

(7) Shrinkage from mold dimensions

Shrinkage from mold dimensions in the flow direction and in the direction at the right angle to the flow was measured in accordance with ASTM D955.

(8) Coefficient of linear expansion

Coefficient of linear expansion was measured at a temperature ranging from 40° to 150° C. under a load of 0.16 kgf/cm$^2$ by using TMA available from Rigaku Denki Co., Ltd.

REFERENCE EXAMPLE 5

Synthesis of a VdF/TFE/HFP copolymer without functional group

A vinylidene fluoride/tetrafluoroethylene/hexafluoropropylene copolymer was obtained in the same manner as in EXAMPLE 36 except that perfluoro(1,1,9,9tetrahydro-2,5-bistrifluoromethyl-3,6-dioxa-8-nonenol) was not used. At the time when 150 g of the monomer mixture of vinylidene fluoride/tetrafluoroethylene/hexafluoropropylene (molar ratio 60/20/20) was consumed (5.5 hours) in the polymerization reaction of EXAMPLE 36, feeding thereof was stopped and the un-reacted monomer was discharged. The reaction product was then treated in the same manner as in EXAMPLE 36 to give 145 g of a rubber-like polymer.

The composition of the obtained polymer was vinylidene fluoride/tetrafluoroethylene/hexafluoropropylene=61.3/18.9/19.8% by mole by using $^{19}$F-NMR and $^{1}$H-NMR. The molecular weight by GPC analysis (THF solvent) was 215,000 in number average molecular weight and 473,000 in weight average molecular weight. The glass transition point measured by DSC was −17° C., and the thermal decomposition temperature when the weight decreased by 1% was 420° C.

EXAMPLE 44

Improvement of mechanical strength by using a blend of polyphenylene sulfide resin and a fluorine-containing elastomer with functional group A 60 cm$^3$ Brabender mixer being set at 300° C. was charged with 44.8 g of poly(phenylene sulfide) resin (TOHPREN T4 available from Tohpren Co., Ltd.). After melting at 50 rpm for four minutes, 15.1 g of the fluorine-containing elastomer with hydroxyl group obtained in EXAMPLE 38 was added and kneading was carried out at 100 rpm for six minutes. In this case, as compared with COMPARATIVE EXAMPLE 1 as mentioned hereinafter, there was larger increase in torque at the time of mixing. The obtained composition was compression-molded at 300° C. to give test pieces. The bending test and Izod impact test were conducted by using the obtained test pieces. The results are shown in TABLE 10.

COMPARATIVE EXAMPLE 1

Kneading and molding were carried out in the same manner as in EXAMPLE 44 except that the fluorine-containing elastomer without functional group prepared in REFERENCE EXAMPLE 5 was used instead of the fluorine-containing elastomer with hydroxyl group obtained in EXAMPLE 38, to give test pieces. The results are shown in TABLE 10.

COMPARATIVE EXAMPLE 2

Poly(phenyl sulfide) resin (same as in EXAMPLE 44) was compression-molded at 300° C. to give test pieces. The tests were carried out in the same manner as in EXAMPLE 44. The results are shown in TABLE 10.

TABLE 10

| Test results | Ex. 44 | Com. Ex. 1 | Comp. Ex. 2 |
|---|---|---|---|
| Composition (% by weight) | | | |
| Fluorine-containing polymer (D) with functional group EXAMPLE 38 | 20 | — | — |
| Thermoplastic resin (E) Poly(arylene sulfide) | 80 | 80 | 100 |
| Other polymer (F) REFERENCE EXAMPLE 5 | — | 20 | — |
| Properties of molded article | | | |
| Bending strength (kgf/cm$^2$) | 780 | 570 | 1150 |
| Bending modulus (kgf/cm$^2$) | 38700 | 35000 | 37000 |
| Izod impact strength (kgf · cm/cm) | 3.4 | 1.4 | 1.3 |

As it is clear from the results in TABLE 10, as compared with the blend (COMPARATIVE EXAMPLE 1) of the fluorine-containing elastomer without functional group, it is possible to improve Izod impact strength more effectively without remarkably lowering mechanical properties, by blending the hydroxyl-introduced fluorine-containing elastomer with the poly(phenylene sulfide) resin (EXAMPLE 44).

EXAMPLE 45

Blend of a polyamide resin and a fluorine-containing elastomer with functional group A 60 cm$^3$ Brabender mixer being set at 190° C. was charged with 22.5 g of polyamide 12 (UBE NYLON 12 3024B available from Ube Industries, Ltd.), and after melting at 10 rpm for 2 minutes, 33.8 g of the fluorine-containing elastomer with carboxyl group obtained in EXAMPLE 41 was added at 50 rpm, followed by kneading at 100 rpm for 5 minutes. The obtained composition was compression-molded at 200° C. to give test pieces. The results are shown in TABLE 11.

EXAMPLE 46

Enhancement of chemical resistance by blending a polyamide resin and a fluorine-containing elastomer with functional group Kneading and molding were carried out in the same manner as in EXAMPLE 45 except that 33.2 g of polyamide 12 (same as in EXAMPLE 45) and 14.2 g of the fluorine-containing elastomer with carboxyl group prepared in EXAMPLE 41 were used, to give test pieces.

The tensile test and chemical resistance test were carried out by using the obtained test pieces.
(Chemical resistance test)

The test piece was dipped in a toluene/isooctane/methanol=40/40/20 (% by volume) mixed solvent at 50° C. for 72 hours and then the volume change and strength retention were measured in accordance with JIS-K630.

The results are shown in TABLE 11.

EXAMPLE 47
Addition of a fluorine-containing polymer with functional group to a blend of a polyamide resin and PVDF A 60 cm$^3$ blender mixer being set at 210° C. was charged with 32.7 g of polyamide 12 (same as in EXAMPLE 45), and after melting at 10 rpm for 2 minutes, 11.7 g of PVDF (NEOFLON VDF VP-800 available from Daikin Industries, Ltd.) was added. Then after mixing for 2 minutes, 2.3 g of a fluorine-containing polymer with carboxyl group of EXAMPLE 18 was added at 50 rpm, followed by kneading at 100 rpm for 5 minutes. The obtained composition was compression-molded at 210° C. to give test pieces. The results are shown in TABLE 11.

EXAMPLE 48
Addition of a fluorine-containing polymer with functional group to a blend of a polyamide resin and PVdF Kneading and molding were carried out in the same manner as in EXAMPLE 47 except that 9.3 g of PVDF (same as in EXAMPLE 47) and 4.7 g of a fluorine-containing polymer with carboxyl group of EXAMPLE 18 were used, to give test pieces. The results are shown in TABLE 11.

EXAMPLE 49
Addition of a fluorine-containing polymer with functional group to a blend of a polyamide resin and PVDF Kneading and molding were carried out in the same manner as in EXAMPLE 47 except that the fluorine-containing polymer having glycidyl group obtained in EXAMPLE 26 was used instead of the fluorine-containing polymer with carboxyl group obtained in EXAMPLE 18, to give test pieces.

EXAMPLE 50
Addition of a fluorine-containing polymer with functional group to a blend of a polyamide resin and ETFE A 60 cm$^3$ blender mixer being set at 240° C. was charged with 33.0 g of polyamide 12 (same as in EXAMPLE 45), and after melting at 10 rpm for 2 minutes, 11.8 g of ETFE (NEOFLON ETFE EP-610 available from Daikin Industries, Ltd.) was added. Then after mixing for two minutes, 2.4 g of the fluorine-containing polymer with carboxyl group prepared in EXAMPLE 22 was added at 50 rpm, followed by kneading at 100 rpm for 5 minutes.

The obtained composition was compression-molded at 240° C. to give test pieces. The results are shown in TABLE 11.

EXAMPLE 51
Addition of a fluorine-containing polymer with functional group to a blend of a polyamide resin and ETFE Kneading and molding were carried out in the same manner as in EXAMPLE 50 except that 9.4 g of ETFE (same as in EXAMPLE 50) and 4.8 g of the fluorine-containing polymer with carboxyl group obtained in EXAMPLE 22 were used, to give test pieces. The results are shown in TABLE 11.

TABLE 11

| Test results | Ex. 45 | Ex. 46 | Ex. 47 | Ex. 48 | Ex. 49 | Ex. 50 | Ex. 51 |
|---|---|---|---|---|---|---|---|
| Composition (% by weight) | | | | | | | |
| Fluorine-containing polymer (D) with functional group | | | | | | | |
| Polymer of EXAMPLE 18 | — | — | 5 | 10 | — | — | — |
| Polymer of EXAMPLE 22 | — | — | — | — | — | 5 | 10 |
| Polymer of EXAMPLE 26 | — | — | — | — | 5 | — | — |
| Polymer of EXAMPLE 41 | 60 | 30 | — | — | — | — | — |
| Thermoplastic resin (E) | | | | | | | |
| Polyamide 12 | 40 | 70 | 70 | 70 | 70 | 70 | 70 |
| Fluorine-containing polymer (F) without functional group | | | | | | | |
| PVdF[1] | — | — | 25 | 20 | 25 | — | — |
| ETFE[2] | — | — | — | — | — | 25 | 20 |
| Properties of molded article | | | | | | | |
| (Tensile test) | | | | | | | |
| Tensile strength (kgf/cm$^2$) | 166 | 376 | 460 | 430 | 458 | 390 | 360 |
| Tensile modulus (kgf/cm$^2$) | 3900 | 7600 | 10700 | 12900 | 9900 | 10400 | 11900 |
| (Chemical resistance test) | | | | | | | |
| Volume change (%) | — | 15.7 | 10.4 | 11.3 | 12.8 | 10.9 | 10.4 |
| Strength retention[3] (%) | — | 102 | 102 | 97 | 88 | 85 | 80 |

[1]NEOFLON VDF VP-800 available from Daikin Industries, Ltd.
[2]NEOFLON ETFE EP-610 available from Daikin Industries, Ltd.
[3][(Tensile strength after chemical resistance test)/(tensile strength before test)] × 100

COMPARATIVE EXAMPLE 3

Kneading and molding were carried out in the same manner as in EXAMPLE 45 except that a vinylidene fluoride/tetrafluoroethylene/hexafluoropropylene copolymer without functional group (DAI-EL G-902 available from Daikin Industries, Ltd.) was used instead of the fluorine-containing polymer with carboxyl group obtained in EXAMPLE 41, to give test pieces. The results are shown in TABLE 12.

COMPARATIVE EXAMPLE 4

Kneading and molding were carried out in the same manner as in EXAMPLE 46 except that the fluorine-containing elastomer without functional group (same as in COMPARATIVE EXAMPLE 3) was used instead of the fluorine-containing elastomer with carboxyl group, which was prepared in EXAMPLE 41, to give test pieces. The results are shown in TABLE 12.

COMPARATIVE EXAMPLE 5

A blender mixer being set at 210° C. was charged with 32.7 g of polyamide 12 (same as in EXAMPLE 45), and after melting at 10 rpm for 2 minutes, 14.0 g of PVdF (same as in EXAMPLE 47) was added, followed by kneading at 100 rpm for 5 minutes. Test pieces were prepared in the same manner as in EXAMPLE 47. The results are shown in TABLE 12.

COMPARATIVE EXAMPLE 6

A blender mixer being set at 240° C. was charged with 33.0 g of polyamide 12 (same as in EXAMPLE 45), and after melting at 10 rpm for 2 minutes, 14.2 g of ETFE (same as in EXAMPLE 50) was added, followed by kneading at 100 rpm for 5 minutes. Test pieces were prepared in the same manner as in EXAMPLE 50. The results are shown in TABLE 12.

COMPARATIVE EXAMPLE 7

Test pieces were prepared by kneading and molding in the same manner as in EXAMPLE 47 except that epoxy-modified polystyrene-acrylic graft polymer type compatibilizing agent (REZEDA GP300 available from Toagosei Chemical Industry Co., Ltd.) was used instead of the fluorine-containing polymer with carboxyl group, which was prepared in EXAMPLE 18. The results are shown in TABLE 12

COMPARATIVE EXAMPLE 8

Polyamide 12 (same as in EXAMPLE 45) was compression-molded at 190C to give test pieces. The results are shown in TABLE 12.

TABLE 12

| Test results | Com. Ex. 3 | Com. Ex. 4 | Com. Ex. 5 | Com. Ex. 6 | Com. Ex. 7 | Com. Ex. 8 |
|---|---|---|---|---|---|---|
| Composition (% by weight) | | | | | | |
| Thermoplastic resin (D) | | | | | | |
| Polyamide 12 | 40 | 70 | 70 | 70 | 70 | 100 |
| Fluorine-containing polymer (F) without functional group | | | | | | |
| VdF/TFE/HFP copolymer (fluorine-containing elastomer)[1] | 60 | 30 | — | — | — | — |
| PVdF[2] | — | — | 30 | — | 25 | — |
| ETFE[3] | — | — | — | 30 | — | — |
| Other acryl type | | | | | | |
| compatibilizing agent[4] | — | — | — | — | 5 | — |
| Properties of molded article | | | | | | |
| (Tensile test) | | | | | | |
| Tensile strength (kgf/cm$^2$) | 32 | 287 | 453 | 350 | 471 | 416 |
| Tensile modulus (kgf/cm$^2$) | 640 | 6600 | 9600 | 9400 | 9300 | 8000 |
| (Chemical resistance test) | | | | | | |
| Volume change (%) | — | 15.8 | 11.5 | 14 | 28 | 15.8 |
| Strength retention[5] (%) | — | 70 | 57.2 | 48.3 | 53 | 74 |

[1]DM-EL G-902 available from Daikin Industries, Ltd.
[2]NEOFLON VDF VP-800 available from Daikin Industries, Ltd.
[3]NEOFLON ETFE EP-610 available from Daikin Industries, Ltd.
[4]RESEDA GP300 available from Toagosei Chemical Industry Co., Ltd.
[5][(Tensile strength after chemical resistance test)/(tensile strength before test)] × 100

As it is clear from a comparison between the tensile test results of EXAMPLE 45 (TABLE 11) and COMPARATIVE EXAMPLE 3 (TABLE 12), the tensile strength and tensile modulus can be considerably enhanced by introducing a carboxyl group to the fluorine-containing polymer in blending with polyamide.

As it is clear from the respective test results of EXAMPLES 46 to 51 in TABLE 11, excellent mechanical properties and chemical resistance are obtained by blending the fluorine-containing polymer with carboxyl group or the fluorine-containing polymer with glycidyl group with the polyamide resin.

Particularly in case of the blend of the fluorine-containing polymer without functional group with polyamide (COMPARATIVE EXAMPLES 4 to 6 in TABLE 12), tensile strength lowers remarkably after the chemical resistance test, and also in case of a blend (COMPARATIVE EXAMPLE 7) in which the epoxy-modified polystyrene-acrylic graft polymer type compatibilizing agent was added, though enhancement of tensile strength could be initially observed, the strength lowered remarkably after the chemical resistance test.

On the contrary, in case of the blend of the fluorine-containing polymer with carboxyl group or glycidyl group with polyamide, not only an excellent mechanical properties but also excellent tensile strength after the chemical resistance test were exhibited. That is, it was found that there can be obtained a composition having the enhanced dispersibility and surface adhesivity of the fluorine-containing polymer in the blend with polyamide by introducing a functional group to the fluorine-containing polymer.

EXAMPLE 52

Blend of a liquid crystal polyester and the fluorine-containing elastomer with hydroxyl group A 60 cm$^3$ Brabender mixer being set at 200° C. was charged with 26.0 g of a liquid crystal polyester (NOVACCURATE E310 available from Mitsubishi Chemical Corp.), and after melting at 10 rpm for 1.5 minutes, 38.9 g of the fluorine-containing elastomer with hydroxyl group prepared in EXAMPLE 36 was added at 50 rpm, followed by kneading at 100 rpm for 5 minutes. The obtained composition was compression-molded at 200° C. to give test pieces. The tensile test was carried out by using the test pieces. The results are shown in TABLE 13.

EXAMPLE 53

Blend of a liquid crystal polyester and the fluorine-containing elastomer with hydroxyl group Kneading and molding were carried out in the same manner as in EXAMPLE 52 except that the fluorine-containing elastomer with hydroxyl group prepared in EXAMPLE 37 was used, to give test pieces. The results are shown in TABLE 13.

EXAMPLES 54 AND 55

Blend of a liquid crystal polyester and the fluorine-containing elastomer with hydroxyl group Kneading and molding were carried out in the same manner as in EXAMPLE 52 except that 41.1 g of a liquid crystal polyester (same as in EXAMPLE 52) and 17.6 g of the fluorine-containing elastomer with hydroxyl group obtained in EXAMPLE 36 (EXAMPLE 54) or EXAMPLE 37 (EXAMPLE 55), respectively, were used, to give test pieces. The results are shown in TABLE 13.

EXAMPLE 56

Blend of a liquid crystal polyester and the fluorine-containing elastomer with hydroxyl group Kneading and molding were carried out in the same manner as in EXAMPLE 54 except that kneading and compression-molding were conducted at 300° C. by using 42.5 g of the liquid crystal polyester (VECTRA A950 available from Polyplastics Co., Ltd.) and 18.2 g of the fluorine-containing elastomer with hydroxyl group prepared in EXAMPLE 36, to give test pieces. The results are shown in TABLE 13.

COMPARATIVE EXAMPLES 9 TO 11

With the use of a fluorine-containing elastomer without functional group (same as in COMPARATIVE EXAMPLE 3) instead of the fluorine-containing elastomer with hydroxyl group, kneading and molding were carried out in the same manner as in EXAMPLE 52 for COMPARATIVE EXAMPLE 9, in EXAMPLE 54 for COMPARATIVE EXAMPLE 10 and in EXAMPLE 56 for COMPARATIVE EXAMPLE 11, respectively, to give test pieces. The results are shown in TABLE 13.

Also the molded articles obtained in EXAMPLES 55 and 56 and COMPARATIVE EXAMPLES 10 and 11 were frozen in liquid nitrogen and broken, and the broken surfaces were observed with a scanning type electron microscope. The photographs (×500) of those cut surfaces are shown in FIGS. 2, 3, 4 and 5, respectively.

TABLE 13

| Test results | Ex. 52 | Ex. 53 | Ex. 54 | Ex. 55 | Ex. 56 | Com. Ex. 9 | Com. Ex. 10 | Com. Ex. 11 |
|---|---|---|---|---|---|---|---|---|
| Composition (% by weight) | | | | | | | | |
| Fluorine-containing polymer (D) with functional group | | | | | | | | |
| Polymer of EXAMPLE 36 | 60 | — | 30 | — | 30 | — | — | — |
| Polymer of EXAMPLE 37 | — | 60 | — | 30 | — | — | — | — |
| Thermoplastic resin (E) | | | | | | | | |
| Liquid crystal polyester (I)[1] | 40 | 40 | 70 | 70 | — | 40 | 70 | — |
| Liquid crystal polyester (II)[2] | — | — | — | — | 70 | — | — | 70 |
| Fluorine-containing polymer (F) without functional group | | | | | | | | |
| VdF/TFE/HFP copolymer[3] (elastomer) | — | — | — | — | — | 60 | 30 | 30 |
| Properties of composition (Tensile test) | | | | | | | | |
| Tensile strength (kgf/cm$^2$) | 115 | 151 | 360 | 333 | 692 | 22.9 | 215 | 560 |

TABLE 13-continued

| Test results | Ex. 52 | Ex. 53 | Ex. 54 | Ex. 55 | Ex. 56 | Com. Ex. 9 | Com. Ex. 10 | Com. Ex. 11 |
|---|---|---|---|---|---|---|---|---|
| Tensile modulus (kgf/cm$^2$) | 4100 | 3400 | 15000 | 12700 | 23100 | 480 | 9800 | 17900 |
| Electron microscope photograph of cut surface | — | — | — | FIG. 2 | FIG. 3 | — | FIG. 4 | FIG. 5 |

[1])NOVACCURATE E310 available from Mitsubishi Chemical Corp.
[2])VECTRA A950 available from Polyplastics Co., Ltd.
[3])DM-EL G-902 available from Daikin Industries. Ltd.

As it is clear from the results of TABLE 13, mechanical properties (tensile strength tensile modulus) can be considerably enhanced by blending the hydroxyl-introduced fluorine-containing elastomer with the liquid crystal polyester (EXAMPLES 52 to 56) as compared with the case where the conventional fluorine-containing elastomer is blended (COMPARATIVE EXAMPLES 9 to 11).

Figure 2:
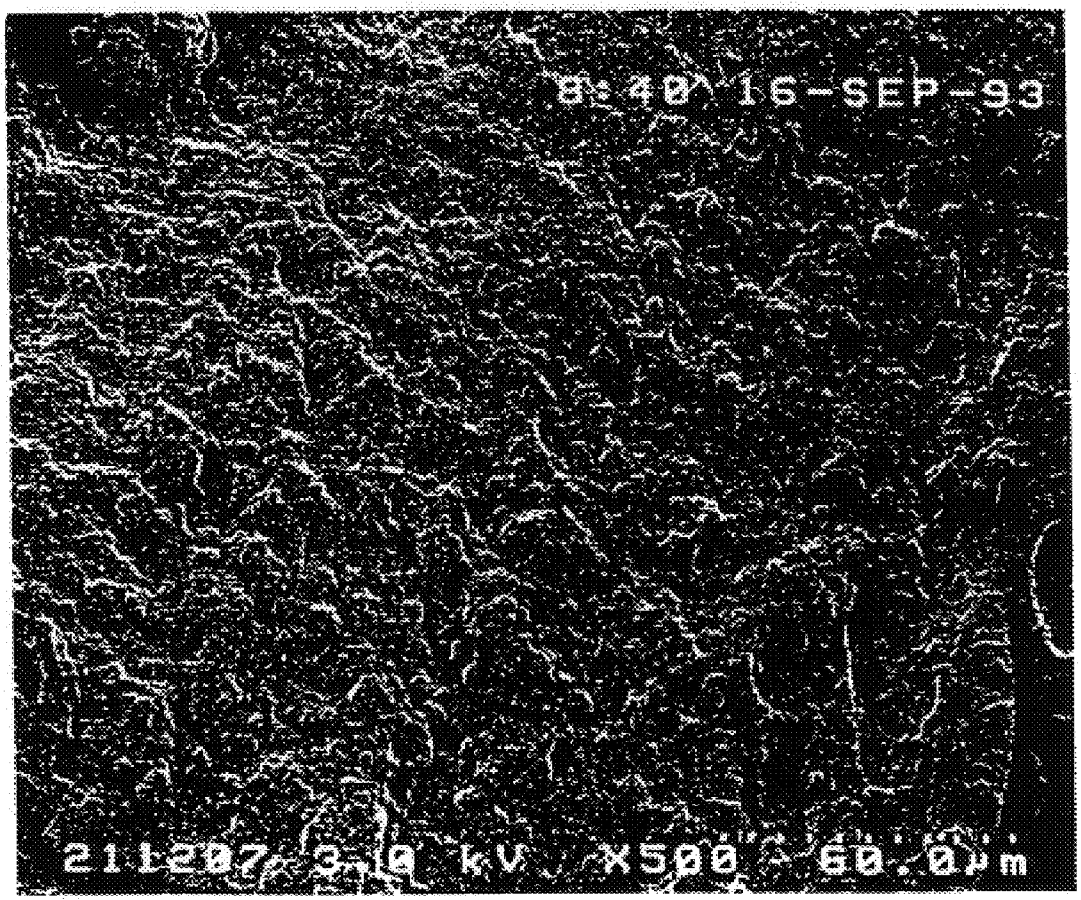
FIG. 2 is a scanning type electron microscope photograph of a cut surface of the molded article obtained in EXAMPLE 55.
Figure 3:
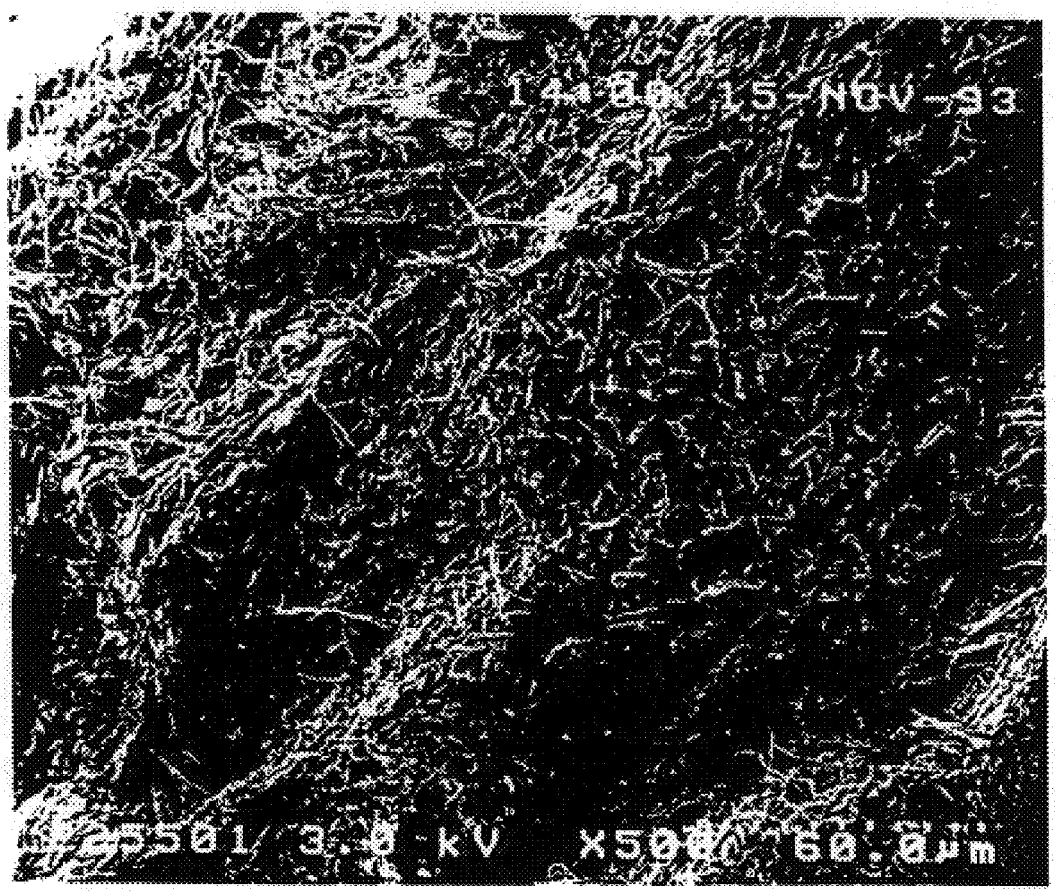
FIG. 3 is a scanning type electron microscope photograph of a cut surface of the molded article obtained in EXAMPLE 56.
Figure 4:
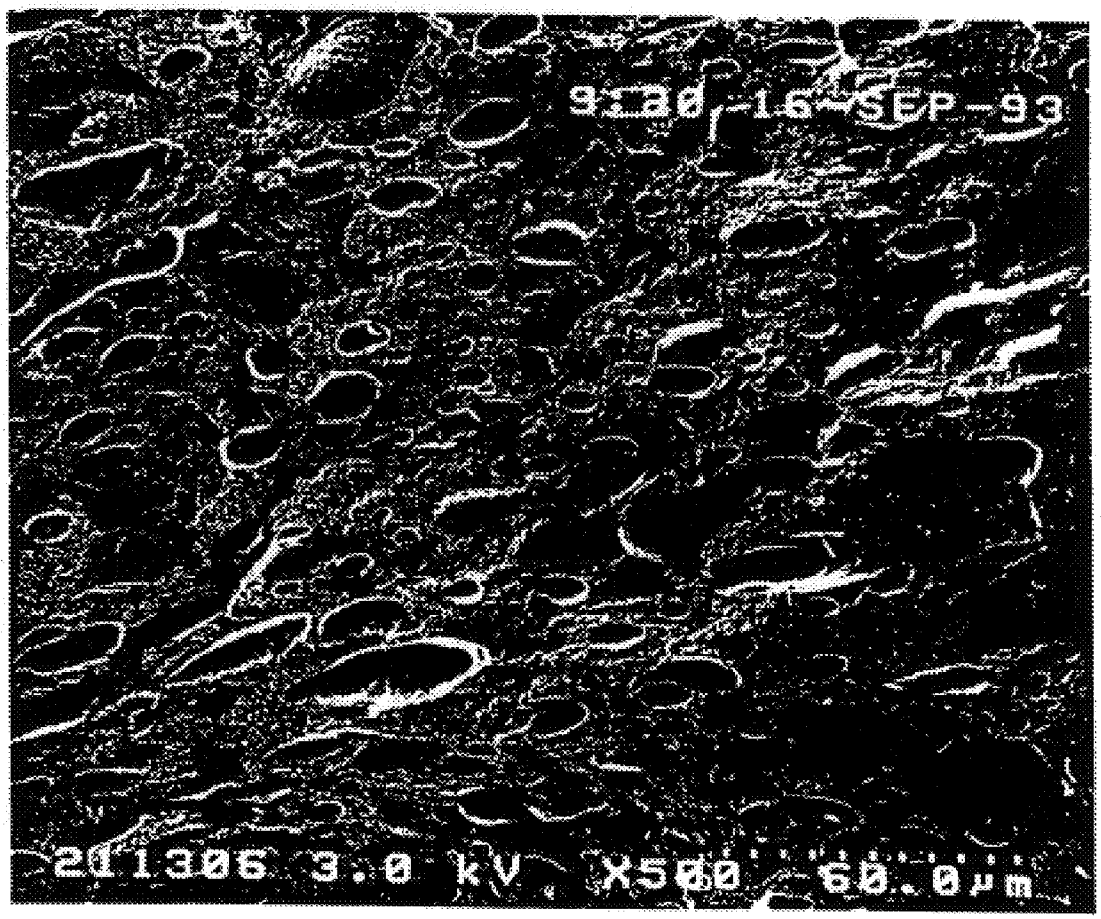
FIG. 4 is a scanning type electron microscope photograph of a cut surface of the molded article obtained in COMPARATIVE EXAMPLE 10.
Figure 5:
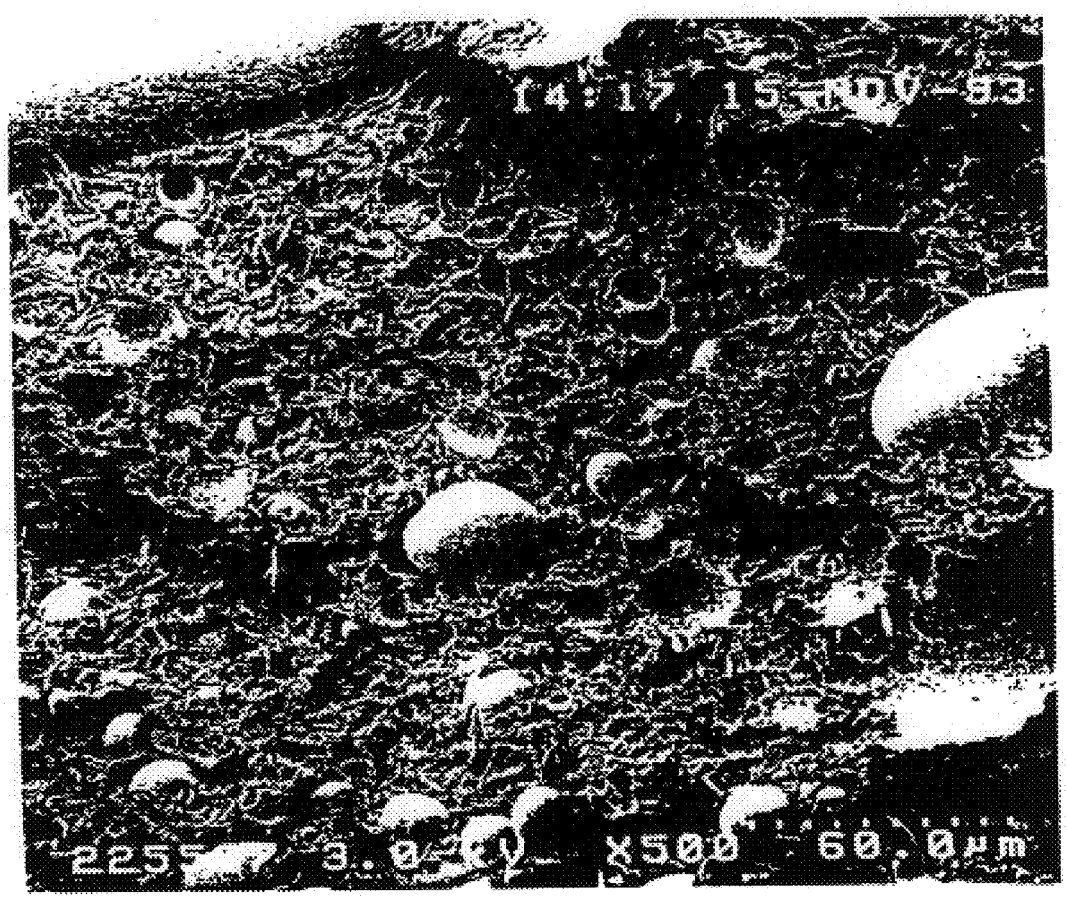
FIG. 5 is a scanning type electron microscope photograph of a cut surface of the molded article obtained in COMPARATIVE EXAMPLE 11.

Also as it is clear from comparing the photographs of the cut surfaces between FIG. 2 with FIG. 4 and FIG. 3 with FIG. 5, it can be recognized that in the molded articles prepared by using the hydroxyl-containing elastomer (FIG. 2 and FIG. 3), the liquid crystal polyester formed matrix and the fluorine-containing elastomer was finely dispersed therein.

It is assumed that by introducing hydroxyl group into the fluorine-containing polymer, the hydroxyl group reacts partly with the liquid crystal polyester to enhance dispersibility with each other, and as a result, increase mechanical properties more effectively.

EXAMPLE 57
Addition of the fluorine-containing polymer with functional group to the blend of a liquid crystal polyester and PVDF A 60 cm$^3$ Brabender mixer being set at 20 ° C. was charged with 21.7 g of a liquid crystal polyester (same as in EXAMPLE 52), and after melting at 10 rpm for 1.5 minutes, 38.3 g of PVDF (same as in EXAMPLE 47) was added, followed by mixing for 2 minutes. Then 3.8 g of the fluorine-containing polymer with hydroxyl group prepared in EXAMPLE 17 was added at 50 rpm, followed by kneading at 100 rpm for 5 minutes. The obtained composition was crushed and then molded by an injection molding machine at a cylinder temperature of 200° to 250° C. and a die temperature of 80° C. to give test pieces. The measurement of tensile test, bending test and melt flow rate were conducted by using the obtained test pieces. The results are shown in TABLE 14.

EXAMPLE 58
Addition of a fluorine-containing polymer with functional group to a blend of a liquid crystal polyester and PVdF Kneading and molding were carried out in the same manner as in EXAMPLE 57 except that 24.5 g of a liquid crystal polyester (same as in EXAMPLE 52), 43.2 g of PVdF (same as in EXAMPLE 47) and 4.4 g of the fluorine-containing polymer having hydroxyl group, which was obtained in EXAMPLE 37, were used, to give test pieces. The results are shown in TABLE 14.

COMPARATIVE EXAMPLE 12

Kneading and molding were carried out in the same manner as in EXAMPLE 57 except that a VdF/TFE/HFP copolymer (same as in COMPARATIVE EXAMPLE 3) without functional group was used instead of the fluorine-containing polymer with hydroxyl group prepared in EXAMPLE 17, to give test pieces. The results are shown in EXAMPLE 14.

COMPARATIVE EXAMPLE 13

A blender mixer being set at 200° C. was charged with 24.4 g of a liquid crystal polyester (same as in EXAMPLE 52), and after melting at 10 rpm for 1.5 minutes, 47.4 g of PVDF (same as in EXAMPLE 47) was added at 50 rpm, followed by kneading at 100 rpm. The obtained composition was molded in the same manner as in EXAMPLE 57 to give test pieces. The results are shown in TABLE 14.

TABLE 14

| Test Results | Ex. 57 | Ex. 58 | Com. Ex. 12 | Com. Ex. 13 |
|---|---|---|---|---|
| Composition (% by weight) | | | | |
| Fluorine-containing polymer (D) with functional group | | | | |
| Polymer of EXAMPLE 17 | 5 | — | — | — |
| Polymer of EXAMPLE 37 | — | 5 | — | — |
| Thermoplastic resin (E) | 35 | 35 | 35 | 35 |
| Liquid crystal polyester (I)[1)] | | | | |
| Fluorine-containing polymer (F) without functional group | | | | |
| PVdF[2)] | 60 | 60 | 60 | 65 |
| VdF/TFE/HFP copolymer[3)] (elastomer) | — | — | 5 | — |
| Properties of composition | | | | |
| (Tensile test) | | | | |
| Tensile strength (kgf/cm$^2$) | 735 | 675 | 642 | 720 |
| Tensile modulus (kgf/cm$^2$) | 30400 | 30200 | 29000 | 28400 |
| (Bending test) | | | | |
| Bending strength (kgf/cm$^2$) | 770 | 741 | 476 | 573 |
| Bending Modulus (kgf/cm$^2$) | 27500 | 27500 | 24300 | 27300 |
| Melt flow rate[4)] (g/10 min) | 46.2 | 52.5 | 65.6 | 65.8 |

[1])NOVACCURATE E310 available from Mitsubishi Chemical Corp.
[2])NEOFLON VDF VP-800 available from Daikin Industries, Ltd.
[3])DAI-EL G-902 available from Daikin Industries, Ltd.
[4])At 250° C. under 5 kgf/cm$^2$ load As is clear from TABLE 14, tensile modulus, bending characteristics and moldability were enhanced by adding the fluorine-containing polymer with hydroxyl group at the time when blending the liquid crystal polyester and PVDF.

Even in case of a simple blending of the liquid crystal polyester and PVdF, it is possible to improve particularly tensile strength of PVdF since the liquid crystal polyester is oriented in the injection molding direction. However since dispersibility and surface adhesivity are insufficient, characteristics in the direction of the right angle to the orientation, that is, bending characteristics becomes insufficient. Contrarily in case where the fluorine-containing polymer with functional group is added when blending the liquid crystal polyester and PVdF, dispersibility and surface adhesivity can be improved and tensile modulus and bending characteristics can be enhanced more.

EXAMPLES 59 AND 60

Addition of the fluorine-containing polymer with functional group when blending PVdF and the liquid crystal polyester (II)

PVdF (same as in EXAMPLE 47), the liquid crystal polyester (same as in EXAMPLE 56) and the fluorine-containing polymer with hydroxyl group prepared in EXAMPLE 38 were blended homogeneously in the amounts shown in TABLE 15, and then kneaded and extruded at 280° to 300° C. by a biaxial extrusion machine to give pellets.

Test pieces were prepared by using these pellets by an injection molding machine at a cylinder temperature of 240° to 290° C. and a die temperature of 50° C., and then tensile test, bending test and measurement of a deflection temperature under load were carried out. The results are shown in TABLE 15.

COMPARATIVE EXAMPLE 14

PVDF (same as in EXAMPLE 47), the liquid crystal polyester (same as in EXAMPLE 56) and the VdF/TFE/HFP copolymer (same as in COMPARATIVE EXAMPLE 3) were homogeneously blended in the amounts shown in TABLE 15, kneaded by an extrusion machine and injection-molded in the same manner as in EXAMPLE 59 to give test pieces. The results are shown in TABLE 15.

COMPARATIVE EXAMPLE 15

PVdF (same as in EXAMPLE 47) and the liquid crystal polyester (EXAMPLE 56) were kneaded and molded in the same manner as in EXAMPLE 59 to give test pieces. The results are shown in TABLE 15.

COMPARATIVE EXAMPLE 16

PVdF pellets (same as in EXAMPLE 47) were injection-molded in the same manner as in EXAMPLE 59 to give test pieces. The results are shown in TABLE 15.

TABLE 15

| Test Results | Ex. 59 | Ex. 60 | Com. Ex. 14 | Com. Ex. 15 | Com. Ex. 16 |
| --- | --- | --- | --- | --- | --- |
| Composition (% by weight) | | | | | |
| Fluorine-containing polymer (D) with functional group Polymer of EXAMPLE 38 | 3 | 6 | — | — | — |
| Thermoplastic resin (E) Liquid crystal polyester (II)[1] | 20 | 20 | 20 | 20 | — |
| Fluorine-containing polymer (F) without functional group | | | | | |
| PVdF[2] | 77 | 74 | 77 | 80 | 100 |
| VdF/TFE/HFP copolymer[3] (elastomer) | — | — | 3 | — | — |
| Properties of composition | | | | | |
| (Tensile test) | | | | | |
| Tensile strength (kgf/cm$^2$) | 745 | 766 | 710 | 790 | 720 |
| Tensile modulus (kgf/cm$^2$) | 27200 | 27900 | 25900 | 26400 | 11400 |
| (Bending test) | | | | | |
| Bending strength (kgf/cm$^2$) | 770 | 740 | 760 | 780 | 680 |
| Bending modulus (kgf/cm$^2$) | 39300 | 38300 | 37700 | 38500 | 13700 |
| Deflection temperature under load (° C.) | 150.0 | 150.4 | 140.7 | 130.8 | 108.0 |
| Melt flow rate[4] (g/10 min) | 117 | 125 | 108 | 104 | 45.2 (35.1)[5] |

[1]VECTRA A950 available from POLYPLASTICS CO., LTD.
[2]NEOFLON VDF VP-800 available from Daikin Industries, Ltd.
[3]DAI-EL G-902 available from Daikin Industries, Ltd.
[4]At 300° C. under 5 kgf/cm$^2$ load
[5]Value in the parenthesis is one measured at 250° C. under 5 kgf/cm$^2$ load The results of TABLE 15 indicate that injection-molded articles which are prepared by adding the fluorine-containing polymer with hydroxyl group when PVdF and the liquid crystal polyester are kneaded and extruded, can be endowed with a deflection temperature under load and moldability of PVdF which are improved more effectively as compared with the simple blend of PVdF and the liquid crystal polyester.

EXAMPLE 61 AND COMPARATIVE EXAMPLES 17 and 18

Addition of the fluorine-containing polymer with functional group at the time when blending ETFE and the liquid crystal polyester (III)

ETFE (NEOFLON ETFE EP-521 available from Daikin Industries, Ltd.), the liquid crystal polyester (SUMIKA SUPER LCP E7000 available from Sumitomo Chemical Co., Ltd.) and the fluorine-containing polymer with hydroxyl group prepared in EXAMPLE 32 were homogeneously blended in the amounts shown in TABLE 16 by a rocking mixer, and then kneaded and extruded at 280° to 300° C. by a biaxial extrusion machine to give pellets. Test pieces were then prepared by using the pellets with an injection molding machine at a cylinder temperature of 280° to 320° C. and a die temperature of 100° C. The tensile test, bending test and measurements of shrinkage from mold dimensions, a coefficient of linear expansion and a deflection temperature under load were conducted. The results are shown in TABLE 16.

TABLE 16

| Test Results | Ex. 61 | Com. Ex. 17 | Com. Ex. 18 |
|---|---|---|---|
| Composition (% by weight) | | | |
| Fluorine-containing polymer (D) with functional group Polymer of EXAMPLE 32 | 5 | — | — |
| Thermoplastic resin (E) Liquid crystal polyester (III)[1] | 20 | 20 | — |
| Fluorine containing polymer (F) without functional group ETFE[2] | 75 | 80 | 100 |
| Properties of composition | | | |
| (Shrinkage from mold dimensions) | | | |
| Flow direction (%) | 0.07 | 0.15 | 1.95 |
| Direction vertical to flow (%) | 3.60 | 3.74 | 3.91 |
| (Tensile test) | | | |
| Tensile strength (kgf/cm$^2$) | 360 | 320 | 360 |
| Tensile modulus (kgf/cm$^2$) | 20500 | 18000 | 6300 |
| (Bending test) | | | |
| Bending strength (kgf/cm$^2$) | 485 | 472 | — |
| Bending modulus (kgf/cm$^2$) | 31400 | 29600 | — |
| Coefficient of linear expansion[3] ($\times 10^5$/° C. | 3.2 | 3.70 | 7.14 |
| Deflection temperature under load (° C.) | 118 | 105 | 82.2 |

[1] SUMIKA SUPER LCP E7000 available from Sumitomo Chemical Co., Ltd.
[2] NEOFLON ETFE EP-521 available from Daikin Industries, Ltd.
[3] At 40° to 150° C.

EXAMPLES 62 TO 64 AND COMPARATIVE EXAMPLES 19 and 20

Addition of the fluorine-containing polymer with functional group at the time when blending PFA and the liquid crystal polyester (IV)

PFA (NEOFLON PFA AP-201 available from Daikin Industries, Ltd.), the liquid crystal polyester (SUMIKA SUPER LCP E6000 available from Sumitomo Chemical Co., Ltd.) and the fluorine-containing polymer with hydroxyl group prepared in EXAMPLE 34 or 35 were homogeneously blended in the amounts shown in TABLE 17 by a rocking mixer, and then kneaded and extruded at 350° to 370° C. by a biaxial extrusion machine to give pellets. Test pieces were then prepared by using the pellets with an injection molding machine at a cylinder temperature of 3400 to 360° C. and a die temperature of 190° C., and the same measurements as in EXAMPLE 61 were conducted. The results are shown in TABLE 17.

TABLE 17

| Test Results | Ex. 62 | Ex. 63 | Ex. 64 | Com. Ex. 19 | Com. Ex. 20 |
|---|---|---|---|---|---|
| Composition (% by weight) | | | | | |
| Fluorine-containing polymer (D) with functional group | | | | | |
| Polymer of EXAMPLE 34 | — | — | 10 | — | — |
| Polymer of EXAMPLE 35 | 2 | 5 | — | — | — |
| Thermoplastic resin (E) Liquid crystal polyester (IV)[1] | 30 | 30 | 30 | 30 | — |
| Fluorine-containing polymer (F) without functional group PFA[2] | 68 | 65 | 60 | 70 | 100 |

TABLE 17-continued

| Test Results | Ex. 62 | Ex. 63 | Ex. 64 | Com. Ex. 19 | Com. Ex. 20 |
|---|---|---|---|---|---|
| Properties of composition | | | | | |
| (Shrinkage from mold dimension) | | | | | |
| Flow direction (%) | −0.37 | −0.38 | −0.38 | −0.34 | 4.3 |
| Direction vertical to flow (%) | 4.2 | 4.0 | 3.4 | 4.3 | 4.0 |
| (Tensile test) | | | | | |
| Tensile strength (kgf/cm$^2$) | 535 | 506 | 485 | 470 | 181 |
| Tensile modulus (kgf/cm$^2$) | 29200 | 30600 | 28600 | 25200 | 4100 |
| (Bending test) | | | | | |
| Bending strength (kgf/cm$^2$) | 503 | 480 | 478 | 465 | 193 |
| Bending modulus (kgf/cm$^2$) | 49800 | 47600 | 47600 | 43000 | 5600 |
| Coefficient of linear expansion ($\times 10^5/°$ C.)$^{3)}$ | 2.36 | 2.26 | 2.21 | 2.63 | 8.91 |
| Deflection temperature under load (° C.) | 247 | 249 | 251 | 235 | 64 |

$^{1)}$SUMIKA SUPER LCP E6000 available from Sumitomo Chemical Co., Ltd.
$^{2)}$NEOFLON PFA AP-201 available from Daikin Industries, Ltd.
$^{3)}$At 40° to 150° C.

The results of TABLES 16 and 17 indicate that mechanical properties and dimensional stability of molded articles can be improved, particularly a coefficient of linear expansion and a deflection temperature under load can be improved more effectively by adding the fluorine-containing polymer with hydroxyl group when blending ETFE or PFA and the liquid crystal polyester.

EXAMPLE 65

A thermoplastic elastomer composition prepared by melt-blending the fluorine-containing elastomer with hydroxyl group and the liquid crystal polyester Kneading and molding were carried out in the same manner as in EXAMPLE 52 except the use of 8.2 g of the liquid crystal polyester (same as in EXAMPLE 52) and 73.5 g of the fluorine-containing elastomer with hydroxyl group obtained in EXAMPLE 36, to give test pieces. The tensile test and measurements of melt flow rate and hardness (Shore hardness A) were carried out. The results are shown in TABLE 18.

EXAMPLE 66

A thermoplastic elastomer composition prepared by melt-blending the fluorine-containing elastomer with hydroxyl group and the liquid crystal polyester Kneading and molding were carried out in the same manner as in EXAMPLE 65 except the use of the fluorine-containing elastomer with hydroxyl group obtained in EXAMPLE 38, to give test pieces. The results are shown in TABLE 18.

EXAMPLE 67

A thermoplastic elastomer composition prepared by melt-blending the fluorine-containing elastomer with hydroxyl group and the liquid crystal polyester Kneading and molding were carried out in the same manner as in EXAMPLE 65 except the use of 10.7 g of the liquid crystal polyester (same as in EXAMPLE 52) and 60.6 g of the fluorine-containing elastomer with hydroxyl group obtained in EXAMPLE 38, to give test pieces. The results are shown in TABLE 18.

EXAMPLE 68

A thermoplastic elastomer composition prepared by melt-blending the fluorine-containing elastomer having hydroxyl group and the liquid crystal polyester Kneading and molding were carried out in the same manner as in EXAMPLE 65 except the use of 13.9 g of the liquid crystal polyester (same as in EXAMPLE 52) and 55.9 g of the fluorine-containing elastomer with hydroxyl group obtained in EXAMPLE 38, to give test pieces. The results are shown in TABLE 18.

COMPARATIVE EXAMPLES 21 TO 23

Kneading and molding were carried out in the same manner as in EXAMPLE 65 for COMPARATIVE EXAMPLE 21, in EXAMPLE 67 for COMPARATIVE EXAMPLE 22, and in EXAMPLE 68 for COMPARATIVE EXAMPLE 23, respectively except that the fluorine-containing elastomer without functional group (same as in COMPARATIVE EXAMPLE 3) was used instead of the fluorine-containing elastomer with hydroxyl group, to give test pieces. The results are shown in TABLE 18.

Figure 6:
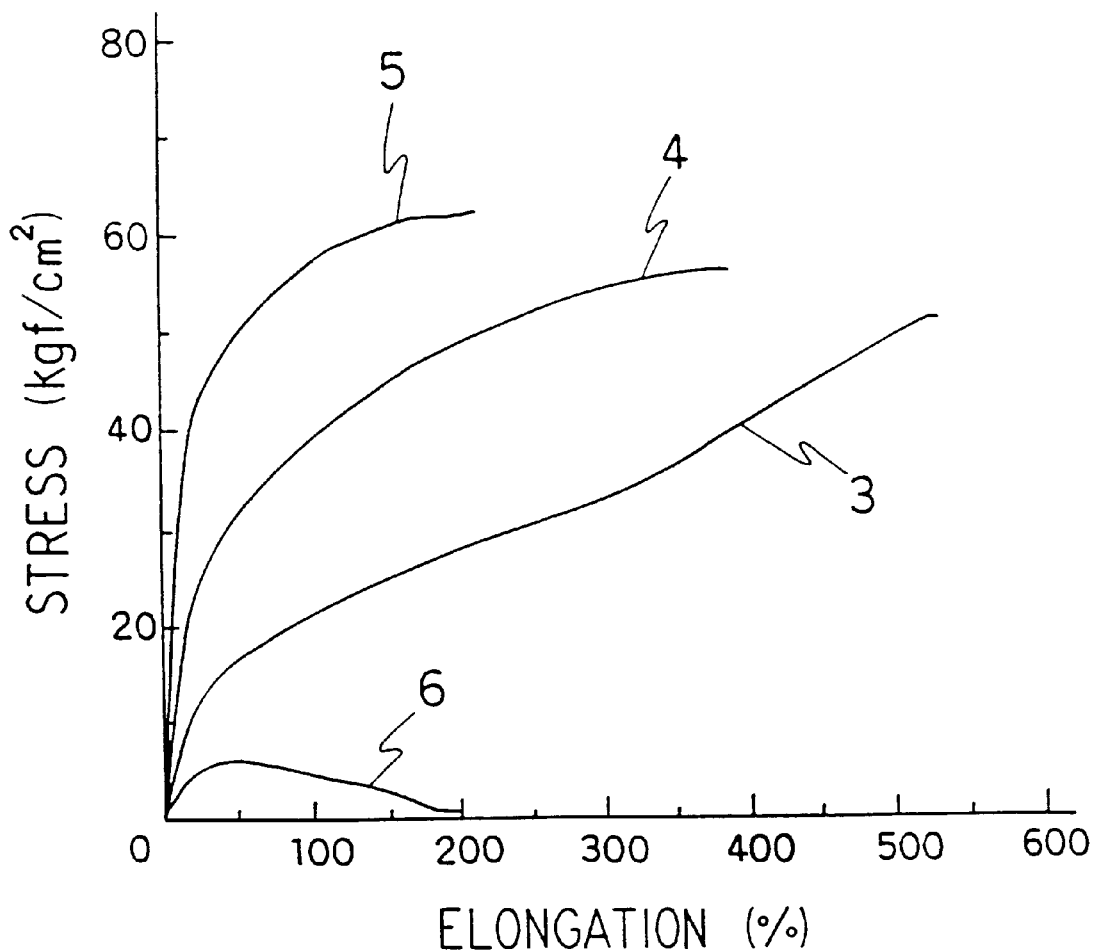
FIG. 6 is a stress-strain curve in the tensile tests of the molded articles obtained in EXAMPLES 66 to 68 and COMPARATIVE EXAMPLE 22.

Also FIG. 6 shows stress-strain curves in the tensile test of the molded articles obtained in EXAMPLES 66 to 68 and COMPARATIVE EXAMPLE 22.

TABLE 18

| Test Results | Ex. 65 | Ex. 66 | Ex. 67 | Ex. 68 | Com. Ex. 21 | Com. Ex. 22 | Com. Ex. 23 |
|---|---|---|---|---|---|---|---|
| Composition (% by weight) | | | | | | | |
| Fluorine-containing polymer (D) with functional group | | | | | | | |
| Polymer of EXAMPLE 36 | 90 | — | — | — | — | — | — |
| Polymer of EXAMPLE 38 | — | 90 | 85 | 80 | — | — | — |
| Thermoplastic resin (E) | | | | | | | |
| Liquid crystal polyester (I)[1] | 10 | 10 | 15 | 20 | 10 | 15 | 20 |
| Fluorine-containing polymer (F) without functional group | | | | | | | |
| VdF/TFE/HFP copolymer[2] (elastomer) | — | — | — | — | 90 | 85 | 80 |
| Properties of composition (Tensile test)[3] | | | | | | | |
| Tensile strength (kgf/cm$^2$) | 41.6 | 51.4 | 56.4 | 62.4 | (6.3)[4] | (5.7) | (7.5) |
| Elongation (%) | 405 | 530 | 390 | 210 | Cannot be fixed[5] | Cannot be fixed | Cannot be fixed |
| Melt flow rate[6] (g/10 min) | 3.56 | 9.90 | 20.2 | 39.1 | — | — | — |
| Hardness (HsA) | 56 | 55 | 72 | 83 | 40 | 44 | 62 |

[1]NOVACCURATE E310 available from Mitsubishi Chemical Corp.
[2]DM-EL G-902 available from Daikin Industries, Ltd.
[3]Cross-head speed 10 mm/min.
[4]Strength at maximum point
[5]No breakage occurred because of low stress against elongation
[6]At 250° C. under 20 kgf/cm$^2$ load As it is clear from TABLE 18 and FIG. 6, the compositions (EXAMPLES 65, 66, 67 and 68) obtained by melt-blending the fluorine-containing elastomer with hydroxyl group and the liquid crystal polyester in the specific composition range exhibits a high stress against elongation and have properties like a crosslinked rubber. Further the compositions prepared by blending the fluorine-containing elastomer with hydroxyl group and the liquid crystal polyester exhibit high temperature flowability and thus have characteristics as a thermoplastic elastomer.

Also the thermoplastic elastomers having various hardnesses can be prepared by selecting a ratio of the fluorine-containing elastomer with hydroxyl group to the liquid crystal polyester from the specific composition range.

On the contrary, the compositions (COMPARATIVE EXAMPLES 21, 22 and 23) prepared by blending with the fluorine-containing elastomer without functional group are merely blended compositions of an unvulcanized rubber and the liquid crystal polyester, and therefore exhibit flowability at high temperature but only low stress against elongation and has no rubber elasticity.

EXAMPLE 69

Addition of the fluorine-containing polymer with functional group when polycarbonate and ETFE are blended.

A Brabender mixer being set at 290° C. was charged with 31.3 g of polycarbonate (PANLITE L-1225WP available from Teijin Chemicals Ltd.), and after melting at 10 rpm for 2 minutes, 7.2 g of ETFE (same as in EXAMPLE 50) was added and mixed for 2 minutes. Then 1.5 g of the fluorine-containing polymer with hydroxyl group of EXAMPLE 19 was added at 50 rpm, followed by kneading at 100 rpm for 5 minutes.

The obtained composition was compression-molded at 29° C. to prepare test pieces, and the tensile test and solvent resistance test were carried out.

The solvent resistance test was conducted in the following manner.

(Solvent resistance test)

The test piece was dipped in toluene and then put in a bath maintaining at a constant temperature and allowed to stand at 25° C. for 48 hours. The volume change of the molded article after the test was measured.

The results are shown in TABLE 19.

COMPARATIVE EXAMPLE 24

A Brabender mixer being set at 290° C. was charged with 37.6 g of polycarbonate (same as in EXAMPLE 69), and after melting at 10 rpm for 2 minutes, 16.1 g of ETFE (same as in EXAMPLE 50) was added at 50 rpm, followed by kneading at 100 rpm. The test pieces were prepared in the same manner as in EXAMPLE 69. The results are shown in TABLE 19.

COMPARATIVE EXAMPLE 25

Molding was carried out in the same manner as in EXAMPLE 69 by using polycarbonate (same as in EXAMPLE 69) to prepare test pieces. The results are shown in TABLE 19.

TABLE 19

| Test Results | Ex. 69 | Com. Ex. 24 | Com. Ex. 25 |
|---|---|---|---|
| Composition (% by weight) | | | |
| Fluorine containing polymer (D) with functional group | 5 | — | — |
| Polymer of EXAMPLE 19 | | | |
| Thermoplastic resin (E) | 70 | 70 | 100 |
| Polycarbonate | | | |

TABLE 19-continued

| Test Results | Ex. 69 | Com. Ex. 24 | Com. Ex. 25 |
|---|---|---|---|
| Fluorine containing polymer without functional group ETFE[1] | 25 | 30 | 0 |
| Properties of composition | | | |
| (Tensile test) | | | |
| Tensile strength (kgf/cm$^2$) | 425 | 419 | 670 |
| Tensile modulus (kgf/cm$^2$) | 13300 | 10700 | 13100 |
| (Solvent resistance test)[2] Volume change (%) | 25 | 47 | 58 |

[1]NEOFLON ETFE, EP-610 available from Daikin Industries, Ltd.
[2]48-hour dipping in toluene at 25° C.

As it is clear from the results of TABLE 19, as compared with the simple blend of polycarbonate and ETFE, solvent resistance of polycarbonate can be effectively improved without lowering mechanical properties by adding the fluorine-containing polymer with hydroxyl group when blending polycarbonate and ETFE.

EXAMPLE 70

A 60 cm$^3$ Brabender mixer being set at 370° C. was charged with 39.0 g of the liquid crystal polyester (same as in EXAMPLE 62), and after melting at 10 rpm for 3 minutes, 39.0 g of the fluorine-containing polymer with hydroxyl group obtained in EXAMPLE 35 was added at 50 rpm, followed by further kneading at 100 rpm for 5 minutes.

The obtained composition was crushed, and test pieces was prepared by an injection molding machine at a cylinder temperature of 320° to 360° C. and a die temperature of 190° C. Then measurements of shrinkage from mold dimensions, tensile test and bending test were carried out. The results are shown in TABLE 20.

COMPARATIVE EXAMPLE 26

Kneading and molding were carried out in the same manner as in EXAMPLE 70 except that PFA (same as in EXAMPLE 62) was used instead of the fluorine-containing polymer with hydroxyl group, to give test pieces. The results are shown in TABLE 20.

TABLE 20

| Test Results | Ex. 70 | Com. Ex. 26 |
|---|---|---|
| Composition (% by weight) | | |
| Fluorine-containing polymer (D) with functional group Polymer of EXAMPLE 35 | 50 | — |
| Thermoplastic resin (E) Liquid crystal polyester (IV)[1] | 50 | 50 |
| Fluorine-containing polymer (F) without functional group PFA[2] | — | 50 |
| Properties of composition | | |
| (Shrinkage from mold dimensions) | | |
| Flow direction (%) | 0.14 | 0.11 |
| Direction vertical to flow (%) | 2.71 | 2.43 |
| (Tensile test) | | |
| Tensile strength (kgf/cm$^2$) | 1080 | 660 |
| Tensile modulus (kgf/cm$^2$) | 52100 | 43700 |
| (Bending test) | | |
| Bending strength (kgf/cm$^2$) | 625 | 365 |
| Bending modulus (kgf/cm$^2$) | 42000 | 46600 |

[1]SUMIKA SUPER LCP E6000 available from Sumitomo Chemical Co., Ltd.
[2]NEOFLON PFA AP-201 available from Daikin Industries, Ltd.

INDUSTRIAL APPLICABILITY

The fluorine-containing polymer with functional group which is prepared by polymerizing the fluorine-containing olefin with functional group of the present invention has good affinity with various heat-resisting thermoplastic resins to form homogeneous dispersion.

Further the molded articles prepared by molding the thermoplastic resin composition comprising the above-mentioned polymer and thermoplastic resin have excellent mechanical properties, moldability, thermal resistance and chemical resistance.

We claim:

1. A fluorine-containing olefin represented by the formula (IV):

$$CH_2=CFCF_2-R_f^6-(CH_2)_k-X^2 \qquad (IV)$$

wherein $X^2$ is

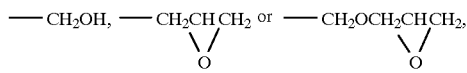

$R_f^6$ is a fluorine-substituted alkylene group having 1 to 40 carbon atoms or $-OR_f^7-$ ($R_f^7$ is a fluorine-substituted fluorine-containing alkylene group having 1 to 40 carbon atoms or a fluorine-substituted fluorine-containing ether group having 3 to 50 carbon atoms), k is 0 or an integer of 1 to 6.

2. A fluorine-containing olefin represented by the formula (V):

$$CH_2=CFCF_2-R_f^8-(CH_2)_m-COOR^4 \qquad (V)$$

wherein $R^4$ is H, an alkyl group having 1 to 6 carbon atoms, Na, K, Li or NH$_4$, $R_f^8$ is a fluorine-substituted alkylene group having 3 to 40 carbon atoms or $-OR_f^9-$ ($R_f^9$ is a fluorine-substituted alkylene group having 2 to 40 carbon atoms or a fluorine-substituted ether group having 3 to 50 carbon atoms), m is 0 or an integer of 1 to 6.

3. The fluorine-containing olefin of claim 1, wherein said $X^2$ is $-CH_2OH$.

4. The fluorine-containing olefin of claim 1, wherein said $X^2$ is

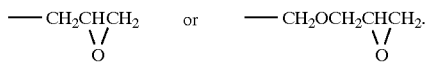

5. The fluorine-containing olefin of claim 1, wherein said —$R_f^6$— is —$CF_2$—$(CF_2CF_2)$— (n is 0 or an integer of 1 to 10).

6. The fluorine-containing olefin of claim 1, wherein said —$R_f^6$— is

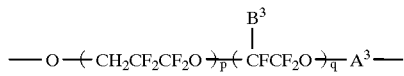

($A^3$ is

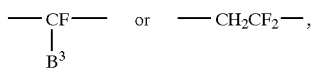

$B^3$ is $CF_3$ or F, p is 0 or an integer of 1 to 5, q is 0 or an integer of 1 to 10) and k is 0 and $X^2$ is

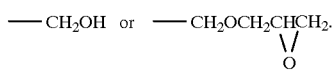

7. The fluorine-containing olefin of claim 2, wherein said $R^4$ is H.

8. The fluorine-containing olefin of claim 2, wherein said $R^4$ is $NH_4$.

9. The fluorine-containing olefin of claim 2, wherein said —$R_f^8$— is —$CF_2$—$(CF_2CF_2)_r$— (r is an integer of 1 to 10).

10. The fluorine-containing olefin of claim 2, wherein said —$R_f^8$— is

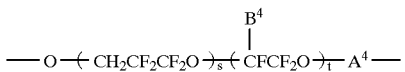

($A^4$ is

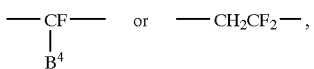

$B^4$ is $CF_3$ or F, s is 0 or an integer of 1 to 5, t is 0 or an integer of 1 to 10, $B^4$ is $CF_3$ in case of r=s=0) and m is 0.

* * * * *